(12) United States Patent
Salvino et al.

(10) Patent No.: US 6,639,023 B1
(45) Date of Patent: Oct. 28, 2003

(54) FLUOROPHENYL RESIN COMPOUNDS

(75) Inventors: Joseph M. Salvino, Schwenksville, PA (US); Robert D. Groneberg, Collegeville, PA (US); John E. Airey, East Norriton, PA (US); Gregory B. Poli, Perkasie, PA (US); Gerard M. McGeehan, Chester Springs, PA (US); Richard F. Labaudiniere, Collegeville, PA (US); François-Frédéric Clerc, Antony (FR); Daniel Noël André Bezard, Bagnolet (FR)

(73) Assignee: Aventis Pharmaceuticals Inc., Bridgewater, NJ (US)

( * ) Notice: Subject to any disclaimer, the term of this patent is extended or adjusted under 35 U.S.C. 154(b) by 0 days.

(21) Appl. No.: 09/487,950

(22) Filed: Jan. 19, 2000

Related U.S. Application Data

(63) Continuation of application No. PCT/US99/14252, filed on Jun. 23, 1999.
(60) Provisional application No. 60/090,558, filed on Jun. 24, 1998.

(51) Int. Cl.[7] .................................................. C08F 8/34
(52) U.S. Cl. ................................. 525/332.2; 525/333.3; 525/333.6; 525/343
(58) Field of Search ........................... 525/332.2, 333.3, 525/333.6, 343

(56) References Cited

U.S. PATENT DOCUMENTS 5,830,539 A * 11/1998 Yan et al. .................. 427/2.13

OTHER PUBLICATIONS

CA Abstract 1994:12383 "Polymers with Reactive Functions as Sampling and Derivatizing agents . . . " Jedrzejczak et al, Analyst(1993), 118(11), 1383–7.*
CA Abstract 1994:108048 Grigorev et al, SU 1,761,762, Sep. 1992.*

* cited by examiner

*Primary Examiner*—Bernard Lipman
(74) *Attorney, Agent, or Firm*—George G. Wang

(57) ABSTRACT

This invention is directed to a fluorophenyl resin compound, to methods of its preparation; and to its use in the solid phase synthesis of amides, peptides, hydroxamic acids, amines, urethanes, carbonates carbamates, sulfonamides and α-substituted carbonyl compounds.

68 Claims, No Drawings

FLUOROPHENYL RESIN COMPOUNDS

CROSS REFERENCE TO RELATED APPLICATIONS

This is a continuation of International Patent Application No. PCT/US99/14252, filed Jun. 23, 1999, which, in turn, is a continuation-in-part of U.S. Provisional Application No. 60/090,558, filed Jun. 24, 1998, now abandoned.

FIELD OF THE INVENTION

This invention is directed to a fluorophenyl resin compound and its derivatives, to methods of its preparation and to its use in the solid phase synthesis of amides, peptides, hydroxamic acids, amines, urethanes, carbonates, carbamates, sulfonamides and a-substituted carbonyl compounds.

BACKGROUND OF THE INVENTION

Solid-phase synthetic techniques, in which a reagent is immobilized on a polymeric material which is inert to the reagents and reaction conditions employed, as well as being insoluble in the media used, are important synthetic tools for preparing amides and peptides as well as for effecting various functional group transformations. For solid phase peptide synthesis, a summary of the many techniques may be found in J. M. Stewart and J. D. Young, *Solid Phase Peptide Synthesis*, 2nd. Ed., Pierce Chemical Co. (Chicago, Ill., 1984); J. Meienhofer, *Hormonal Proteins and Peptides*, vol. 2, p. 46, Academic Press (New York), 1973; and E. Atherton and R. C. Sheppard, *Solid Phase Peptide Synthesis: A Practical Approach*, IRL Press at Oxford University Press (Oxford, 1989). For the use of solid phase methodology in the preparation of non-peptide molecules see Leznoff, C. C., *Acc. Chem. Res.*, 11, 327–333 (1978). For the use of polymeric reagents in functional group transformations see A. Akelah and D. C. Sherrington, Application of Functionalized Polymers in Organic Synthesis, *Chem Rev.*, 81, 557–587 (1981) and W. T. Ford and E. C. Blossey, *Polymer Supported Reagents, Polymer supported Catalysts, and Polymer Supported Coupling Reactions*, in Preparative Chemistry using Supported Reagents, Pierre Laszlo, ed., Academic Press, Inc., 193–212 (1987). For the use of polymeric reagents in oxidation reactions see J. M. J. Frechet et al., *J. Org. Chem.*, 43, 2618 (1978) and G. Cainelli et al., *J. Am. Chem. Soc.*, 98, 6737 (1976). For the use of polymeric reagents in halogenation reactions see J. M. J. Frechet et al., *J. Macromol. Sci. Chem.*, A-11, 507 (1977) and D. C. Sherrington et al., *Eur. Polym. J.*, 13, 73, (1977). For the use of polymeric reagents in epoxidation reactions see J. M. J. Frechet et al., *Macromolecules*, 8, 130 (1975) and C. R. Harrison et al., *J. Chem. Soc. Chem. Commun.*, 1009 (1974). For the use of polymeric reagents in acylation reactions see M. B. Shambhu et al., *Tet. Lett.*, 1627 (1973) and M. B., Shambhu et al., *J. Chem. Soc. Chem. Commun.*, 619 (1974). For the use of polymeric reagents in Wittig reactions see S. V. McKinley et al., *J. Chem. Soc. Chem. Commun.*, 134 (1972).

Polymeric reagents also have found widespread use in combinatorial synthesis and for preparing combinatorial libraries. See F. Balkenhohl et al., *Angew. Chem. Int. Ed. Engl.*, 35, 2288–2337 (1996) and L. A. Thompson et al., *Chem Rev.*, 96, 555–600 (1996).

A 4-hydroxy-tetrafluorophenoxy resin compound of formula

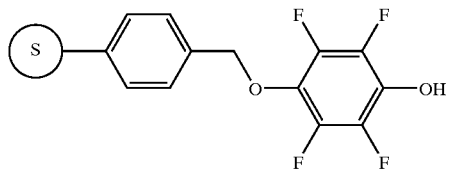

is disclosed by H. Shao et al., in Abstract No.: 072, *Development of TFP Resin for Combinatorial Library Synthesis*, Division of Organic Chemistry, 213th ACS National Meeting, Apr. 13–17, 1997.

SUMMARY OF THE INVENTION

This invention is directed to a fluorophenyl resin compound of formula I

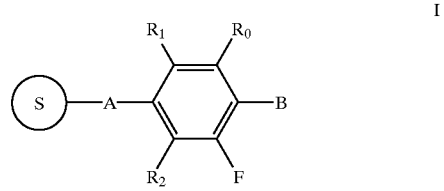

wherein

is a solid support;
A is selected from

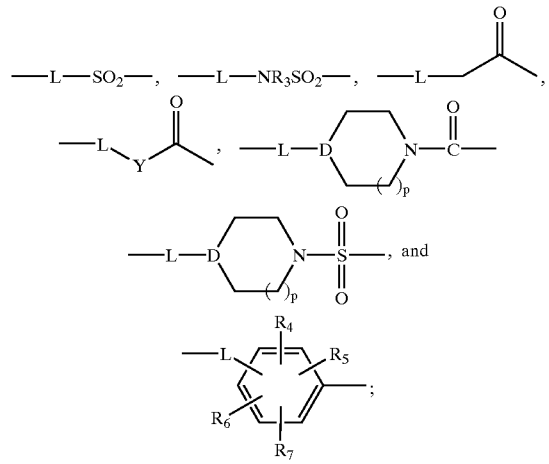

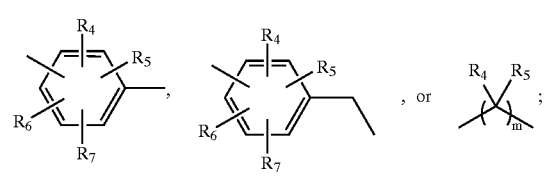

L is a chemical bond,
m is 1 to 5;
p is 0, 1 or 2;

B is F, OW or SO$_2$Z;

D is CH or N;

W is hydrogen, tripyrrolidinophosphonium, C(O)V, C(O)R$_a$, C(O)NR$_b$R$_c$, C(O)OR$_a$, SO$_2$R$_a$ or

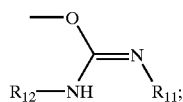

V is Cl or imidazol-1-yl;

Y is O or NR$_3$;

Z is Cl, —OH, OR$_a$ or NR$_a$R$_f$;

R$_a$ and R$_f$ are independently aliphatic or aromatic;

R$_b$ and R$_c$ are independently H, aliphatic or aromatic, or R$_b$ and R$_c$, taken together with the N atom through which they are attached, form an azaheterocyclyl or azaheterocyclenyl;

R$_i$ is CH$_2$R$_f$;

R$_0$, R$_1$ and R$_2$ are independently a ring system substituent, or R$_0$ and R$_1$ taken together with the adjacent carbon atoms through which they are linked form a 6 membered aryl or 5 to 6 membered heteroaryl;

R$_3$ is H or lower alkyl;

R$_4$, R$_5$, R$_6$ and R$_7$ are independently ring system substituents, or R$_4$ and R$_5$ taken together with the carbon atoms through which they are linked form a 6 membered aryl or 5 to 6 membered heteroaryl; and.

R$_{11}$, and R$_{12}$ are independently alkyl, heteroaryl, or aryl.

The fluorophenyl resin compounds of this invention possess a unique advantage over other solid-phase synthesis reagents in that the fluorine atom ortho to the B substituent permit the absolute loading of the resin to be determined using $^{19}$F NMR. The large chemical shift differences seen in the spectrum due to the different environments of the ortho fluoro atoms depending whether the chemical species is a phenolate anion, a phenol or a phenolate ester, is extremely useful to monitor the extent of loading of reagents on the tetrafluoro polymer (TFP) resin. The progress of reactions performed on the fluorophenyl resin compounds of this invention may also be monitored by $^{19}$F NMR, providing a useful analytical method for reaction optimization. This is especially useful in the case of the activated sulfonate esters where there is not a simple diagnostic IR signal to monitor the-reaction.

In another aspect, this invention is directed to a fluorophenyl activated ester resin compound of formula

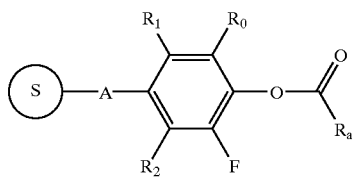

wherein

R$_a$ is aliphatic or aromatic;

is a solid support;

A is selected from

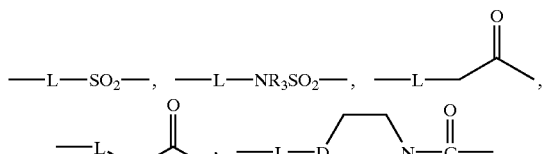

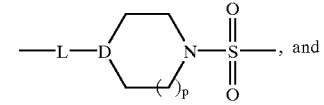

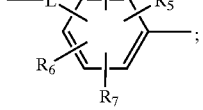

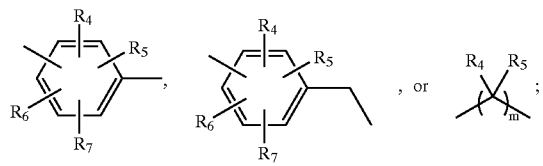

L is a chemical bond,

D is CH or N;

m is 1 to 5;

Y is NR$_3$ or O;

R$_0$, R$_1$ and R$_2$ are independently a ring system substituent, or R$_0$ and R$_1$ taken together with the adjacent carbon atoms through which they are linked form a 6 membered aryl or 5 to 6 membered heteroaryl; and R$_4$, R$_5$, R$_6$ and R$_7$ are independently ring system substituents, or R$_4$ and R$_5$ taken together with the carbon atoms through which they are linked form a 6 membered aryl or 5 to 6 membered heteroaryl.

In another aspect, this invention is directed to a process for preparing an amide of formula

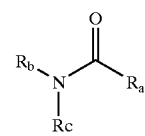

wherein

R$_a$ is aliphatic or aromatic; and

R$_b$ and R$_c$ are independently H, aliphatic or aromatic, or R$_b$ and R$_c$, taken together with the N atom through which they are attached, form an azaheterocyclyl or azaheterocyclenyl, comprising reacting a fluorophenyl activated ester resin compound of formula

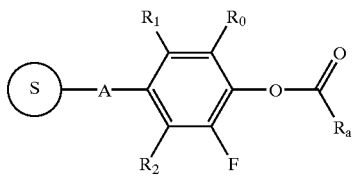

wherein $R_a$ is aliphatic or aromatic;

is a solid support;

A is selected from

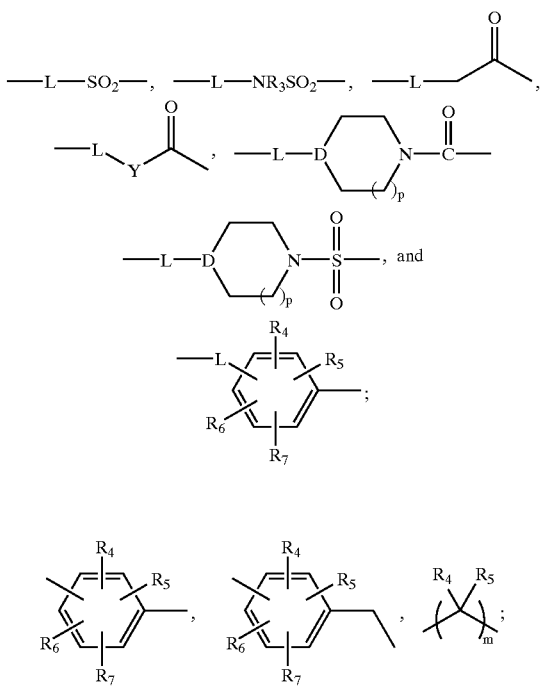

L is a chemical bond,

D is CH or N;

m is 1 to 5;

Y is $NR_3$ or O;

$R_0$, $R_1$ and $R_2$ are independently a ring system substituent, or $R_0$ and $R_1$ taken together with the adjacent carbon atoms through which they are linked form a 6 membered aryl or 5 to 6 membered heteroaryl; and $R_4$, $R_5$, $R_6$ and $R_7$ are independently ring system substituents, or $R_4$ and $R_5$ taken together with the carbon atoms through which they are linked form a 6 membered aryl or 5 to 6 membered heteroaryl with a compound of formula $HNR_bR_c$.

In another aspect, this invention is directed to a process for preparing a fluorophenyl activated ester resin compound of formula

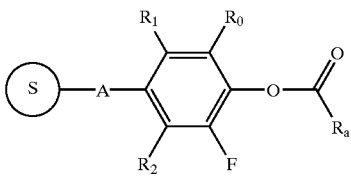

wherein $R_a$ is aliphatic or aromatic;

is a solid support;

A is selected from

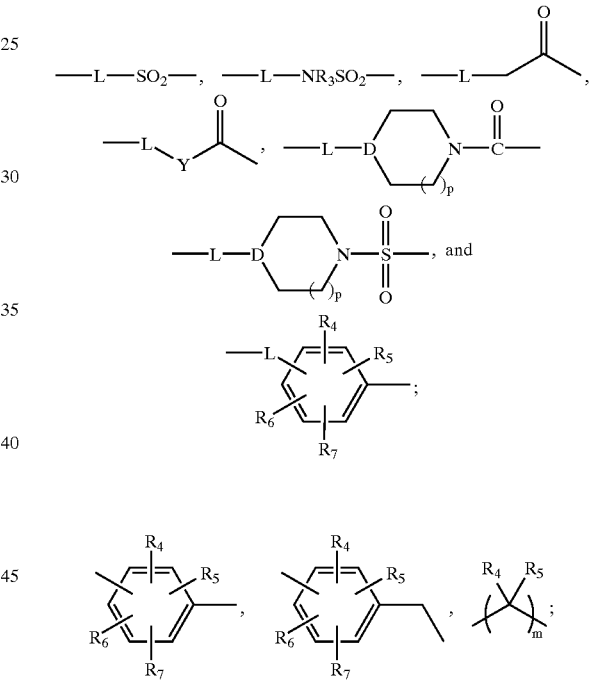

L is a chemical bond, m is 1 to 5;

D is CH or N;

Y is $NR_3$ or O;

$R_0$, $R_1$ and $R_2$ are independently a ring system substituent, or $R_0$ and $R_1$ taken together with the adjacent carbon atoms through which they are linked form a 6 membered aryl or 5 to 6 membered heteroaryl; and $R_4$, $R_5$, $R_6$ and $R_7$ are independently ring system substituents, or $R_4$ and $R_5$ taken together with the carbon atoms through which they are linked form a 6 membered aryl or 5 to 6 membered heteroaryl, comprising coupling a 4-hydroxyfluorophenyl resin compound of formula

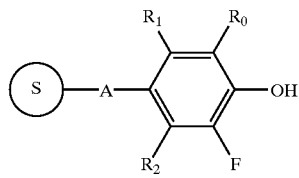

wherein

A, $R_0$, $R_1$ and $R_2$ are defined above,
with a carboxylic acid compound of formula $R_aCO_2H$, wherein $R_a$ is defined above, optionally in the presence of an activating agent selected from the group consisting of diisopropylcarbodiimide in the presence of 4-dimethylaminopyridine, and bromotripyrrolidinophosphonium hexafluorophosphate (PyBroP™) in the presence of triethylamine (TEA).

In another aspect, this invention is directed to a process for preparing an amine compound of formula

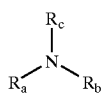

wherein $R_a$ is aliphatic or aromatic;

$R_b$ and $R_c$ are independently H, aliphatic or aromatic, or $R_b$ and $R_c$, taken together with the N atom through which they are attached, form an azaheterocyclyl or azaheterocyclenyl, comprising reacting a 4-(oxysulfonyl)fluorophenyl resin compound of formula

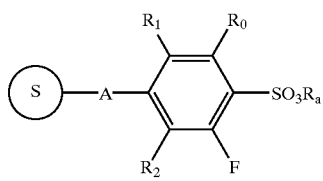

wherein $R_a$ is defined above;

is a solid support;
A is selected from

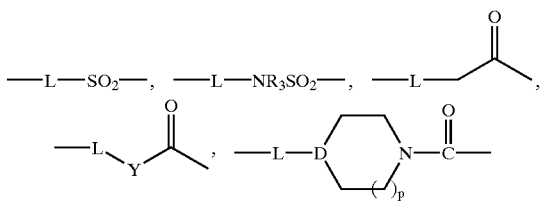

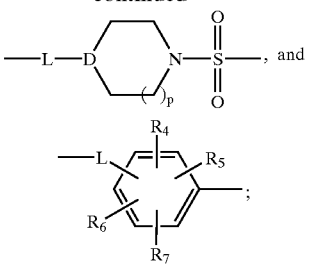

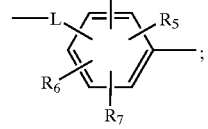

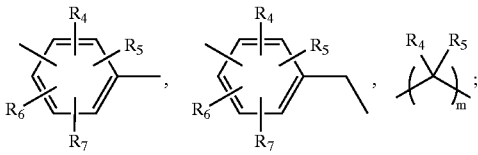

L is a chemical bond,
D is CH or N;
m is 1 to 5;
Y is $NR_3$ or O; and
$R_0$, $R_1$ and $R_2$ are independently a ring system substituent, or $R_0$ and $R_1$ taken together with the adjacent carbon atoms through which they are linked form a 6 membered aryl or 5 to 6 membered heteroaryl, with a compound of formula $HNR_bR_c$.

In another aspect, this invention is directed to a process for preparing a 4-(oxysulfonyl)fluorophenyl resin compound of formula

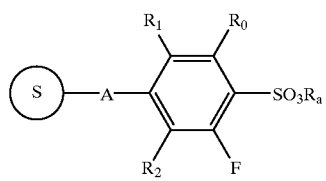

wherein
$R_a$ is aliphatic or aromatic;

is a solid support;
A is selected from

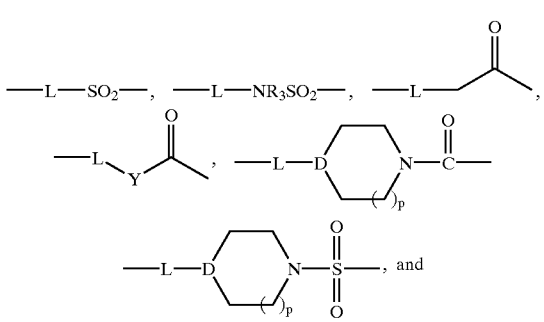

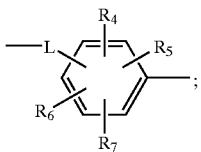

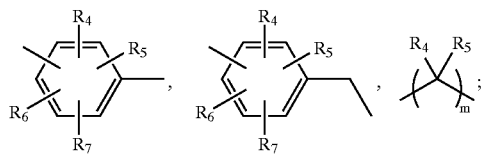

L is a chemical bond,
D is CH or N;
m is 1 to 5;
Y is $NR_3$ or O;
$R_0$, $R_1$ and $R_2$ are independently a ring system substituent, or $R_0$ and $R_1$ taken together with the adjacent carbon atoms through which they are linked form a 6 membered aryl or 5 to 6 membered heteroaryl; and
$R_4$, $R_5$, $R_6$ and $R_7$ are independently ring system substituents, or $R_4$ and $R_5$ taken together with the carbon atoms through which they are linked form a 6 membered aryl or 5 to 6 membered heteroaryl, comprising reacting a fluorophenyl-4-sulfonyl chloride resin compound of formula

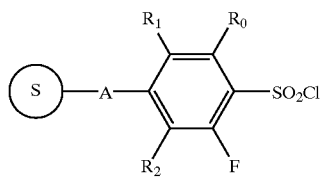

wherein

A, $R_0$, $R_1$ and $R_2$ are defined above,
with a hydroxy compound of formula $R_aOH$, wherein $R_a$ is defined above.

In another aspect, this invention is directed to a process for preparing a sulfonamide compound of formula

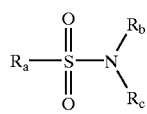

wherein
$R_a$ is aliphatic or aromatic; and
$R_b$ and $R_c$ are independently H, aliphatic or aromatic, or $R_b$ and $R_c$, taken together with the N atom through which they are attached, form an azaheterocyclyl or azaheterocyclenyl,
comprising reacting a 4-(sulfonyloxy)fluorophenyl resin compound of formula

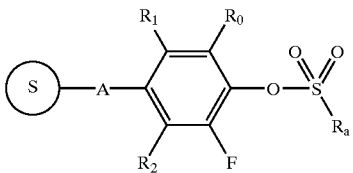

$R_a$ is aliphatic or aromatic;

is a solid support;
A is selected from

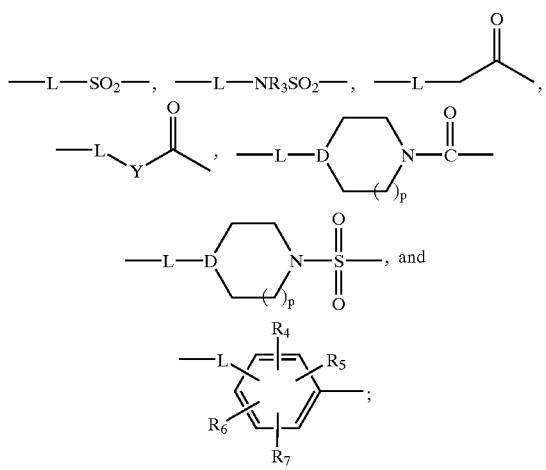

L is a chemical bond,
D is CH or N;
m is 1 to 5;
Y is $NR_3$ or O;
$R_0$, $R_1$ and $R_2$ are independently a ring system substituent, or $R_0$ and $R_1$ taken together with the adjacent carbon atoms through which they are linked form a 6 membered aryl or 5 to 6 membered heteroaryl; and
$R_4$, $R_5$, and $R_6$ are independently ring system substituents, or $R_4$ and $R_5$ taken together with the carbon atoms through which they are linked form a 6 membered aryl or 5 to 6 membered heteroaryl, with an amine compound of formula $HNR_bR_c$.

In another aspect, this invention is directed to a process for preparing a 4-(sulfonyloxy)fluorophenyl resin compound of formula

11

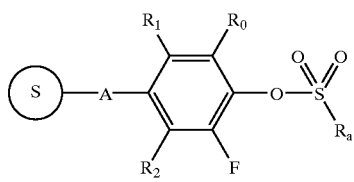

$R_a$ is aliphatic or aromatic;

is a solid support;

A is selected from

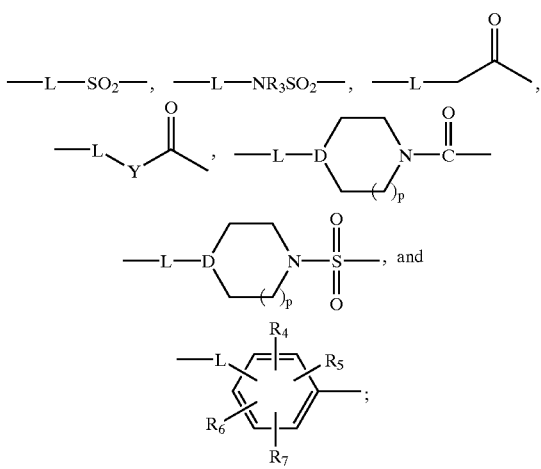

L is a chemical bond,

D is CH or N;

m is 1 to 5;

Y is $NR_3$ or O;

$R_0$, $R_1$ and $R_2$ are independently a ring system substituent, or $R_0$ and $R_1$ taken together with the adjacent carbon atoms through which they are linked form a 6 membered aryl or 5 to 6 membered heteroaryl; and $R_4$, $R_5$, $R_6$ and $R_7$ are independently ring system substituents, or $R_4$ and $R_5$ taken together with the carbon atoms through which they are linked form a 6 membered aryl or 5 to 6 membered heteroaryl;

comprising reacting a 4-hydroxyfluorophenyl resin compound of formula

12

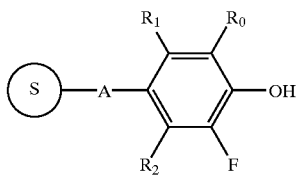

wherein

A, $R_0$, $R_1$ and $R_2$ are defined above, with a sulfonyl chloride compound of formula $R_aSO_2Cl$ in the presence of a base.

In another aspect, this invention is directed to a process for preparing a 4-(sulfonyloxy)fluorophenyl resin compound of formula

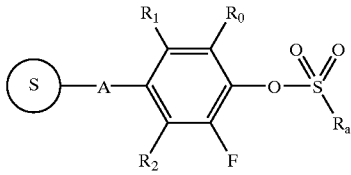

$R_a$ is aliphatic or aromatic;

is a solid support;

A is selected from

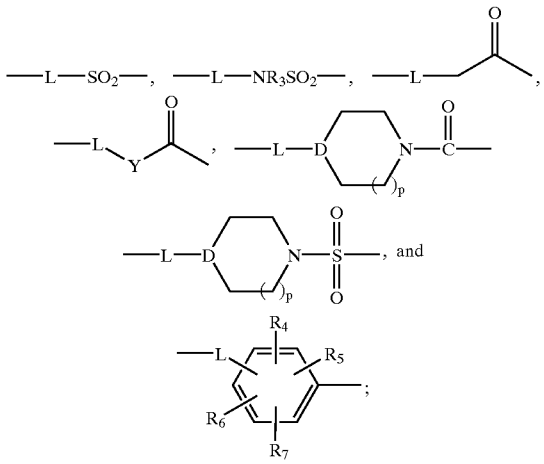

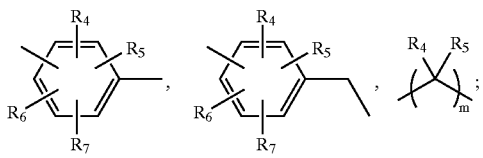

L is a chemical bond,

D is CH or N;

m is 1 to 5;

Y is $NR_3$ or O;

$R_0$, $R_1$ and $R_2$ are independently a ring system substituent, or $R_0$ and $R_1$ taken together with the adjacent carbon atoms through which they are linked form a 6 membered aryl or 5 to 6 membered heteroaryl; and $R_4$, $R_5$, $R_6$ and $R_7$ are independently ring system substituents, or $R_4$ and $R_5$ taken together with the carbon atoms through which they are linked form a 6 membered aryl or 5 to 6 membered heteroaryl;

comprising coupling a 4-hydroxyfluorophenyl resin compound of formula

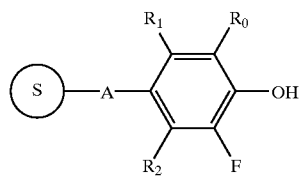

wherein

A, $R_0$, $R_1$ and $R_2$ are defined above, with a sulfonic acid compound of formula $R_aSO_3H$, wherein $R_a$ is defined above.

In another aspect, this invention is directed to a process for preparing a 4-(sulfonyloxy)fluorophenyl resin compound of formula

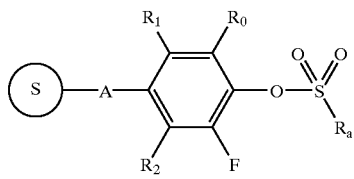

$R_a$ is aliphatic or aromatic;

is a solid support;

A is selected from

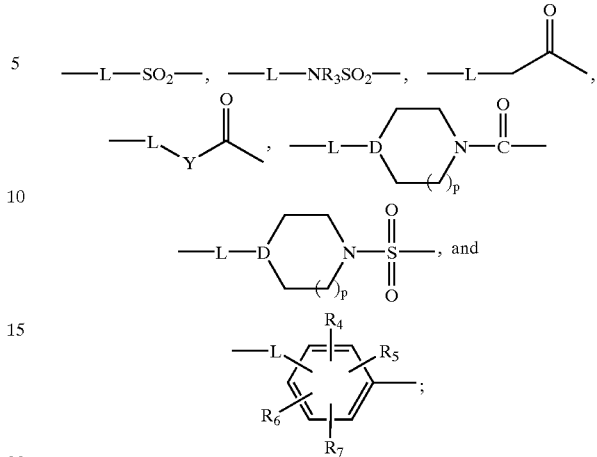

L is a chemical bond,

D is CH or N;

m is 1 to 5;

Y is $NR_3$ or O;

$R_0$, $R_1$ and $R_2$ are independently a ring system substituent, or $R_0$ and $R_1$ taken together with the adjacent carbon atoms through which they are linked form a 6 membered aryl or 5 to 6 membered heteroaryl; and $R_4$, $R_5$, $R_6$ and $R_7$ are independently ring system substituents, or $R_4$ and $R_5$ taken together with the carbon atoms through which they are linked form a 6 membered aryl or 5 to 6 membered heteroaryl;

comprising reacting a 4-hydroxyfluorophenyl resin compound of formula

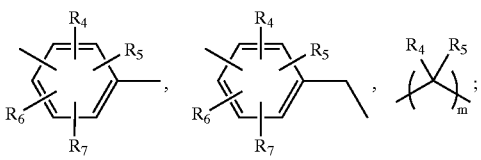

wherein

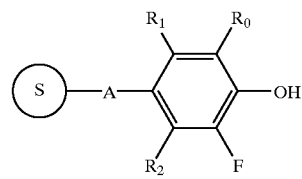

A, $R_0$, $R_1$ and $R_2$ are defined above, with a sulfonic anhydride compound of formula $(R_aSO_2)_2O$.

In another aspect, this invention is directed to a process for preparing a compound of formula

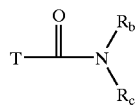

wherein

T is $R_aO—$ or $R_dR_eN—$ $R_a$ is aliphatic or aromatic; and $R_b$, $R_c$, $R_d$ and $R_e$ are independently H, aliphatic or aromatic, or $R_b$ and $R_c$, taken together with the N atom through which they are attached, form an azaheterocyclyl or azaheterocyclenyl, or $R_d$ and $R_e$ taken together with the N atom through which they are attached, form an azaheterocyclyl or azaheterocyclenyl, comprising reacting a 4-(aminocarbonyloxy)fluorophenyl resin compound of formula

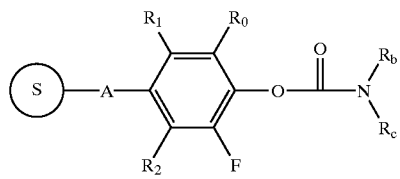

wherein

is a solid support;

A is selected from

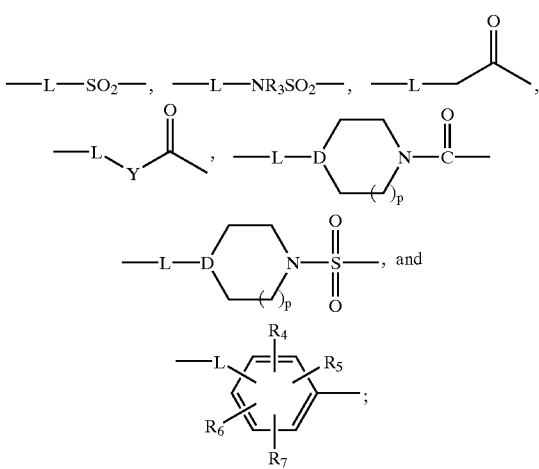

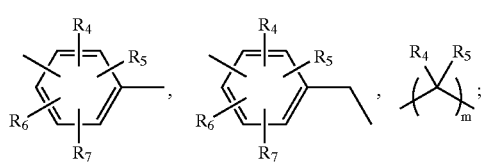

L is a chemical bond,
D is CH or N;
m is 1 to 5;

Y is $NR_3$ or O;

$R_0$, $R_1$ and $R_2$ are independently a ring system substituent, or $R_0$ and $R_1$ taken together with the adjacent carbon atoms through which they are linked form a 6 membered aryl or 5 to 6 membered heteroaryl; and $R_4$, $R_5$, $R_6$ and $R_7$ are independently ring system substituents, or $R_4$ and $R_5$ taken together with the carbon atoms through which they are linked form a 6 membered aryl or 5 to 6 membered heteroaryl;

with an alcohol of formula $R_aOH$, wherein $R_a$ is defined above, or a compound of formula $R_dR_eNH$, wherein $R_d$ and $R_e$ are defined above, in the presence of base.

In another aspect, this invention is directed to a process for preparing a compound of formula

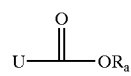

wherein

U is $R_fO—$ or $R_bR_cN—$ $R_a$ and $R_f$ are independently aliphatic or aromatic; and $R_b$ and $R_c$ are independently H, aliphatic or aromatic, or $R_b$ and $R_c$, taken together with the N atom through which they are attached, form an azaheterocyclyl or azaheterocyclenyl, comprising reacting a 4-(oxycarbonyloxy)fluorophenyl resin compound of formula

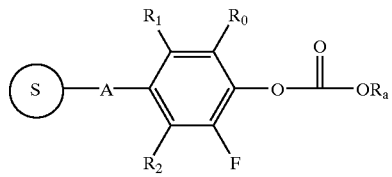

wherein $R_a$ is aliphatic or aromatic;

is a solid support;

A is selected from

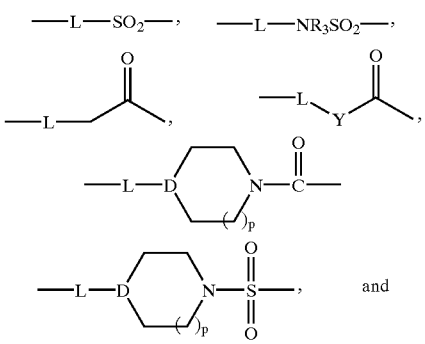

-continued

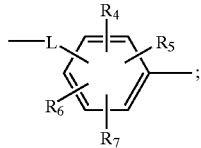

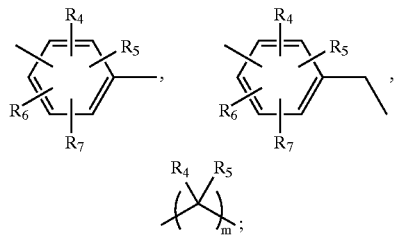

L is a chemical bond,
D is CH or N;
m is 1 to 5;
Y is $NR_3$ or O;
$R_0$, $R_1$ and $R_2$ are independently a ring system substituent, or $R_0$ and $R_1$ taken together with the adjacent carbon atoms through which they are linked form a 6 membered aryl or 5 to 6 membered heteroaryl; and
$R_4$, $R_5$, $R_6$ and $R_7$ are independently ring system substituents, or $R_4$ and $R_5$ taken together with the carbon atoms through which they are linked form a 6 membered aryl or 5 to 6 membered heteroaryl;

with an alcohol of formula $R_fOH$, wherein $R_f$ is defined above, or a compound of formula $R_bR_cNH$, wherein $R_b$ and $R_c$ are defined above, in the presence of base.

In another aspect, this invention is directed to a process for preparing a 4-(aminocarbonyloxy)fluorophenyl resin compound of formula

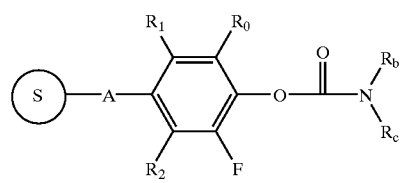

wherein

is a solid support;
A is selected from

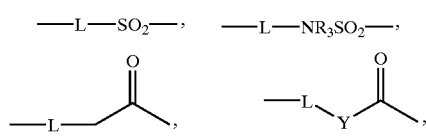

-continued

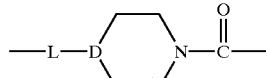

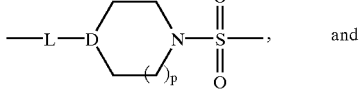
and

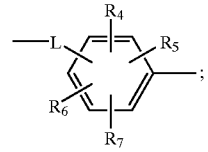

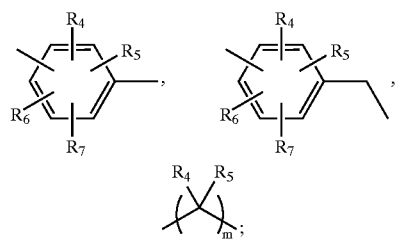

L is a chemical bond,
D is CH or N;
m is 1 to 5;
Y is $NR_3$ or O;
$R_0$, $R_1$ and $R_2$ are independently a ring system substituent, or $R_0$ and $R_1$ taken together with the adjacent carbon atoms through which they are linked form a 6 membered aryl or 5 to 6 membered heteroaryl;
$R_4$, $R_5$, $R_6$ and $R_7$ are independently ring system substituents, or $R_4$ and $R_5$ taken together with the carbon atoms through which they are linked form a 6 membered aryl or 5 to 6 membered heteroaryl;
$R_b$ and $R_c$ are independently H, aliphatic or aromatic, or $R_b$ and $R_c$, taken together with the N atom through which they are attached, form an azaheterocyclyl or azaheterocyclenyl, comprising converting a 4-hydroxyfluorophenyl resin compound of formula

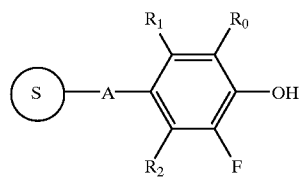

wherein

A, $R_0$, $R_1$ and $R_2$ are defined above, to a 4-(carbonyloxy) fluorophenyl resin compound of formula

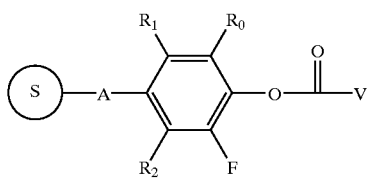

wherein V is Cl or imidazol-1-yl; and reacting the 4-(carbonyloxy)fluorophenyl resin compound of formula

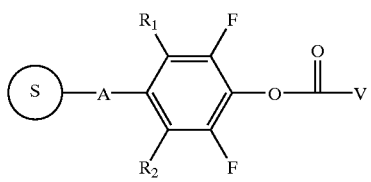

with a compound of formula $R_bR_cNH$, wherein $R_b$ and $R_c$ are defined above, optionally in the presence of base.

In another aspect, this invention is directed to a process for preparing a 4-(aminocarbonyloxy)fluorophenyl resin compound of formula

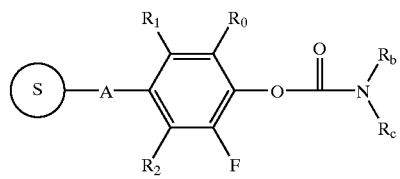

wherein

is a solid support;
A is selected from

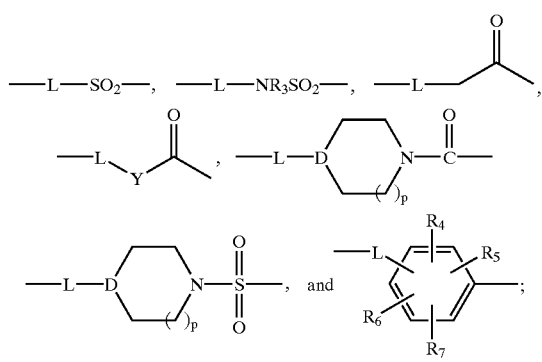

L is a chemical bond,

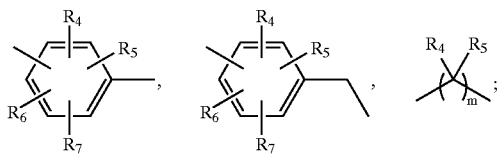

D is CH or N;
m is 1 to 5;
Y is $NR_3$ or O;
$R_0$, $R_1$ and $R_2$ are independently a ring system substituent; or $R_0$ and $R_1$ taken together with the adjacent carbon atoms through which they are linked form a 6 membered aryl or 5 to 6 membered heteroaryl;
$R_4$, $R_5$, $R_6$ and $R_7$ are independently ring system substituents, or $R_4$ and $R_5$ taken together with the carbon atoms through which they are linked form a 6 membered aryl or 5 to 6 membered heteroaryl; and
$R_b$ and $R_c$ are independently H, aliphatic or aromatic, or $R_b$ and $R_c$, taken together with the N atom through which they are attached, form an azaheterocyclyl or azaheterocyclenyl, comprising reacting a 4-hydroxyfluorophenyl resin compound of formula

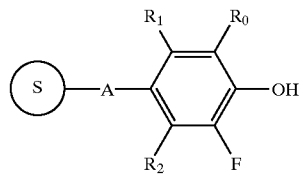

wherein

A, $R_0$, $R_1$ and $R_2$ are defined above,
with a carbamoyl chloride compound of formula

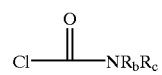

wherein $R_b$ and $R_c$ are defined above, optionally in the presence of base.

In another aspect, this invention is directed to a process for preparing a 4-(aminocarbonyloxy)fluorophenyl resin compound of formula

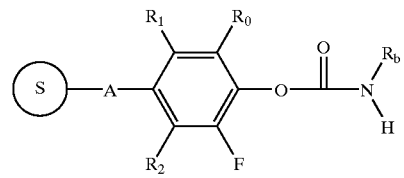

wherein

is a solid support;
A is selected from

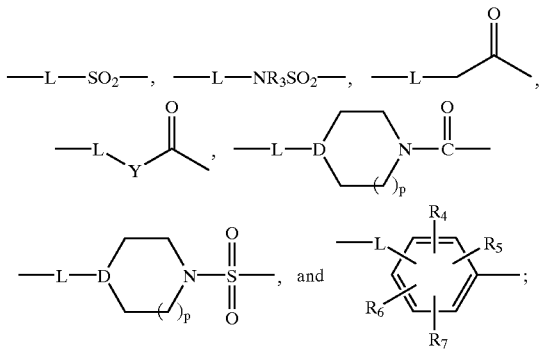

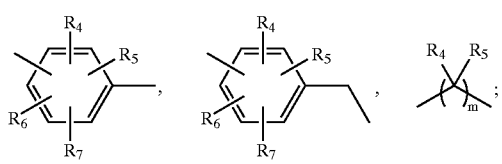

L is a chemical bond,
D is CH or N;
m is 1 to 5;
Y is $NR_3$ or O;
$R_0$, $R_1$ and $R_2$ are independently a ring system substituent, or $R_0$ and $R_1$ taken together with the adjacent carbon atoms through which they are linked form a 6 membered aryl or 5 to 6 membered heteroaryl;
$R_4$, $R_5$, $R_6$ and $R_7$ are independently ring system substituents, or $R_4$ and $R_5$ taken together with the carbon atoms through which they are linked form a 6 membered aryl or 5 to 6 membered heteroaryl; and
$R_b$ is aliphatic or aromatic,
comprising reacting a 4-hydroxyfluorophenyl resin compound of formula

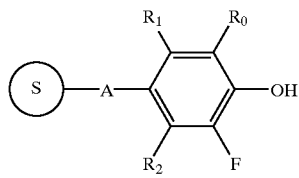

wherein

A, $R_0$, $R_1$ and $R_2$ are defined above, with an isocyanate compound of formula $O=C=N-R_b$,
wherein $R_b$ is defined above, optionally in the presence of base.

In another aspect, this invention is directed to a process for preparing a disubstituted amine compound of formula

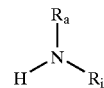

wherein
$R_a$ is aliphatic or aromatic;
$R_i$ is $CH_2R_f$; and
$R_f$ is aliphatic or aromatic,
comprising reacting an N,N-disubstituted fluorophenyl-4-sulfonamido resin compound of formula

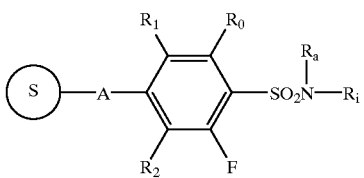

wherein
$R_a$ and $R_i$ are defined above;

is a solid support;
A is selected from

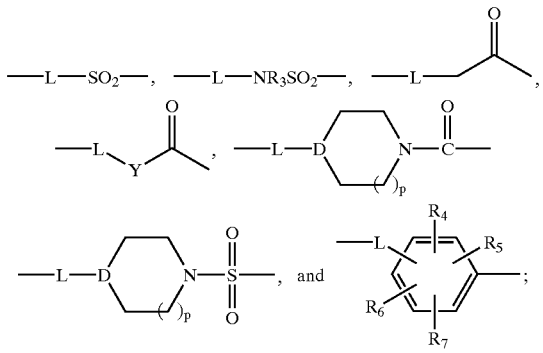

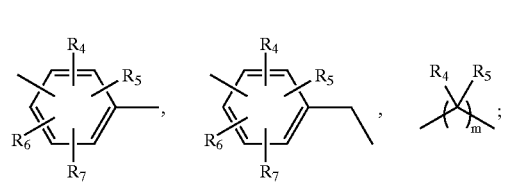

L is a chemical bond,
D is CH or N;
m is 1 to 5;
Y is $NR_3$ or O;
$R_0$, $R_1$ and $R_2$ are independently a ring system substituent, or $R_0$ and $R_1$ taken together with the adjacent carbon atoms through which they are linked form a 6 membered aryl or 5 to 6 membered heteroaryl; and
$R_4$, $R_5$, $R_6$ and $R_7$ are independently ring system substituents, or $R_4$ and $R_5$ taken together with the carbon atoms through which they are linked form a 6 membered aryl or 5 to 6 membered heteroaryl; with a thiol.

In another aspect, this invention is directed to a process for preparing an N,N-disubstituted fluorophenyl-4-sulfonamido resin compound of formula

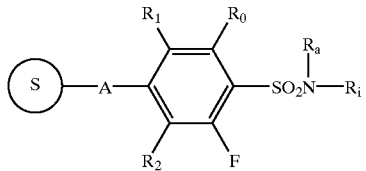

wherein $R_a$ is aliphatic or aromatic;

$R_i$ is $CH_2R_f$;

$R_f$ is aliphatic or aromatic;

is a solid support;

A is selected from

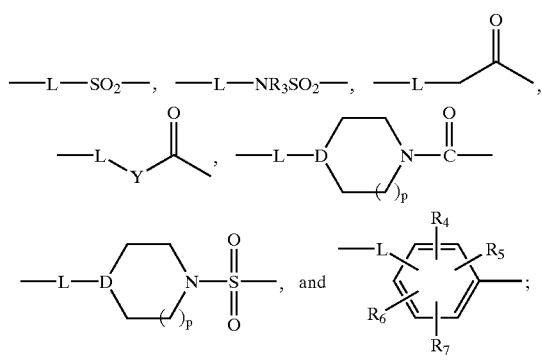

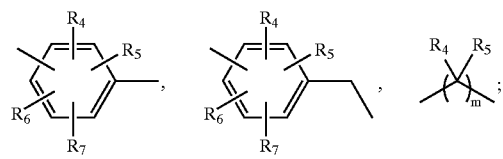

L is a chemical bond,

D is CH or N;

m is 1 to 5;

Y is $NR_3$ or O;

$R_0$, $R_1$ and $R_2$ are independently a ring system substituent, or $R_0$ and $R_1$ taken together with the adjacent carbon atoms through which they are linked form a 6 membered aryl or 5 to 6 membered heteroaryl;

$R_4$, $R_5$, $R_6$ and $R_7$ are independently ring system substituents, or $R_4$ and $R_5$ taken together with the carbon atoms through which they are linked form a 6 membered aryl or 5 to 6 membered heteroaryl; and comprising reacting a 4-fluorophenyl sulfonyl chloride compound of formula

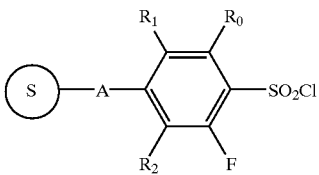

wherein

A, $R_0$, $R_1$ and $R_2$ are defined above, with a compound of formula $H_2NRa$, wherein $R_a$ is defined above, to form a N-substituted 4-(aminosulfonyl)fluorophenyl resin compound of formula

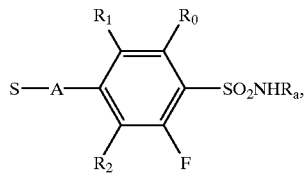

and converting the N-substituted 4-(aminosulfonyl) fluorophenyl resin compound to the N,N-disubstituted 4-(aminosulfonyl)fluorophenyl resin compound.

In another aspect, this invention is directed to a process for preparing a 4-hydroxyfluorophenyl resin compound of formula

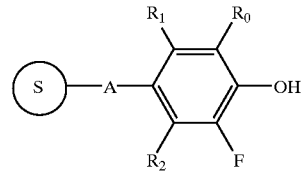

wherein

is a solid support;

A is selected from

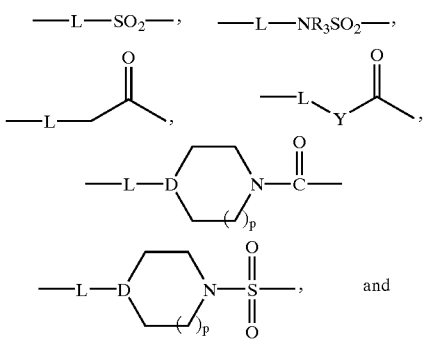

-continued

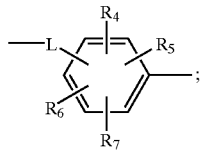

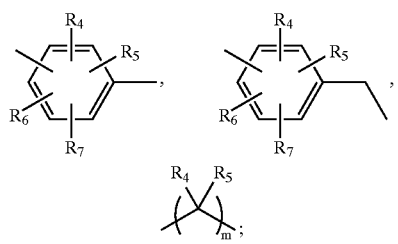

L is a chemical bond,

D is CH or N;

m is 1 to 5;

Y is NR₃ or O;

R₀, R₁ and R₂ are independently a ring system substituent, or R₀ and R₁ taken together with the adjacent carbon atoms through which they are linked form a 6 membered aryl or 5 to 6 membered heteroaryl; and R₄, R₅, R₆ and R₇ are independently ring system substituents, or R₄ and R₅ taken together with the carbon atoms through which they are linked form a 6 membered aryl or 5 to 6 membered heteroaryl; comprising reacting a 4-fluorofluorophenyl resin compound of formula

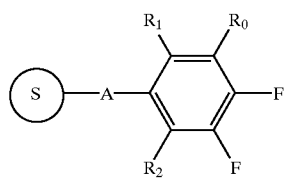

wherein

A, R₀, R₁ and R₂ are defined above, with hydroxide.

In another aspect, this invention is directed to a process for preparing a 4-fluorofluorophenyl resin compound of formula

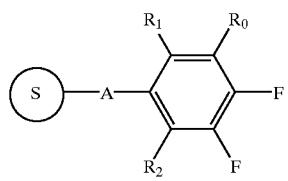

wherein

is a solid support;

A is selected from

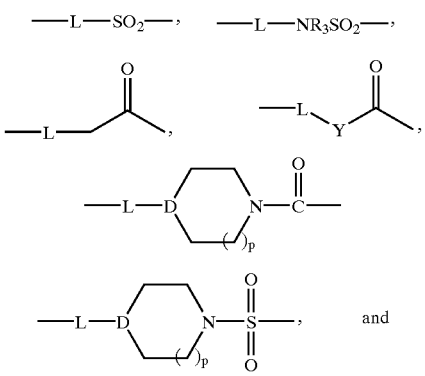

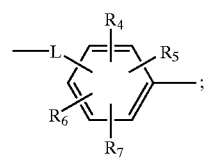

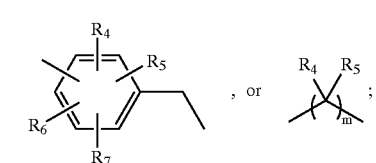

L is a chemical bond,

D is CH or N;

m is 1 to 5;

Y is NR₃ or O;

R₀, R₁ and R₂ are independently a ring system substituent, or R₀ and R₁ taken together with the adjacent carbon atoms through which they are linked form a 6 membered aryl or 5 to 6 membered heteroaryl; and R₄, R₅, R₆ and R₇ are independently ring system substituents, or R₄ and R₅ taken together with the carbon atoms through which they are linked form a 6 membered aryl or 5 to 6 membered heteroaryl;

comprising acylating a resin compound of formula

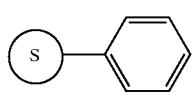

with a 4-fluorofluorobenzoyl chloride compound of formula

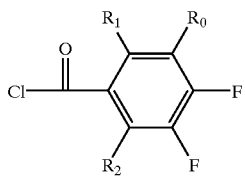

wherein $R_0$, $R_1$ and $R_2$ are defined above.

In another aspect, this invention is directed to a process for preparing a 4-fluorofluorophenyl resin compound of formula

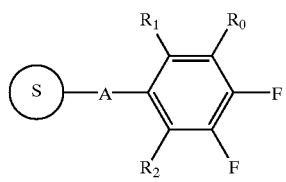

wherein

is a solid support;
A is selected from

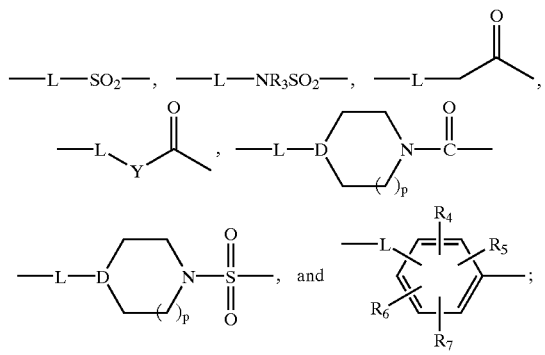

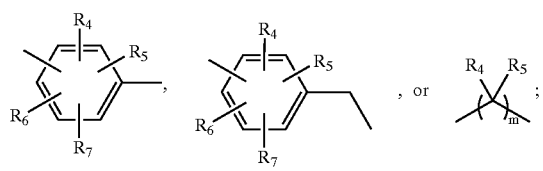

L is a chemical bond,
D is CH or N;
m is 1 to 5;
Y is $NR_3$ or O;
$R_0$, $R_1$ and $R_2$ are independently a ring system substituent, or $R_0$ and $R_1$ taken together with the adjacent carbon atoms through which they are linked form a 6 membered aryl or 5 to 6 membered heteroaryl;
$R_3$ is H; and
$R_4$, $R_5$, $R_6$ and $R_7$ are independently ring system substituents, or $R_4$ and $R_5$ taken together with the carbon atoms through which they are linked form a 6 membered aryl or 5 to 6 membered heteroaryl;
comprising reacting an amino resin of formula

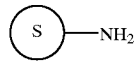

with a 4-fluorofluorophenylsulfonyl chloride compound of formula

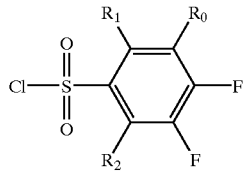

wherein $R_0$, $R_1$ and $R_2$ are defined above, in the presence of base.

In another aspect, this invention is directed to a process for preparing a 4-hydroxyfluorophenyl resin compound of formula

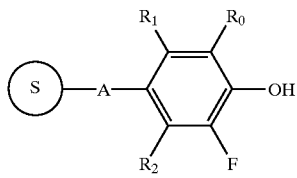

wherein

is a solid support;
A is selected from

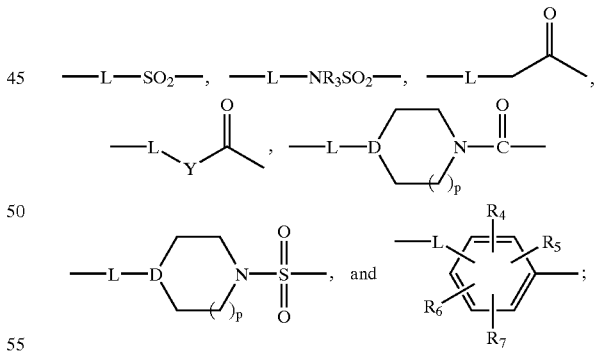

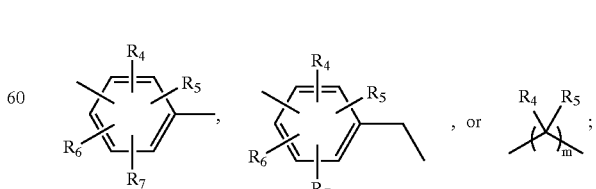

L is a chemical bond,
D is CH or N;

m is 1 to 5;

Y is $NR_3$ or O;

$R_0$, $R_1$ and $R_2$ are independently a ring system substituent, or $R_0$ and $R_1$ taken together with the adjacent carbon atoms through which they are linked form a 6 membered aryl or 5 to 6 membered heteroaryl;

$R_3$ is H; and $R_4$, $R_5$, $R_6$ and $R_7$ are independently ring system substituents, or $R_4$ and $R_5$ taken together with the carbon atoms through which they are linked form a 6 membered aryl or 5 to 6 membered heteroaryl;

comprising coupling an amino resin of formula

with a 4-hydroxyfluorophenyl carboxylic acid compound of formula

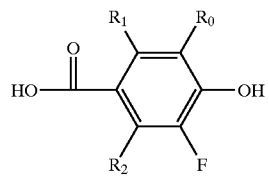

wherein $R_0$, $R_1$ and $R_2$ are defined above.

In another aspect, this invention is directed to a process for preparing a fluorophenyl-4-sulfonic acid resin compound of formula

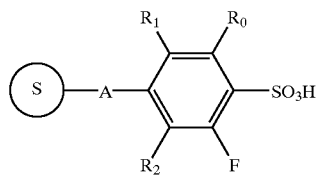

wherein

is a solid support;

A is selected from

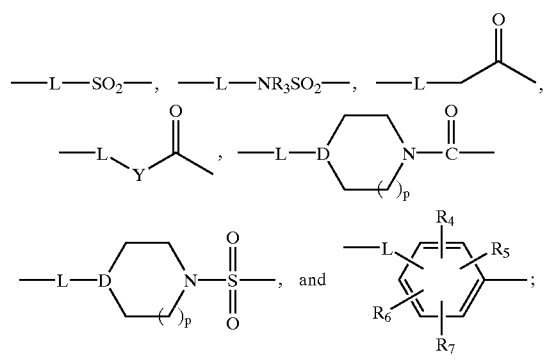

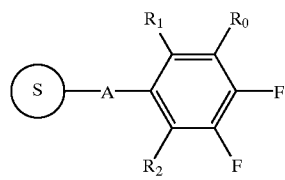

L is a chemical bond,

D is CH or N;

m is 1 to 5;

Y is $NR_3$ or O;

$R_0$, $R_1$ and $R_2$ are independently a ring system substituent, or $R_0$ and $R_1$ taken together with the adjacent carbon atoms through which they are linked form a 6 membered aryl or 5 to 6 membered heteroaryl; and $R_4$, $R_5$, $R_6$ and $R_7$ are independently ring system substituents, or $R_4$ and $R_1$ taken together with the carbon atoms through which they are linked form a 6 membered aryl or 5 to 6 membered heteroaryl;

comprising reacting a 4-fluorofluorophenyl resin compound of formula

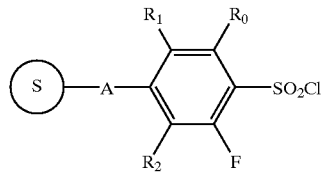

wherein $R_0$, $R_1$ and $R_2$ are defined above, with an $SO_3^-$ equivalent.

In another aspect, this invention is directed to a process for the preparation of a fluorophenyl-4-sulfonyl chloride resin compound of formula

wherein

is a solid support;

A is selected from

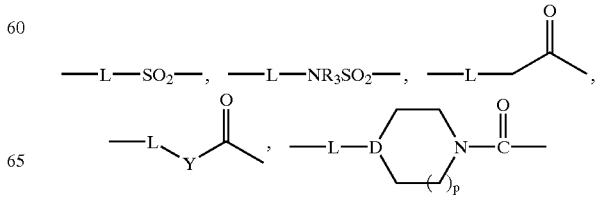

-continued

[chemical structure: —L—D—N—S(=O)₂—, with (CH₂)p]

[chemical structure with R₄, R₅, R₆, R₇ on ring with L]

[three ring structures with R₄, R₅, R₆, R₇]

L is a chemical bond,
D is CH or N;
m is 1 to 5;
Y is NR₃ or O;
R₀, R₁ and R₂ are independently a ring system substituent, or R₀ and R₁ taken together with the adjacent carbon atoms through which they are linked form a 6 membered aryl or 5 to 6 membered heteroaryl; and
R₄, R₅, R₆ and R₇ are independently ring system substituents, or R₄ and R₅ taken together with the carbon atoms through which they are linked form a 6 membered aryl or 5 to 6 membered heteroaryl;
comprising reacting a fluorophenyl-4-sulfonic acid resin compound of formula

[chemical structure: S–A–phenyl with R₀, R₁, R₂, F, SO₃H]

wherein R₀, R₁ and R₂ are defined above, with an inorganic acid chloride.

In another aspect, this invention is directed to a process for preparing an α-substituted carbonyl compound of formula

[chemical structure: R_g–CH(R_h)–C(=O)–R_a]

wherein
R_a is aliphatic or aromatic; and
R_g is H, aliphatic or aromatic and
R_h is aliphatic or aromatic,
comprising reacting a fluorophenyl activated ester resin compound of formula

[chemical structure: S–A–phenyl with R₀, R₁, R₂, F, O–C(=O)–OR_a]

wherein
R_a is aliphatic or aromatic;

[S circle] is a solid support;
A is selected from

—L—SO₂—, —L—NR₃SO₂—, —L—C(=O)—CH₂—,

—L—C(=O)—Y—, —L—D—N—C(=O)— (with (CH₂)p ring),

—L—D—N—S(=O)₂— (with (CH₂)p ring), and

[ring structure with R₄, R₅, R₆, R₇ and L];

[three ring structures with R₄, R₅, R₆, R₇]

L is a chemical bond,
D is CH or N;
m is 1 to 5;
Y is NR₃ or O;
R₀, R₁ and R₂ are independently a ring system substituent, or R₀ and R₁ taken together with the adjacent carbon atoms through which they are linked form a 6 membered aryl or 5 to 6 membered heteroaryl; and
R₄, R₅, R₆ and R₇ are independently ring system substituents, or R₄ and R₅ taken together with the carbon atoms through which they are linked form a 6 membered aryl or 5 to 6 membered heteroaryl; with a carbon nucleophile of formula $R_g R_h CH^-$.

DETAILED DESCRIPTION OF THE INVENTION

Definitions of Terms

As used above and throughout the description of the invention, the following terms, unless otherwise indicated, shall be understood to have the following meanings:

"Solid support" means a substrate which is inert to the reagents and reaction conditions described herein, as well as being substantially insoluble in the media used. Representative solid supports include inorganic substrates such as kieselguhr, silica gel, and controlled pore glass; organic polymers including polystyrene, including 1–2% copolystyrene divinyl benzene (gel form) and 20–40% copolystyrene divinyl benzene (macro porous form), polypropylene, polyethylene glycol, polyacrylamide, cellulose, and the like; and composite inorganic/polymeric compositions such as polyacrylamide supported within a matrix of kieselguhr particles. See J. M. Stewart and J. D. Young, Solid Phase Peptide Synthesis, 2nd. Ed., Pierce Chemical Co. (Chicago, Ill., 1984).

In addition, "solid support" includes a solid support as described above which is affixed to a second inert support such as the pins described in Technical Manual, Multipin™ SPOC, Chiron Technologies (1995) and references therein which comprise a detachable polyethylene- or polyproylene-based head grafted with an amino functionalized methacrylate copolymer and an inert stem.

In addition, "solid support" includes polymeric supports such as the polyethylene glycol supports described by Janda et al., Proc. Natl. Acad. Sci. USA, 92, 6419–6423 (1995) and S. Brenner, WO 95/16918, which are soluble in many solvents but can be precipitated by the addition of a precipitating solvent.

"Polyfluorophenyl resin compound" means a solid support as defined above which is chemically modified as is known in the art to incorporate a plurality of fluorophenyl groups. The fluorophenyl groups are covalently bound directly to the solid support or attached to the solid support by covalent bonds through a linking group. The fluorophenyl resin compounds according to this invention are designated herein as

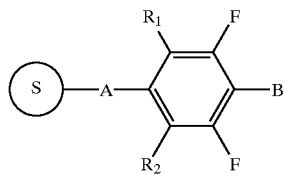

wherein A, R, $R_1$, $R_2$ and B are defined herein, and

denotes a solid support, as defined herein, or the combination of a solid support and a linking group.

"Polyfluorophenyl group" means a group of formula

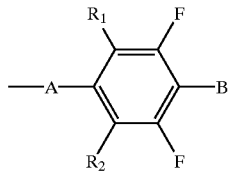

wherein A R, $R_1$, $R_2$ and B are defined herein.

"Linking group" and "linker" mean a group through which the fluorophenyl group may be covalently linked to the solid support. The linking group is substantially inert to the reagents and reaction conditions described herein and generally comprises an inert polymeric material such as polyethylene glycol (PEG, also commonly referred to as polyoxyethylene).

"Amine protecting group" means an easily removable group which is known in the art to protect an amino group against undesirable reaction during synthetic procedures and to be selectively removable. The use of N-protecting groups is well known in the art for protecting amino, and other reactive nitrogen containing groups, against undesirable reactions during a synthetic procedure and many such protecting groups are known, See, for example, T. H. Greene and P. G. M. Wuts, Protective Groups in Organic Synthesis, 2nd edition, John Wiley & Sons, New York (1991), the contents of which are hereby incorporated herein by reference. Preferred N-protecting groups are acyl, including fonnyl, acetyl, chloroacetyl, trichloroacetyl, o-nitrophenylacetyl, o-nitrophenoxyacetyl, trifluoroacetyl, acetoacetyl, 4-chlorobutyryl, isobutyryl, o-nitrocinnamoyl, picolinoyl, acylisothiocyanate, aminocaproyl, benzoyl and the like, and acyloxy including methoxycarbonyl, 9-fluorenylmethoxycarbonyl, 2,2,2-trifluoroethoxycarbonyl, 2-trimethylsilylethxoycarbonyl, vinyloxycarbonyl, t-butyloxycarbonyl (BOC), 1,1-dimethylpropynyloxycarbonyl, benzyloxycarbonyl (CBZ), p-nitrophenylsulfinyl, p-nitrobenzyloxycarbony, 2,4-dichlorobenzyloxycarbonyl, allyloxycarbonyl (Alloc), and the like.

"Carboxylic acid protecting group" and "acid protecting group" mean an easily removable group which is known in the art to protect a carboxylic acid (—$CO_2H$) group against undesirable reaction during synthetic procedures and to be selectively removable. The use of carboxylic acid protecting groups is well known in the art and many such protecting groups are known, See for example, T. H. Greene and P. G. M. Wuts, Protective Groups in Organic Synthesis, 2nd edition, John Wiley & Sons, New York (1991), the contents of which are hereby incorporated herein by reference. Examples of carboxylic acid protecting groups include methoxymethyl, methylthiomethyl, tetrahydropyranyl, benzyloxymethyl, substituted and unsubstituted phenacyl, 2,2,2-trichloroethyl, tert-butyl, cinnamyl, substituted and unsubstituted benzyl, trimethylsilyl, allyl, and the like, and amides and hydrazides groups including N,N-dimethyl, 7-nitroindolyl, hydrazide, N-phenylhydrazide, and the like. Especially preferred carboxylic acid protecting groups are tert-butyl and benzyl.

"Carbon nucleophile," as used herein, refers to an electron pair donor resided on a carbon atom.

"Hydroxy protecting group" means an easily removable group which is known in the art to protect a hydroxy group against undesirable reaction during synthetic procedures and to be selectively removable. The use of hydroxy protecting groups is well known in the art and many such protecting groups are known, see., for example, T. H. Greene and P. G. M. Wuts, Protective Groups in Organic Synthesis, 2nd edition, John Wiley & Sons, New York (1991), incorporated herein by reference. Examples of hydroxy protecting groups include ether groups such as methyl ether; substituted methyl ethers such as methoxymethyl (MOM)ether, methylthiomethyl (MTM) ether, 2-methoxyethoxymethyl (MEM) ether, bis(2-chloroethoxy)methyl ether, tetrahydropyranyl (THP) ether, tetrahydrothiopyranyl ether, 4-methoxytetrahydropyranyl ether, 4-methoxytetrahydrothiopyranyl ether, tetrahydrofuranyl ether, tetrahydrothiofuranyl ether, and the like; substituted ethyl ethers such as 1-ethoxyethyl ether, 1-methyl-1-methoxyethyl ether 2-(phenylselenyl)ethyl ether, t-butyl ether, allyl ether, benzyl ether, o-nitrobenzyl ether, triphenylmethyl ether, α-naphthyldiphenylmethyl ether, p-methoxyphenyl- diphenylmethyl ether, 9-(9-phenyl-10-oxo)anthranyl (tritylone) ether, and the like; silyl ethers such as trimethylsilyl (TMS) ether, isopropyldimethylsilyl ether, t-butyldimethylsilyl (TBDMS) ether, t-butyldiphenylsilyl ether, tribenzylsilyl ether, tri-p-xylylsilyl ether, triisopropylsilyl ether, and the like; esters such as formate, acetate, trichloroacetate, phenoxyacetate, isobutyrate, pivaloate, adamantoate, benzoate, 2,4,6-trimethylbenzoate, and the like; and carbonates such as methyl, 2,2,2-trichloroethyl, allyl, p-nitrophenyl, benzyl, p-nitrobenzyl, S-benzyl thiocarbonate, and the like.

"Amino acid" means an amino acid selected from the group consisting of natural and unnatural amino acids as defined herein.

"Natural amino acid" means an α-amino acid selected from the group consisting of alanine, valine, leucine, isoleucine, proline, phenylalanine, tryptophan, methionine, glycine, serine, threonine, cysteine, tyrosine, asparagine, glutamine, lysine, arginine, histidine, aspartic acid and glutamic acid.

"Unnatural amino acid" means an amino acid for which there is no nucleic acid codon. Examples of unnatural amino acids include, for example, the D-isomers of the natural α-amino acids as indicated above; aminobutyric acid (Abu), aminoisobutyric acid (Aib), 3-aminoisobutyric acid (bAib), norvaline (Nva), β-Ala, 2-aminoadipic acid (Aad), 3-aminoadipic acid (bAad), 2-aminobutyric acid (Abu), γ-aminobutyric acid (Gaba), 6-aminocaproic acid (Acp), 2,4-diaminobutryic acid (Dbu), α-aminopimelic acid, trimethylsilyl-Ala (TMSA), allo-isoleucine (aIle), norleucine (Nle), tert-Leu, citrulline (Cit), ornithine (Orn), 2,2'-diaminopimelic acid (Dpm), 2,3-diaminopropionic acid (Dpr), α- or β-Nal, cyclohexyl-Ala (Cha), hydroxyproline, sarcosine (Sar), and the like; cyclic amino acids; $N^\alpha$-alkylated amino acids such as $N^\alpha$-methylglycine (MeGly), $N^\alpha$-ethylglycine (EtGly) and $N^\alpha$-ethylasparagine (EtAsn); and amino acids in which the α-carbon bears two side-chain substituents.

"Equivalent amino acid" means an amino acid which may be substituted for another amino acid in the peptides according to the invention without any appreciable loss of function. In making such changes, substitutions of like amino acids is made on the basis of relative similarity of side chain substituents, for example regarding size, charge, hydrophilicity, hydropathicity and hydrophobicity as described herein.

"Peptide" and "polypeptide" mean a polymer in which the monomers are natural or unnatural amino acid residues joined together through amide bonds. The term "peptide backbone" means the series of amide bonds through which the amino acid residues are joined. The term "amino acid residue" means the individual amino acid units incorporated into the peptides or polypeptides.

"Aliphatic" means a radical derived from a non aromatic C—H bond by removal of the hydrogen atom. The aliphatic radical may be further substituted by additional aliphatic or aromatic radicals as defined herein. Representative aliphatic groups include alkyl, alkenyl, alkynyl, cycloalkyl, cycloalkenyl, heterocyclyl, heterocyclenyl, aralkenyl, aralkyloxyalkyl, aralkyloxycarbonylalkyl, aralkyl, aralkynyl, aralkyloxyalkenyl, heteroaralkenyl, heteroaralkyl, heteroaralkyloxyalkenyl, heteroaralkyloxyalkyl, heteroaralkynyl, fused arylcycloalkyl, fused heteroarylcycloalkyl, fused arylcycloalkenyl, fused heteroarylcycloalkenyl, fused arylheterocyclyl, fused heteroarylheterocyclyl, fused arylheterocyclenyl, fused heteroarylheterocyclenyl, and the like.

"Aromatic" means a radical containing one or more groups of atoms in a cyclic array that contains clouds of delocalized π electrons above and below the plane of the atoms; furthermore, the πclouds must contain a total of (4q+2)π electrons, where q is any positive integer. "Aromatic" includes both aryl and heteroaryl rings as defined herein. The aryl or heteroaryl ring may be further substituted by additional aliphatic or aromatic radicals as defined herein. Representative aromatic groups include aryl, fused cycloalkenylaryl, fused cycloalkylaryl, fused heterocyclylaryl, fused heterocyclenylaryl, heteroaryl, fused cycloalkylheteroaryl, fused cycloalkenylheteroaryl, fused heterocyclenylheteroaryl, fused heterocyclylheteroaryl, and the like.

"Acyl" means an H—CO— or alkyl-CO— group wherein the alkyl group is as herein described. Preferred acyls contain a lower alkyl. Exemplary acyl groups include formyl, acetyl, propanoyl, 2-methylpropanoyl, butanoyl and palmitoyl.

"Acylamino" is an acyl-NH— group wherein acyl is as defined herein.

"Alkenoyl" means an alkenyl-CO— group wherein alkenyl is as defined herein.

"Alkenyl" means a straight or branched aliphatic hydrocarbon group of 2 to about 15 carbon atoms which contains at least one carbon-carbon double bond. Preferred alkenyl groups have 2 to about 12 carbon atoms; more preferred alkenyl groups have 2 to about 4 carbon atoms. The alkenyl group is optionally substituted with one or more alkyl group substituents as defined herein. Representative alkenyl groups include ethenyl, propenyl, n-butenyl, i-butenyl, 3-methylbut-2-enyl, n-pentenyl, heptenyl, octenyl, cyclohexylbutenyl and decenyl.

"Alkenylenyl" denotes a divalent group derived from a straight or branched chain hydrocarbon containing at least one carbon-carbon double bond. Representative alkenylenyl include —CH═CH—, —CH$_2$CH═CH—, —C(CH$_3$)═CH—, —CH$_2$CH═CHCH$_2$—, and the like.

"Alkenyloxy" means an alkenyl-O— group wherein the alkenyl group is as herein described. Representative alkenyloxy groups include allyloxy or 3-butenyloxy.

"Alkoxy" means an alkyl-O— group wherein the alkyl group is as defined herein. Representative alkoxy groups include methoxy, ethoxy, n-propoxy, i-propoxy, n-butoxy, heptoxy, and the like.

"Alkoxyalkylenyl" means an alkyl-O-alkylenyl-group wherein alkyl and alkylenyl are as defined herein. Representative alkoxyalkylenyl groups include methoxyethyl, ethoxymethyl, n-butoxymethyl and cyclopentylmethyloxyethyl.

"Alkoxyalkoxy" means an alkyl-O-alkylenyl-O— group. Representative alkoxyalkoxy include methoxymethoxy, methoxyethoxy, ethoxyethoxy, and the like.

"Alkoxycarbonyl" means an ester group; i.e. an alkyl-O—CO— group wherein alkyl is as defined herein. Representative alkoxycarbonyl groups include methoxycarbonyl, ethoxycarbonyl, t-butyloxycarbonyl, and the like.

"Alkoxycarbonylalkylenyl" means an alkyl-O—CO-alkylenyl-group wherein alkyl and alkylenyl are as defined herein. Representative alkoxycarbonylalkyl include methoxycarbonylmethyl, and ethoxycarbonylmethyl, methoxycarbonyl ethyl, and the like.

"Alkyl" means an aliphatic hydrocarbon group which may be straight or branched having about 1 to about 20 carbon atoms in the chain. Preferred alkyl groups have 1 to about 12 carbon atoms in the chain. Branched means that one or more lower alkyl groups such as methyl, ethyl or propyl are attached to a linear alkyl chain. "Lower alkyl" means about 1 to about 4 carbon atoms in the chain which may be straight or branched. The alkyl may be substituted with one or more "alkyl group substituents" which may be the same or different, and include halo, cycloalkyl, hydroxy, alkoxy, amino, carbamoyl, acylamino, aroylamino, carboxy, alkoxycarbonyl, aralkyloxycarbonyl, or heteroaralkyloxycarbonyl. Representative alkyl groups include methyl, trifluoromethyl, cyclopropylmethyl, cyclopentylmethyl, ethyl, n-propyl, i-propyl, n-butyl, t-butyl, n-pentyl, 3-pentyl, methoxyethyl, carboxymethyl, methoxycarbonylethyl, benzyloxycarbonylmethyl, and pyridylmethyloxycarbonylmethyl.

"Alkyleny" means a straight or branched bivalent hydrocarbon chain of 1 to about 20 carbon atoms. Alkylenyl may be substituted by one or more alkyl group substituents as defined herein. Preferred alkylenyl groups are the lower alkylenyl groups having 1 to about 4 carbon atoms. Representative alkylenyl groups include methylene, ethylene, and the like.

"Alkylsulfinyl" means an alkyl-SO— group wherein the alkyl group is as defined above. Preferred alkylsulfinyl groups are those wherein the alkyl group is lower alkyl.

"Alkylsulfonyl" means an alkyl-SO$_2$-group wherein the alkyl group is as defined herein. Preferred alkylsulfonyl groups are those wherein the alkyl group is lower alkyl.

"Alkylsulfonylcarbamoyl" means an alkyl-SO$_2$—NH—CO— group wherein alkyl group is defined herein. Preferred alkylsulfonylcarbamoyl groups are those wherein the alkyl group is lower alkyl.

"Alkylthio" means an alkyl-S— group wherein the alkyl group is as defined herein. Preferred alkylthio groups are those wherein the alkyl group is lower alkyl. Representative alkylthio groups include methylthio, ethylthio, i-propylthio, heptylthio, and the like.

"Alkynyl" means a straight or branched aliphatic hydrocarbon group of 2 to about 15 carbon atoms which contains at least one carbon-carbon triple bond. Preferred alkynyl groups have 2 to about 12 carbon atoms. More preferred alkynyl groups contain 2 to about 4 carbon atoms. "Lower alkynyl" means alkynyl of 2 to about 4 carbon atoms. The alkynyl group may be substituted by one or more alkyl group substituents as defined herein. Representative alkynyl groups include ethynyl, propynyl, n-butynyl, 2-butynyl, 3-methylbutynyl, n-pentynyl, heptynyl, octynyl, decynyl, and the like.

"Alkynylenyl" refers to a divalent group derived by the removal of two hydrogen atoms from a straight or branched chain acyclic hydrocarbon group containing a carbon-carbon triple bond. Representative alkynylenyl include

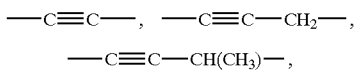

and the like.

"Alkynyloxy" means an alkynyl-O— group wherein the alkynyl group is defined herein. Representative alkynyloxy groups include propynyloxy, 3-butynyloxy, and the like.

"Alkynyloxyalkylenyl" means alkyny-O-alkylenyl-group wherein alkynyl and alkylenyl are defined herein.

"Amidino" or "amidine" means a group of formula

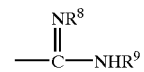

wherein $R^8$ is selected from hydrogen; $R^{10}O_2C$— (wherein $R^{10}$ is hydrogen, alkyl, aralkyl or heteroaralkyl); $R^{10}O$—; $R^{10}C(O)$—; (wherein $R^{10}$ is hydrogen, alkyl, aralkyl or heteroaralkyl); cyano; alkyl; nitro; and amino, and $R^9$ is selected from hydrogen; alkyl; aralkyl; and heteroaralkyl.

"Amino" means a group of formula $Y^1Y^2N$— wherein $Y^1$ and $Y^2$ are independently hydrogen; acyl; or alkyl, or $Y^1$ and $Y^2$ taken together with the N through which $Y^1$ and $Y^2$ are linked form a 4 to 7 membered azaheterocyclyl or azaheterocyclenyl. Representative amino groups include amino ($H_2N$—), methylamino, dimethylamino, diethylamino, and the like.

"Aminoalkylenyl" means an amino-alkylenyl-group wherein amino and alkylenyl are defined herein. Representative aminoalkylenyl groups include aminomethyl, aminoethyl, dimethylaminomethyl, and the like.

"Aralkenyl" means an aryl-alkenylenyl-group wherein aryl and alkenylenyl are define herein. Preferred aralkenyls contain a lower alkenyl moiety. A representative aralkenyl group is 2-phenethenyl.

"Aralkyloxy" means an aralkyl-O— group wherein aralkyl is defined herein. Representative aralkoxy groups include benzyloxy, naphth-1-ylmethoxy, naphth-2-ylmethoxy, and the like.

"Aralkyloxyalkylenyl" means an aralkyl-O-alkylenyl-group wherein aralkyl and alkylenyl are defined herein. A representative aralkoxyalkylenyl group is benzyloxyethyl.

"Aralkyloxycarbonyl" means an aralkyl-O—CO— group wherein aralkyl is defined herein. A representative aralkoxycarbonyl group is benzyloxycarbonyl.

"Aralkyloxycarbonylalkyl" means an aralkoxycarbonyl group attached to the parent molecular moiety through an alkylene. Representative aralkoxycarbonylalkyls include benzyloxycarbonylmethyl, benzyloxycarbonylethyl.

"Aralkyl" means an aryl-alkylenyl-. Preferred aralkyls contain a lower alkyl moiety. Representative aralkyl groups include benzyl, 2-phenethyl, naphthlenemethyl, and the like.

"Aralkyloxyalkenylenyl" means an aralkyl-O-alkenylenyl-group wherein aralkyl and alkenylenyl are defined herein. A representative aralkyloxyalkenylenyl group is 3-benzyloxyallyl.

"Aralkylsulfonyl" means an aralkyl-SO$_2$— group wherein aralkyl is defined herein.

"Aralkylsulfinyl" means an aralkyl-SO— group wherein aralkyl is defined herein.

"Aralkylthio" means an aralkyl-S— group wherein aralkyl is defined herein. A representative aralkylthio group is benzylthio.

"Aroyl" means an aryl-CO— group wherein aryl is defined herein. Representative aroyl include benzoyl, naphth-1-oyl and naphth-2-oyl.

"Aryl" means an aromatic monocyclic or multicyclic ring system of 6 to about 14 carbon atoms, preferably of about 6 to about 10 carbon atoms. The aryl is optionally substituted with one or more "ring system substituents" which may be the same or different, and are as defined herein. Representative aryl groups include phenyl and naphthyl.

"Aralkynyl" means an aryl-alkynylenyl-group wherein aryl and alkynylenyl are defined herein. Representative aralkynyl groups include phenylacetylenyl and 3-phenylbut-2-ynyl.

"Aryldiazo" means an aryl-N=N— group wherein aryl is defined herein. Representative aryldiazo groups include phenyldiazo and naphthyldiazo.

"Arylcarbamoyl" means an aryl-NHCO— group, wherein aryl is defined herein.

"Carbamyl" means a group of formula $Y^1 Y^2NCO$— wherein $Y^1$ and $Y^2$ are defined herein. Representative carbamyl groups include carbamyl ($H_2NCO$—), dimethylaminocarbamoyl ($Me_2NCO$—), and the like.

"Fused arylcycloalkenyl" means a radical derived from a fused aryl and cycloalkenyl as defined herein by removal of hydrogen atom from the cycloalkenyl portion. Preferred fused arylcycloalkenyls are those wherein aryl is phenyl and the cycloalkenyl consists of about 5 to about 6 ring atoms. The fused arylcycloalkenyl is optionally substituted by one or more ring system substituents, wherein "ring system substituent" is as defined herein. Representative fused arylcycloalkenyl include 1,2-dihydronaphthylene, indene, and the like, in which the bond to the parent moiety is through a non-aromatic carbon atom.

"Fused cycloalkenylaryl" means a radical derived from a fused arylcycloalkenyl as defined herein by removal of hydrogen atom from the aryl portion. Representative fused cycloalkenylaryl are as described herein for a fused arylcycloalkenyl, except that the bond to the parent moiety is through an aromatic carbon atom.

"Fused arylcycloalkyl" means a radical derived from a fused aryl and cycloalkyl as defined herein by removal of a hydrogen atom from the cycloalkyl portion. Preferred fused arylcycloalkyls are those wherein aryl is phenyl and the cycloalkyl consists of about 5 to about 6 ring atoms. The fused arylcycloalkyl is optionally substituted by one or more ring system-substituents, wherein "ring system substituent" is as defined herein. Representative fused arylcycloalkyl includes 1,2,3,4-tetrahydronaphthyl, and the like, in which the bond to the parent moiety is through a non-aromatic carbon atom.

"Fused cycloalkylaryl" means a radical derived from a fused arylcycloalkyl as defined herein by removal of a hydrogen atom from the aryl portion. Representative fused cycloalkylaryl are as described herein for a fused arylcycloalkyl radical, except that the bond to the parent moiety is through an aromatic carbon atom.

"Fused arylheterocyclenyl" means a radical derived from a fused aryl and heterocyclenyl as defined herein by removal of a hydrogen atom from the heterocyclenyl portion. Preferred fused arylheterocyclenyls are those wherein aryl is phenyl and the heterocyclenyl consists of about 5 to about 6 ring atoms. The prefix aza, oxa or thia before the heterocyclenyl portion of the fused arylheterocyclenyl means that at least a nitrogen, oxygen or sulfur atom respectively is present as a ring atom. The fused arylheterocyclenyl is optionally substituted by one or more ring system substituents, wherein "ring system substituent" is as defined herein. The nitrogen or sulphur atom of the heterocyclenyl portion of the fused arylheterocyclenyl is optionally oxidized to the corresponding N-oxide, S-oxide or S,S-dioxide. Representative fused arylheterocyclenyl include 3H-indolinyl, 1H-2-oxoquinolyl, 2H-1-oxoisoquinolyl, 1,2-dihydroquinolinyl, 3,4-dihydroquinolinyl, 1,2-dihydroisoquinolinyl, 3,4-dihydroisoquinolinyl, and the like, in which the bond to the parent moiety is through a non-aromatic carbon or nitrogen atom capable of such.

"Fused heterocyclenylaryl" means a radical derived from a fused arylheterocyclenyl as defined herein by removal of a hydrogen atom from the aryl portion. Representative fused heterocyclenylaryl are as defined herein for a fused arylheterocyclenyl radical, except that the bond to the parent moiety is through an aromatic carbon atom.

"Fused arylheterocyclyl" means a radical derived from a fused aryl and heterocyclyl as defined herein by removal of a hydrogen atom from the heterocyclyl portion. Preferred fused arylheterocyclyls are those wherein aryl is phenyl and the heterocyclyl consists of about 5 to about 6 ring atoms. The prefix aza, oxa or thia before heterocyclyl means that at least a nitrogen, oxygen or sulfur atom respectively is present as a ring atom. The fused arylheterocyclyl is optionally substituted by one or more ring system substituents, wherein "ring system substituent" is as defined herein. The nitrogen or sulphur atom of the heterocyclyl portion of the fused arylheterocyclyl is optionally oxidized to the corresponding N-oxide, S-oxide or S,S-dioxide. Representative preferred fused arylheterocyl ring systems include indolinyl, 1,2,3,4-tetrahydroisoquinoline, 1,2,3,4-tetrahydroquinoline, 1H-2,3-dihydroisoindolyl, 2,3-dihydrobenz[f]isoindolyl, 1,2,3,4-tetrahydrobenz[g]isoquinolinyl, and the like, in which the bond to the parent moiety is through a non-aromatic carbon or nitrogen atom.

"Fused heterocyclylaryl" means a radical derived from a fused aryiheterocyclyl as defined herein by removal of a hydrogen atom from the heterocyclyl portion. Representative preferred fused heterocyclylaryl ring systems are as described for fused arylheterocyclyl, except that the bond to the parent moiety is through an aromatic carbon atom.

"Carboxy" means a HO(O)C— group (i.e. a carboxylic acid).

"Carboxyalkyl" means a $HO_2C$-alkylenyl-group wherein alkylenyl is defined herein. Representative carboxyalkyls include carboxymethyl and carboxyethyl.

"Cycloalkyloxy" means a cycloalkyl-O— group wherein cycloalkyl is defined herein. Representative cycloalkyloxy groups include cyclopentyloxy, cyclohexyloxy, and the like.

"Cycloalkyl" means a non-aromatic mono- or multicyclic ring system of about 3 to about 10 carbon atoms, preferably of about 5 to about 10 carbon atoms. Preferred cycloalkyl rings contain about 5 to about 6 ring atoms. The cycloalkyl is optionally substituted with one or more "ring system substituents" which may be the same or different, and are as defined herein. Representative monocyclic cycloalkyl include cyclopentyl, cyclohexyl, cycloheptyl, and the like. Representative multicyclic cycloalkyl include 1-decalin, norbornyl, adamantyl, and the like.

"Cycloalkenyl" means a non-aromatic mono- or multicyclic ring system of about 3 to about 10 carbon atoms, preferably of about 5 to about 10 carbon atoms which contains at least one carbon-carbon double bond. Preferred cycloalkylene rings contain about 5 to about 6 ring atoms. The cycloalkenyl is optionally substituted with one or more "ring system substituents" which may be the same or different, and are as defined herein. Representative monocyclic cycloalkenyl include cyclopentenyl, cyclohexenyl, cycloheptenyl, and the like. A representative multicyclic cycloalkenyl is norbornylenyl.

"Cycloalkylenyl" means a bivalent, saturated carbocyclic group having about 4 to about 8 carbon atoms. Preferred cycloalkylenyl groups include 1,2-, 1,3-, or 1,4-cis or trans-cyclohexanylene.

"Diazo" means a bivalent —N=N— radical.

"Chemical bond" means a direct bond.

"Ethylenyl" means a —CH=CH— group.

"Halo" or "halogen" mean fluoro, chloro, bromo, or iodo.

"Heteroaralkenyl" means a heteroaryl-alkenylenyl-group wherein heteroaryl and alkenylenyl are defined herein. Preferred heteroaralkenyls contain a lower alkenylene moiety.

Representative heteroaralkenyl groups include 4-pyridylvinyl, thienylethenyl, pyridylethenyl, imidazolylethenyl, pyrazinylethenyl, and the like.

"Heteroaralkyl" means a heteroaryl-alkylenyl-group wherein heteroaryl and alkylenyl are defined herein. Preferred heteroaralkyls contain a lower alkylenyl group. Representative heteroaralkyl groups include thienylmethyl, pyridylmethyl, imidazolylmethyl, pyrazinylmethyl, and the like.

"Heteroaralkyloxy" means an heteroaralkyl-O— group wherein heteroaralkyl is defined herein. A representative heteroaralkyloxy group is 4-pyridylmethyloxy.

"Heteroaralkyloxyalkenyl" means a heteroaralkyl-O-alkenylenyl-group wherein heteroaralkyl and alkenylenyl are defined herein. A representative heteroaralkyloxyalkenyl group is 4-pyridylmethyloxyallyl.

"Heteroaralkyloxyalkyl" means a heteroaralkyl-O-alkylene-group wherein heteroaralkyl and alkylene are defined herein. A representative heteroaralkyloxy group is 4-pyridylmethyloxyethyl.

"Heteroaralkynyl" means an heteroaryl-alkynylene-group wherein heteroaryl and alkynylene are defined herein. Preferred heteroaralkynyls contain a lower alkynylene moiety. Representative heteroaralkynyl groups include pyrid-3-ylacetylenyl, quinolin-3-ylacetylenyl, 4-pyridylethynyl, and the like.

"Heteroaroyl" means an means a heteroaryl-CO— group wherein heteroaryl is defined herein. Representative heteroaroyl groups include thiophenoyl, nicotinoyl, pyrrol-2-ylcarbonyl, pyridinoyl, and the like.

"Heteroaryl" means an aromatic monocyclic or multicyclic ring system of about 5 to about 14 ring atoms, preferably about 5 to about 10 ring atoms, in which one or more of the atoms in the ring system is/are element(s) other than carbon, for example nitrogen, oxygen or sulfur. Preferred heteroaryls contain about 5 to about 6 ring atoms. The "heteroaryl" may also be substituted by one or more "ring system substituents" which may be the same or different, and are as defined herein. The prefix aza, oxa or thia before heteroaryl means that at least a nitrogen, oxygen or sulfur atom respectively is present as a ring atom. A nitrogen atom of a heteroaryl may be oxidized to the corresponding N-oxide. Representative heteroaryls include pyrazinyl, furanyl, thienyl, pyridyl, pyrimidinyl, isoxazolyl, isothiazolyl, oxazolyl, thiazolyl, pyrazolyl, furazanyl, pyrrolyl, pyrazolyl, triazolyl, 1,2,4-thiadiazolyl, pyridazinyl, quinoxalinyl, phthalazinyl, imidazo[1,2-a]pyridine, imidazo[2,1-b]thiazolyl, benzofurazanyl, indolyl, azaindolyl, benzimidazolyl, benzothienyl, quinolinyl, imidazolyl, thienopyridyl, quinazolinyl, thienopyrimidyl, pyrrolopyridyl, imidazopyridyl, isoquinolinyl, benzoazaindolyl, or 1,2,4-triazinyl.

"Heteroaryidiazo" means an heteroaryl-N=N— group wherein heteroaryl is as defined herein.

"Fused heteroarylcycloalkenyl" means a radical derived from a fused heteroaryl and cycloalkenyl as defined herein by removal of a hydrogen atom from the cycloalkenyl portion. Preferred fused heteroarylcycloalkenyls are those wherein the heteroaryl and the cycloalkenyl each contain about 5 to about 6 ring atoms. The prefix aza, oxa or thia before heteroaryl means that at least a nitrogen, oxygen or sulfur atom respectively is present as a ring atom. The fused heteroarylcycloalkenyl is optionally substituted by one or more ring system substituents, wherein "ring system substituent" is as defined herein. The nitrogen atom of the heteroaryl portion of the fused heteroarylcycloalkenyl is optionally oxidized to the corresponding N-oxide. Representative fused heteroarylcycloalkenyl include 5,6-dihydroquinolyl, 5,6-dihydroisoquinolyl, 5,6-dihydroquinoxalinyl, 5,6-dihydroquinazolinyl, 4,5-dihydro-1H-benzimidazolyl, 4,5-dihydrobenzoxazolyl, and the like, in which the bond to the parent moiety is through a non-aromatic carbon atom.

"Fused cycloalkenylheteroaryl" means a radical derived from a fused heteroarylcycloalkenyl as defined herein by removal of a hydrogen atom from the heteroaryl portion. Representative fused cycloalkenylheteroaryl are as described herein for fused heteroarylcycloalkenyl, except that the bond to the parent moiety is through an aromatic carbon atom.

"Fused heteroarylcycloalkyl" means a radical derived from a fused heteroaryl and cycloalkyl as defined herein by removal of a hydrogen atom from the cycloalkyl portion. Preferred fused heteroarylcycloalkyls are those wherein the heteroaryl thereof consists of about 5 to about 6 ring atoms and the cycloalkyl consists of about 5 to about 6 ring atoms. The prefix aza, oxa or thia before heteroaryl means that at least a nitrogen, oxygen or sulfur atom is present respectively as a ring atom. The fused heteroarylcycloalkyl is optionally substituted by one or more ring system substituents, wherein "ring system substituent" is as defined herein. The nitrogen atom of the heteroaryl portion of the fused heteroarylcycloalkyl is optionally oxidized to the corresponding N-oxide. Representative fused heteroarylcycloalkyl include 5,6,7,8-tetrahydroquinolinyl, 5,6,7,8-tetrahydroisoquinolyl, 5,6,7,8-tetrahydroquinoxalinyl, 5,6,7,8-tetrahydroquinazolyl, 4,5,6,7-tetrahydro-1H-benzimidazolyl, 4,5,6,7-tetrahydrobenzoxazolyl, 1H-4-oxa-1,5-diazanaphthalen-2-onyl, 1,3-dihydroimidizole-[4,5]-pyridin-2-onyl, and the like, in which the bond to the parent moiety is through a non-aromatic carbon atom.

"Fused cycloalkylheteroaryl" means a radical derived from a fused heteroarylcycloalkyl as defined herein by removal of a hydrogen atom from the heteroaryl portion. Representative fused cycloalkylheteroaryl are as described herein for fused heteroarylcycloalkyl, except that the bond to the parent moiety is through an aromatic carbon atom.

"Fused heteroarylheterocyclenyl" means a radical derived from a fused heteroaryl and heterocyclenyl as defined herein by the removal of a hydrogen atom from the heterocyclenyl portion. Preferred fused heteroarylheterocyclenyls are those wherein the heteroaryl thereof consists of about 5 to about 6 ring atoms and the heterocyclenyl consists of about 5 to about 6 ring atoms. The prefix aza, oxa or thia before heteroaryl or heterocyclenyl means that at least a nitrogen, oxygen or sulfur atom is present respectively as a ring atom. The fused heteroarylheterocyclenyl is optionally substituted by one or more ring system substituents, wherein "ring system substituent" is as defined herein. The nitrogen atom of the heteroaryl portion of the fused heteroarylheterocyclenyl is optionally oxidized to the corresponding N-oxide. The nitrogen or sulphur atom of the heterocyclenyl portion of the fused heteroarylheterocyclenyl is optionally oxidized to the corresponding N-oxide, S-oxide or S,S-dioxide. Representative fused heteroarylheterocyclenyl include 7,8-dihydro[1,7]naphthyridinyl, 1,2-dihydro[2,7]naphthyridinyl, 6,7-dihydro-3H-imidazo[4,5-c]pyridyl, 1,2-dihydro-1,5-naphthyridinyl, 1,2-dihydro-1,6-naphthyridinyl, 1,2-dihydro-1,7-naphthyridinyl, 1,2-dihydro-1,8-naphthyridinyl, 1,2-dihydro-2,6-naphthyridinyl, and the like, in which the bond to the parent moiety is through a non aromatic carbon or nitrogen atom.

"Fused heterocyclenylheteroaryl" means a radical derived from a fused heteroarylheterocyclenyl as defined herein by the removal of a hydrogen atom from the heteroaryl portion. Representative fused heterocyclenylheteroaryl are as described herein for fused heteroarylheterocyclenyl, except that the bond to the parent moiety is through an aromatic carbon or nitrogen atom.

"Fused heteroarylheterocyclyl" means a radical derived from a fused heteroaryl and heterocyclyl as defined herein, by removal of a hydrogen atom from the heterocyclyl portion. Preferred fused heteroarylheterocyclyls are those wherein the heteroaryl thereof consists of about 5 to about 6 ring atoms and the heterocyclyl consists of about 5 to about 6 ring atoms. The prefix aza, oxa or thia before the heteroaryl or heterocyclyl portion of the fused heteroarylheterocyclyl means that at least a nitrogen, oxygen or sulfur atom respectively is present as a ring atom. The fused heteroarylheterocyclyl is optionally substituted by one or more ring system substituents, wherein "ring system substituent" is as defined herein. The nitrogen atom of the heteroary portion of the fused heteroarylheterocyclyl is optionally oxidized to the corresponding N-oxide. The nitrogen or sulphur atom of the heterocyclyl portion of the fused heteroarylheterocyclyl is optionally oxidized to the corresponding N-oxide, S-oxide or S,S-dioxide. Representative fused heteroarylheterocyclyl include 2,3-dihydro-1H pyrrol [3,4-b]quinolin-2-yl, 1,2,3,4-tetrahydrobenz [b][1,7] naphthyridin-2-yl, 1,2,3,4-tetrahydrobenz [b][1,6] naphthyridin-2-yl, 1,2,3,4-tetrahydro-9H-pyrido[3,4-b]indol-2yl, 1,2,3,4-tetrahydro-9H-pyrido[4,3-b]indol-2yl 2,3,-dihydro-1H-pyrrolo[3,4-b]indol-2-yl, 1H-2,3,4,5-tetrahydroazepino[3,4-b]indol-2-yl, 1H-2,3,4,5-tetrahydroazepino[4,3-b]indol-3-yl, 1H-2,3,4,5-tetrahydroazepino[4,5-b]indol-2 yl, 5,6,7,8-tetrahydro[1,7]napthyridinyl, 1,2,3,4-tetrhydro[2,7]naphthyridyl, 2,3-dihydro[1,4]dioxino[2,3-b]pyridyl, 2,3-dihydro[1,4]dioxino[2,3-b]pryidyl, 3,4-dihydro-2H-1-oxa[4,6]diazanaphthalenyl, 4,5,6,7-tetrahydro-3H-imidazo[4,5-c]pyridyl, 6,7-dihydro[5,8]diazanaphthalenyl, 1,2,3,4-tetrahydro[1,5]naphthyridinyl, 1,2,3,4-tetrahydro[1,6]naphthyridinyl, 1,2,3,4-tetrahydro[1,7]naphthyridinyl, 1,2,3,4-tetrahydro[1,8]naphthyridinyl, 1,2,3,4-tetrahydro[2,6]naphthyridinyl, and the like, in which the bond to the parent moiety is through a non-aromatic carbon or nitrogen atom.

"Fused heterocyclylheteroaryl" means a radical derived from a fused heteroarylheterocyclyl as defined herein, by removal of a hydrogen atom from the heteroaryl portion. Representative fused heterocyclylheteroaryl are as described herein for fused heterarylheterocyclyl, except that the bond to the parent moiety is through an aromatic carbon atom.

"Heteroarylsulphonylcarbamoyl" means a heteroaryl-SO$_2$—NH—CO— group wherein heteroaryl is defined herein.

"Heterocyclenyl" means a non-aromatic monocyclic or multicyclic ring system of about 3 to about 10 ring atoms, preferably about 5 to about 10 ring atoms, in which one or more of the atoms in the ring system is/are element(s) other than carbon, for example nitrogen, oxygen or sulfur atoms, and which contains at least one carbon-carbon double bond or carbon-nitrogen double bond. Preferred heterocyclenyl rings contain about 5 to about 6 ring atoms. The prefix aza, oxa or thia before heterocyclenyl means that at least a nitrogen, oxygen or sulfur atom respectively is present as a ring atom. The heterocyclenyl may be optionally substituted by one or more ring system substituents, wherein "ring system substituent" is as defined herein. The nitrogen or sulphur atom of the heterocyclenyl is optionally oxidized to the corresponding N-oxide, S-oxide or S,S-dioxide. Representative monocyclic azaheterocyclenyl groups include 1,2, 3,4-tetrahydropyridine, 1,2-dihydropyridyl, 1,4-dihydropyridyl, 1,2,3,6-tetrahydropyridine, 1,4,5,6-tetrahydropyrimidine, 2-pyrrolinyl, 3-pyrrolinyl, 2-imidazolinyl, 2-pyrazolinyl, and the like. Representative oxaheterocyclenyl groups include 3,4-dihydro-2H-pyran, dihydrofuranyl, fluorodihydrofuranyl, and the like. A representative multicyclic oxaheterocyclenyl group is 7-oxabicyclo[2.2.1]heptenyl. Representative monocyclic thiaheterocyclenyl rings include dihydrothiophenyl, dihydrothiopyranyl, and the like "Heterocyclyl" means a non-aromatic saturated monocyclic or multicyclic ring system of about 3 to about 10 ring atoms, preferably about 5 to about 10 ring atoms, in which one or more of the atoms in the ring system is/are element(s) other than carbon, for example nitrogen, oxygen or sulfur. Preferred heterocyclyls contain about 5 to about 6 ring atoms. The prefix aza, oxa or thia before heterocyclyl means that at least a nitrogen, oxygen or sulfur atom respectively is present as a ring atom. The heterocyclyl is optionally substituted by one or more "ring system substituents" which may be the same or different, and are as defined herein. The nitrogen or sulphur atom of the heterocyclyl is optionally oxidized to the corresponding N-oxide, S-oxide or S,S-dioxide. Representative monocyclic heterocyclyl rings include 1,3-dioxolanyl, 1,4-dioxanyl, tetrahydrofuranyl, tetrahydrothiophenyl, tetrahydrothiopyranyl, and the like. Representative monocyclic azaheterocyclyl rings include piperidyl, pyrrolidinyl, piperazinyl, morpholinyl, thiomorpholinyl, thiazolidinyl and the like.

"Heterocyclylalkyl" means a heterocyclyl-alkylene-group wherein heterocyclyl and alkylene are defined herein. Preferred heterocyclylalkyls contain a lower alkylene moiety. A representative heteroaralkyl group is tetrahydropyranylmethyl.

"Heterocyclylalkyloxyalkyl" means a heterocyclylalkyl-O-alkylene group wherein heterocyclylalkyl and alkylene are defined herein. A representative heterocyclylalkyloxyalkyl group is tetrahydropyranylmethyloxymethyl.

"Heterocyclyloxy" means a heterocyclyl-O— group wherein heterocyclyl is defined herein. Representative heterocyclyloxy groups include quinuclidyloxy, pentamethylenesulfideoxy, tetrahydropyranyloxy, tetrahydrothiophenyloxy, pyrrolidinyloxy, tetrahydrofuranyloxy, 7-oxabicyclo[2.2.1]heptanyloxy, hydroxytetrahydropyranyloxy, hydroxy-7-oxabicyclo[2.2.1]heptanyloxy, and the like.

"Hydroxyalkyl" means an alkyl group as defined herein substituted with one or more hydroxy groups. Preferred hydroxyalkyls contain lower alkyl. Representative hydroxyalkyl groups include hydroxymethyl and 2-hydroxyethyl.

"N-oxide" means a

group.

"Phenoxy" means a phenyl-O— group wherein the phenyl ring is optionally substituted with one or more ring system substituents as defined herein.

"Phenylene" means a -phenyl-group wherein the phenyl ring is optionally substituted with one or more ring system substituents as defined herein.

"Phenylthio" means a phenyl-S— group wherein the phenyl ring is optionally substituted with one or more ring system substituents as defined herein.

"Pyridyloxy" means a pyridyl-O— group wherein the pyridyl ring is optionally substituted with one or more ring system substituents as defined herein.

"Ring system substituents" mean substituents attached to aromatic or non-aromatic ring systems inclusive of hydrogen, alkyl, aralkyl, heteroaryl, aryl, heteroaralkyl, hydroxy, hydroxyalkyl, alkoxy, aryloxy, aralkoxy, acyl, aroyl, halo, nitro, cyano, formyl, carboxy, alkoxycarbonyl, aryloxycarbonyl, aralkoxycarbonyl, alkylsulfonyl, arylsulfonyl, heteroarylsulfonyl, alkylsulfinyl, arylsulfinyl, nitrile, $NO_2$, heteroarylsulfinyl, alkylthio, arylthio, heteroarylthio, aralkylthio, heteroaralkylthio, cycloalkyl, cycloalkenyl, heterocyclyl, heterocyclenyl, aryidiazo, heteroaryldiazo, amidino, amino, aminoalkyl, carbamyl and sulfamyl. When a ring system is saturated or partially saturated, the "ring system substituent" further comprises methylene ($H_2C=$), oxo ($O=$) and thioxo ($S=$). Preferred ring system substituents are hydrogen, $CF_3$, fluoro, alkyl, alkoxy, nitrile or $NO_2$.

"Sulfamyl" means a group of formula $Y^1Y^2NSO_2$— wherein $Y^1$ and $Y^2$ are defined herein. Representative sulfamyl groups are aminosulfamoyl ($H_2NSO_2$—) and dimethylaminosulfamoyl ($Me_2NSO_2$—).

PREFERRED EMBODIMENTS

The preparation of the fluorophenyl resin compound of formula

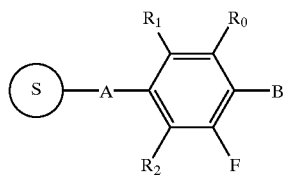

wherein A is —YC(O)— and B is —OH is shown in Scheme 1.

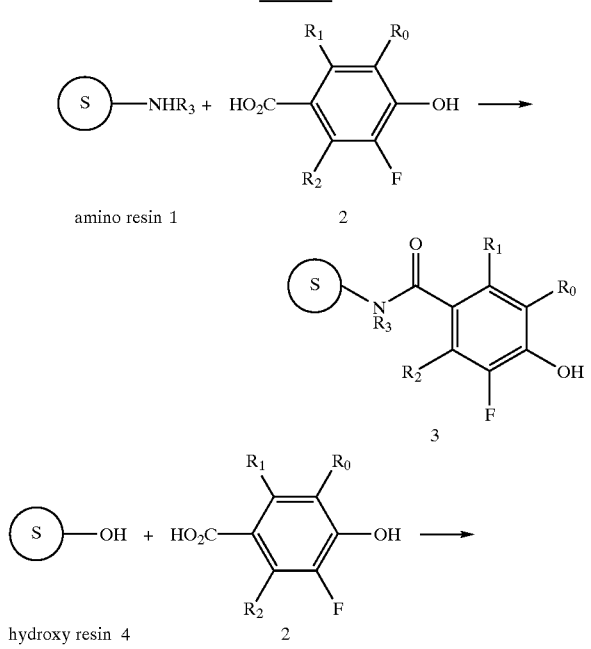

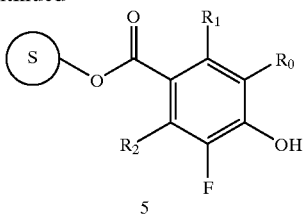

, $R_1$, $R_2$, and $R_3$ are as defined herein

According to the foregoing Scheme 1, amino resin 1 or hydroxy resin 4 is coupled with the 4-hydroxyfluorobenzoic acid derivative 2 in a suitable organic solvent such as dichloromethane, DMF, DMSO or THF to form the 4-hydroxyfluorobenzamido resin compound 3 or 4-hydroxyfluorobenzoyloxy resin compound 5. Coupling times range from about 2 to about 24 hours, depending upon the amino resin and 4-hydroxyfluorobenzoic acid derivative to be coupled, activating agent, solvent and temperature. The coupling is accomplished at from about −10° C. to about 50° C., preferably at about ambient temperature. The carboxylic acid moiety is activated with an appropriate activating agent (for a list of activating agents, with specific references, see Arrieta et al., Synn. Commun. 13, 471, 1983) such as isopropyl chloroformate in the presence of N-methylmorpholine, diisopropylcarbodiimide (DIC) in the presence of 1-hydroxybenzotriazole (HOBT), diisopropylcarbodiimide (DIC) in the presence of 4-dimethylaminopyridine. (DMAP), bis(2-oxo-3-oxazolidinyl)-phosphonic chloride (BOP-Cl) in the presence of triethylamine, bromotripyrrolidinophosphonium hexafluorophosphate (PyBrop™) in the presence of triethylamine (TEA), 2-(1H-benzotriazole-1-yl)-1,1,3,3-tetramethyluronium tetrafluoroborate (TBTU) in the presence of diisopropylethyl amine, N-hydroxysuccinimide in the presence of N,N'-dicyclohexylcarbodiimide (DCC), pyridinium salts-$Bu_3N$, phenyl dichlorophosphate $PhOPOCl_2$, 2-chloro-1,3,5-trinitrobenzene and pyridine, polyphosphate ester, chlorosulfonyl isocyanate $ClSO_2NCO$, chlorosilane, $MeSO_2Cl$-$Et_3N$, $PH_3P$—$CCl_4$-$Et_3N$, and the like.

A preferred amino resin 1 for preparing the 4-hydroxyfluorobenzamido resins of this invention is aminomethyl polystyrene. Depending on the size of the particles, (200 or 400 mesh), aminomethyl polystyrene has loading ranges of from about 0.5 to about 1.2 mmol/g and from about 0.1 to about 0.5 mmol/g, respectively.

A preferred hydroxy resin 4 is hydroxymethyl resin.

In a preferred method of preparing the 4-hydroxyfluorobenzamido resin 3, a mixture of the 4-hydroxyfluorobenzoic acid derivative 2, aminomethyl polystyrene, diisopropylcarbodiimide (DIC) and 4-dimethylaminopyridine (DMAP) in anhydrous DMF is stirred at about ambient temperature for about 18 hours. The 4-hydroxyfluorobenzamido resin 3 is then filtered, washed with one or more solvents and dried.

The preparation of the fluorophenyl resin compound of formula

47

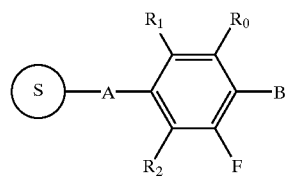

wherein A is

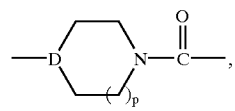

D is CH or N; $R_0$, $R_1$, and $R_2$ are as defined herein; P is 0, 1, or 2; and B is OH is shown in Scheme 2.

Scheme 2

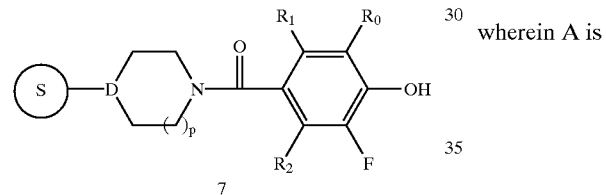

48

As shown in the Scheme 2 above, coupling of the azacycloalkyl resin compound 6 with the 4-hydroxyfluorobenzoic acid compound 2 provides the 4-hydroxyfluorobenzoyl-azacycloalkyl resin compound 7. The coupling is accomplished using the reagents and conditions described in Scheme 1 above. A preferred azacycloalkyl resin compound is (piperidinomethyl) polystyrene, designated herein as

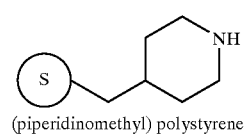

(piperidinormethyl) polystyrene

The preparation of the fluorophenyl resin compound of formula

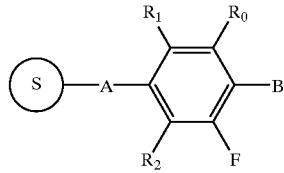

wherein A is

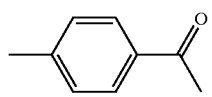

and B is F, OH, $SO_3H$ or $SO_2Cl$ is shown in Scheme 3.

Scheme 3

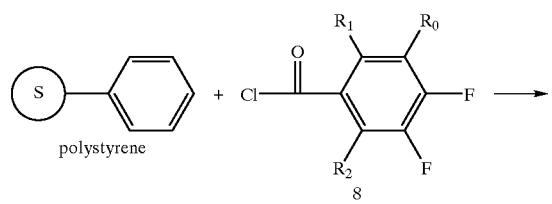

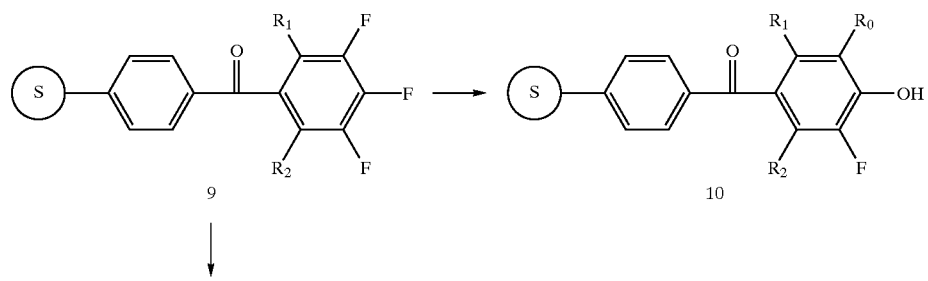

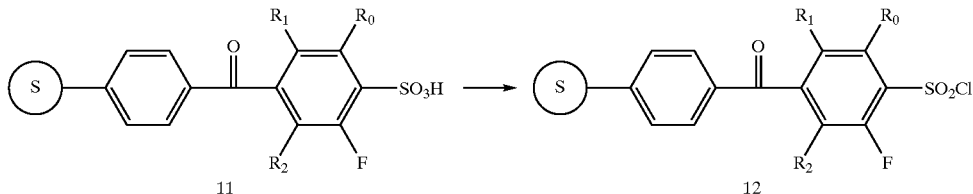

As shown in Scheme 3, Friedel-Crafts acylation of polystyrene with the 4-fluorofluorobenzoyl chloride derivative 8, in the presence of a Lewis acid such as FeCl$_3$, SnCl$_4$ or AlCl$_3$ in a suitable organic solvent provides the 4-fluorofluorobenzoyl resin compound 9. Reaction of 9 with hydroxide provides the 4-hydroxyfluorobenzoyl resin compound 10.

In a preferred aspect, polystyrene is acylated with the 4-fluorobenzoyl chloride derivative 8 in the presence of AlCl$_3$ in nitrobenzene to provide the 4-fluorobenzoyl resin compound 9. A mixture of 9 in water/cyclohexane is treated with sodium hydroxide and tetrabutylammonium hydrogen sulfate according to the procedure of Feldman et al., *J. Org. Chem.*, 56 (26), 7350–7354 (1991), to provide the 4-hydroxypolyfluorobenzoyl resin compound 10.

Reaction of the fluorobenzoyl resin compound 9 with an SO$_3^-$ equivalent such as potassium metabisulfite in the presence of base in a suitable organic solvent such as dichloromethane, dichloroethane or chloroform provides the fluorobenzoyl-4-sulfonic acid resin compound 11. Representative bases include diisopropylethylamine, pyridine, triethylamine, N-methylpiperidine, and the like. Reaction of the fluorobenzoyl-4-sulfonic acid resin compound 11 with an acid chloride including chlorosulfonic acid, thionyl chloride, oxalyl chloride, and the like, in an inert organic solvent provides the 5,6-trifluorobenzoyl-4-sulfonyl chloride acid resin compound 12.

The preparation of the fluorophenyl resin compound of formula

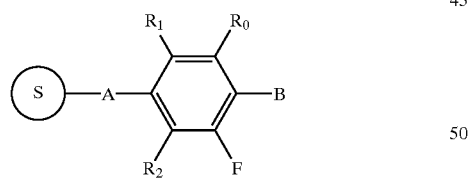

wherein A is —NR$_3$SO$_2$— and B is F or OH is outlined in Scheme 4.

Scheme 4

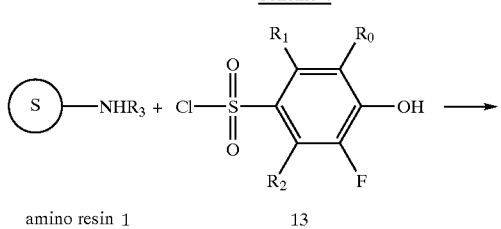

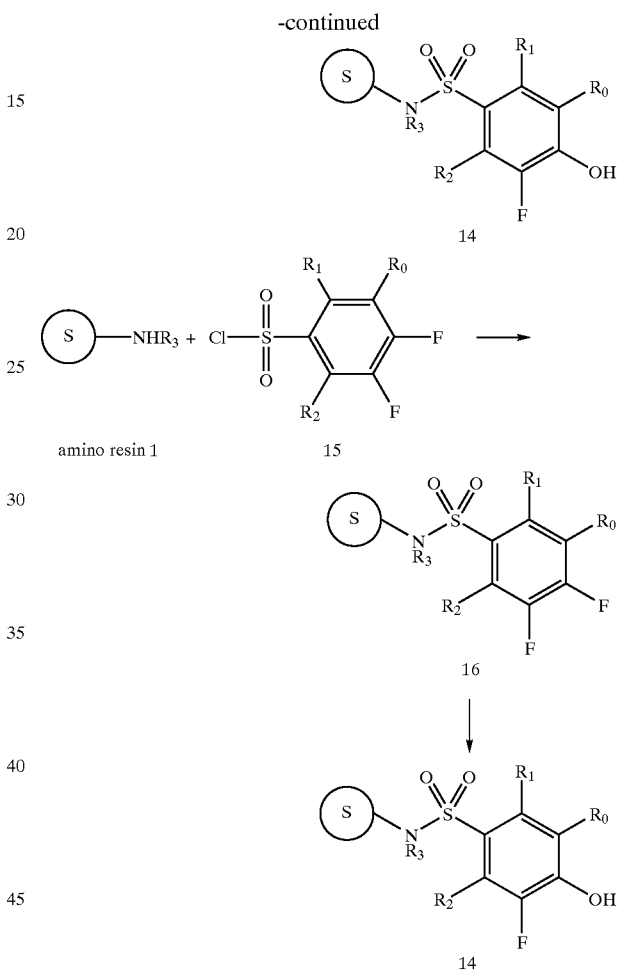

As shown in Scheme 4, reaction of amino resin 1 with the 4-hydroxyfluorophenylsulfonyl chloride compound 13 in the presence of base such as N-methylmorpholine, pyridine, collidine, triethylamine or diisopropylethylamine in a suitable organic solvent such as dichloromethane, dichloroethane, dioxane, THF or DMF, provides the 4-hydroxyfluorophenylsulfonamide resin compound 14. The reaction is preferably conducted in dichloromethane in the presence of collidine.

Alternatively, amino resin 1 is reacted with the 4-fluorofluorophenylsulfonyl chloride compound 15 as described above to give the 4-fluoro- fluorophenylsulfonamide resin compound 16 which is converted to the desired 4-hydroxyfluorophenylsulfonamide resin compound 14 under reaction conditions analogous to those described for the conversion of 9 to 10, as described in Scheme 3 above.

The preparation of the fluorophenyl resin compound of formula

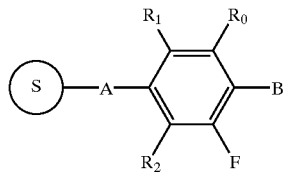

5 wherein A is —$C_6H_4$— and B is F, OH, $SO_3H$ or $SO_2Cl$ is shown in Scheme 5.

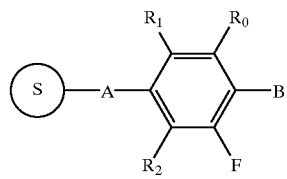

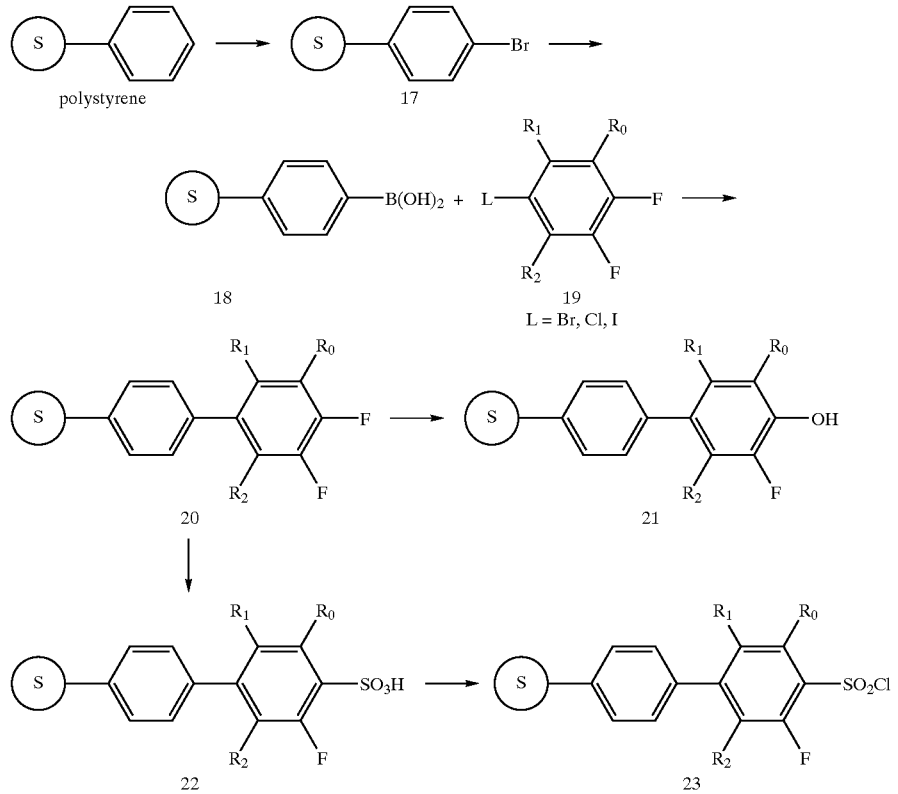

As shown in Scheme 5, bromination of polystyrene, for example using $Br_2$ in the presence of $FeCl_3$, $Tl(OAc)_3$ or $BF_3$ gives the brominated polystyrene resin compound 17. Metal halogen exchange, for example using an alkyllithium reagent such as n-butyllithium in benzene or TMEDA; addition of trimethylborate; and acidic workup provides the polystyryl boronic acid resin compound 18. Coupling of compound 18 with the fluorophenyl halide compound 19 using Suzuki conditions (catalytic Pd(0), basic conditions; See Frenette et al., *Tetrahedron Lett.*, 1994, 35, 9177 and Brown et al., *J. Amer. Chem. Soc.*, 1996, 118, 6331) provides the 4-fluorofluorophenyl polystyrene resin compound 20. Conversion of 20 to the 4-hydroxyfluorophenyl polystyrene resin compound 21, fluorophenyl-4-sulfonic acid polystyrene resin compound 22 or the fluorophenyl-4-sulfonyl chloride polystyrene resin compound 23 is accomplished under reaction conditions analogous to those described in Scheme 3 above.

The preparation of the fluorophenyl resin compound of formula wherein A is —$C_6H_4$—$SO_2$ and B is F or OH is outlined in Scheme 6 which describes the preparation of 4-hydroxy-polyfluorophenylsulfonyl-polystyrene resin. It is understood that the methodology described below may be readily adapted to the preparation of additional 4-hydroxyfluorophenylsulfonyl resin compounds.

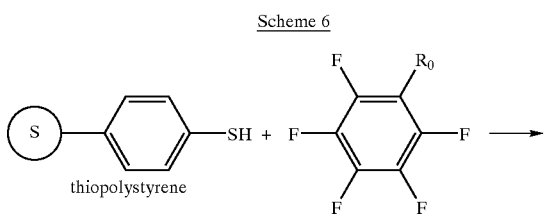

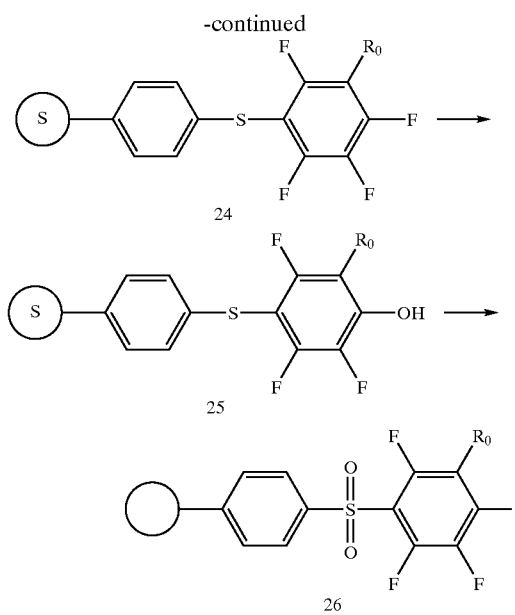

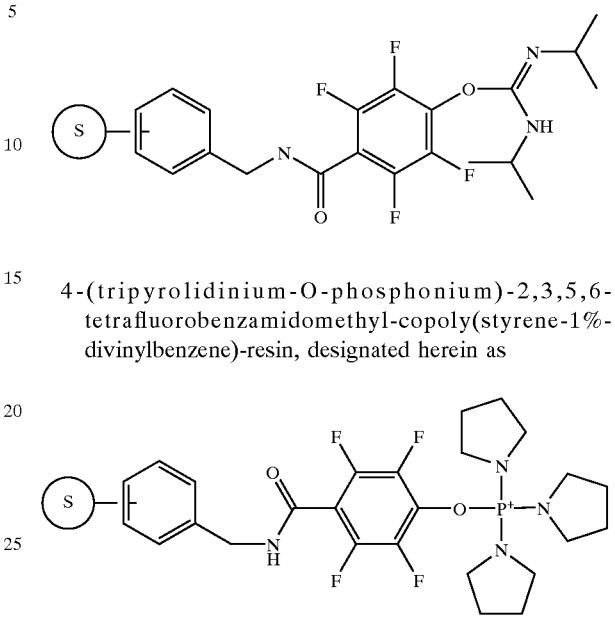

As shown in the foregoing Scheme 6, reaction of thiopolystyrene with hexafluorobenzene results in formation of the polyfluorophenylthio-polystyrene resin compound 24. The reaction is preferably carried out in a suitable solvent such as toluene, dioxane, DMF or DMSO, in the presence of base, preferably catalytic pyridine or N-methylmorpholine. Conversion of 24 to the 4-hydroxy-polyfluorophenylthio-polystyrene resin compound 25 is accomplished as described in Scheme 3 above. Oxidation of 25, for example using m-chloroperbenzoic acid (MCPBA) provides of 4-hydroxy-polyfluorophenylsulfonyl-polystyrene resin 26.

Preferred fluorophenyl resin compounds of this invention have formula I wherein $R_0$, $R_1$ and $R_2$ are independently nitro, monohaloalkyl, dihaloalkyl, trihaloalkyl (e.g., $CF_3$), bromo, chloro, fluoro, cyano, alkoxy, formyl, lower alkanoyl, lower alkylsulfonyl, lower alkylsulfinyl, and the like. Preferably, fluoro.

Preferred fluorophenyl resin compounds of this invention have formula I wherein $R_0$, $R_1$ and $R_2$ are F; $R_4$, $R_5$, $R_6$ and $R_7$ are H; and B is OH, $SO_3H$ or $SO_2Cl$.

Representative preferred fluorophenyl resin compounds include, but are not limited to:

4-hydroxy-2,3,5,6-tetrafluorobenzamidomethyl-polystyrene resin, designated herein as

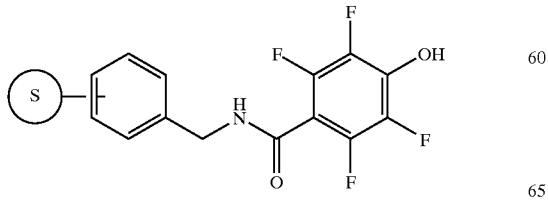

4-(N,N'-diisopropyl-isourea)-2,3,5,6-tetrafluorobenzamidomethyl-copoly(styrene-1%-divinylbenzene)-resin, designated herein as 4-(tripyrolidinium-O-phosphonium)-2,3,5,6-tetrafluorobenzamidomethyl-copoly(styrene-1%-divinylbenzene)-resin, designated herein as 2,3,5,6-tetrafluorobenzamidomethyl-4-sulfonic acid-polystyrene resin, designated herein as

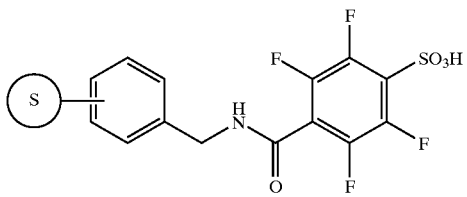

2,3,5,6-tetrafluorobenzamidomethyl-4-sulfonyl chloride-polystyrene resin, designated herein as

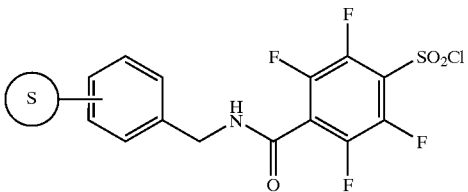

4-hydroxy-2,3,5,6-tetrafluornbenzoyloxymethyl-polystyrene resin, designated herein as

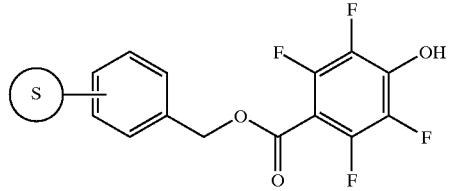

2,3,5,6-tetrafluorobenzoyloxymethyl-4-sulfonic acid-polystyrene resin, designated herein as

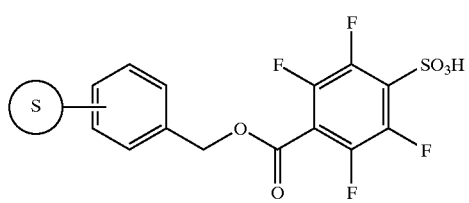

2,3,5,6-tetrafluorobenzoyloxymethyl-4-sulfonyl chloride-polystyrene resin, designated herein as

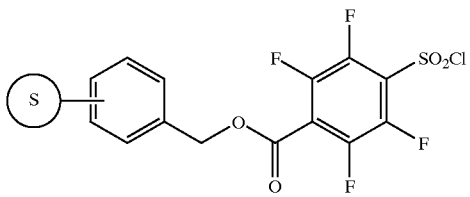

4-hydroxy-2,3,5,6-tetrafluorobenzoyl-polystyrene resin, designated herein as

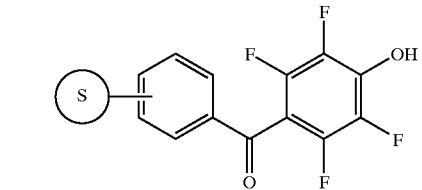

2,3,5,6-tetrafluorobenzoyl-4-sulfonic acid-polystyrene resin, designated herein as

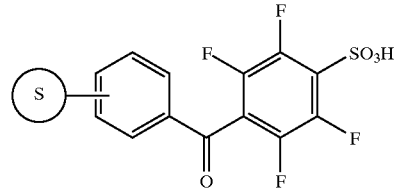

2,3,5,6-tetrafluorobenzoyl-4-sulfonyl chloride-polystyrene resin, designated herein as

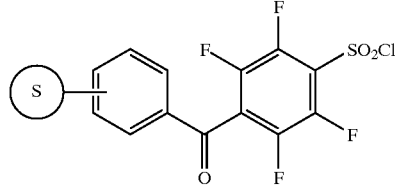

4-hydroxy-2,3,5,6-tetrafluorophenylsulfonamidomethyl-polystyrene resin, designated herein as

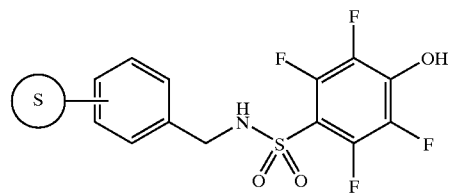

2,3,5,6-tetrafluorophenylsulfonamidomethyl-4-sulfonic acid-polystyrene resin, designated herein as

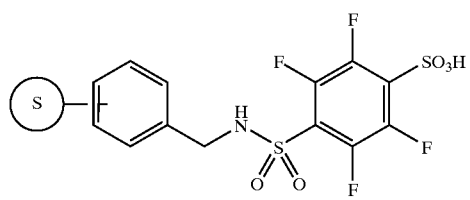

2,3,5,6-tetrafluorophenylsulfonamidomethyl-4-sulfonyl chloride-polystyrene resin, designated herein as

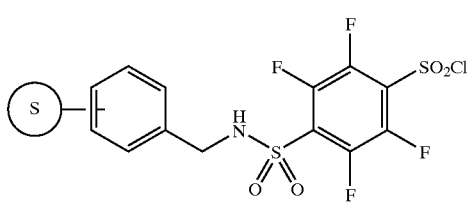

N-(4-hydroxy-2,3,5,6-tetrafluorobenzoyl)-piperidinomethyl-polystyrene resin, designated herein as

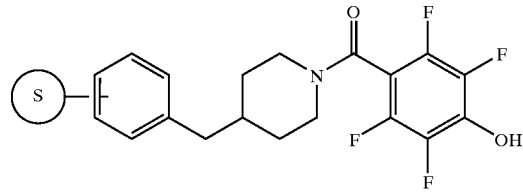

N-(2,3,5,6-tetrafluorobenzoyl-4-sulfonic acid)-piperidinomethyl-polystyrene resin, designated herein as

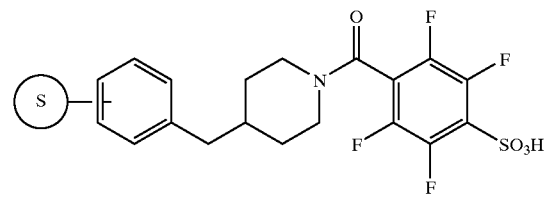

N-(2,3,5,6-tetrafluorobenzoyl-4-sulfonyl chloride)-piperidinomethyl-4-polystyrene resin, designated herein as

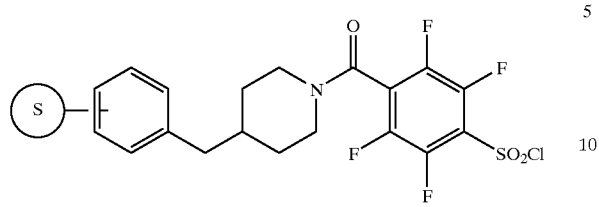

N-(4-hydroxy-2,3,5,6-tetrafluorophenylsulfonyl)-piperidinomethyl-polystyrene resin, designated herein as

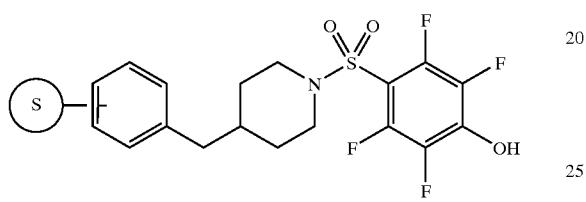

N-((2,3,5,6-tetrafluorophenyl-4-sulfonic acid)sulfonyl)-piperidinomethyl-polystyrene resin, designated herein as

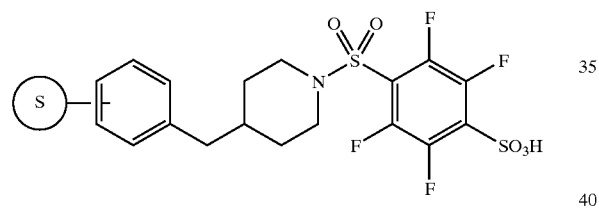

N-((2,3,5,6-tetrafluorophenyl-4-sulfonyl chloride)sulfonyl)-piperidinomethyl-polystyrene resin, designated herein as

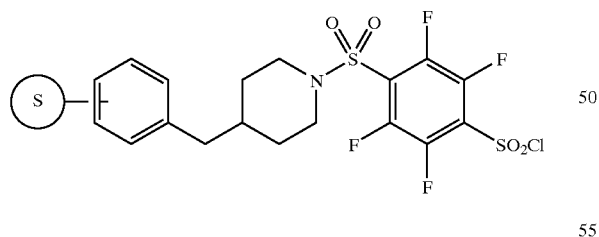

4-hydroxy-2,3,5,6-tetrafluorophenyl-polystyrene resin, designated herein as

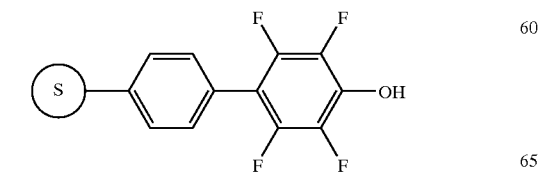

2,3,5,6-tetrafluorophenyl-4-sulfonic acid-polystyrene resin, designated herein as

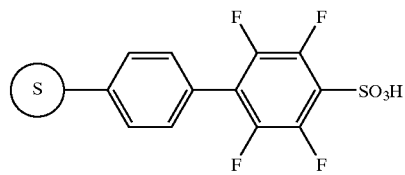

2,3,5,6-tetrafluorophenyl-4-sulfonyl chloride polystyrene resin, designated herein as

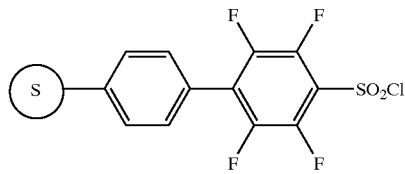

4-hydroxy-2,3,5,6-tetrafluorophenylsulfonyl-polystyrene resin, designated herein as

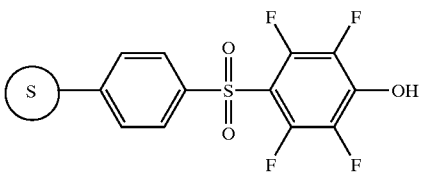

2,3,5,6-tetrafluorophenylsulfonyl-4-sulfonic acid-polystyrene resin, designated herein as

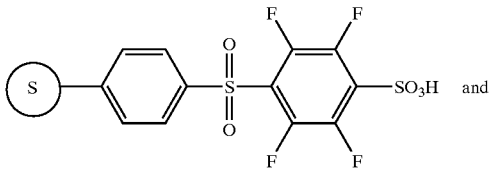

2,3,5,6-tetrafluorophenylsulfonyl-4-sulfonyl chloride-polystyrene resin, designated herein as

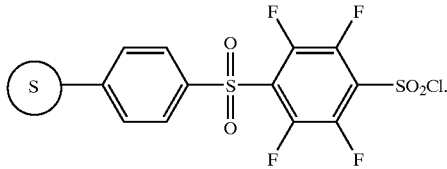

More preferred fluorophenyl resin compounds have formula I wherein

A is selected from

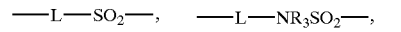

-continued

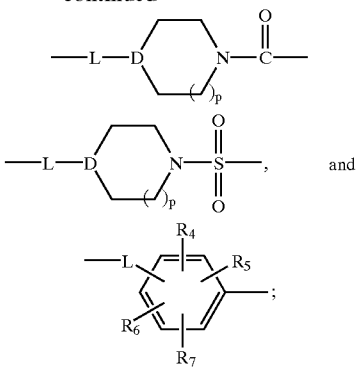

L is a chemical bond,

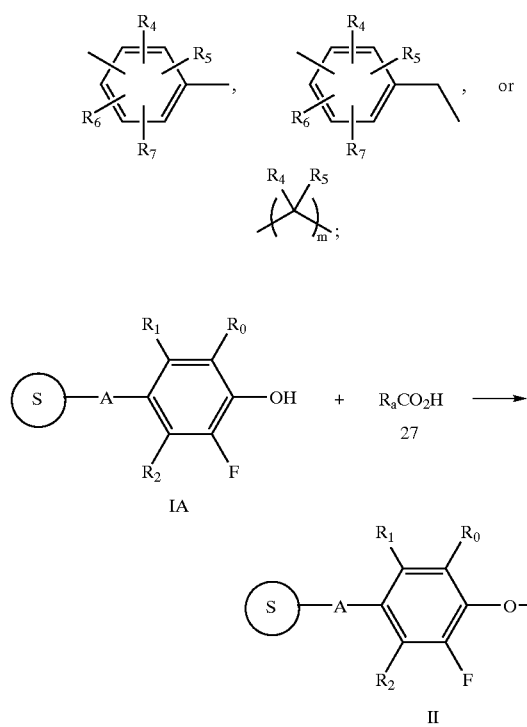

According to the foregoing Scheme 7, carboxylic acid compound 27 is coupled to the fluorophenyl resin compound IA using coupling conditions analogous to those described in Scheme 1 above to form the fluorophenyl activated ester resin compound II. Coupling times range from about 2 to about 24 hours depending on the nature of the fluorophenyl resin compound I, carboxylic acid 27, solvent, reaction temperature and activating agent. Coupling is preferably accomplished using diisopropylcarbodiimide (DIC) optionally in the presence of catalytic 4-dimethylaminopyridine (DMAP), or bromotripyrrolidinophosphonium hexafluorophosphate (PyBroP™) in the presence of triethylamine (TEA). The coupling reaction being carried out in a suitable solvent such as benzene, dichloromethane, dichloroethane, dioxane, THF or DMF at about ambient temperature over about 18 hours. A preferred solvent is anhydrous DMF. The fluorophenyl activated ester resin compound II is then washed with a suitable organic solvent or solvents to remove excess reagents. The fluorophenyl activated ester resin compound II may be dried and stored for future use or used directly in subsequent reactions.

The fluorophenyl activated ester resin compound II is odorless, air stable and free flowing. It is stable to storage at ambient temperature, and may be handled without any special precautions. A slurry of the fluorophenyl activated ester resin compound II in a solvent mixture such as DMF: dichloromethane may be used to distribute the resin via pipette, thereby facilitating automation. In contrast many acid chlorides and sulfonyl chlorides decompose under similar conditions, and are usually unstable to moisture in the air.

The cleavage of the fluorophenyl activated ester resin compound II with an amine is shown in Scheme 8. In Scheme 8, $R_b$ and $R_c$ represent independently H, an aliphatic group or an aromatic group, or $R_b$ and $R_c$, together with the N-atom to which they are attached form an optionally substituted azacycloalkyl ring or azacycloalkenyl ring, wherein $R_b$ and $R_c$ are amenable to the reaction of the amine 28 with the carbonyl moiety of the fluorophenyl activated ester resin compound II to effect the cleavage reaction described below using the reaction conditions described herein, Scheme 8 m is 1 to 5;

Y is $NR_3$ or $NR_3SO_2$;

B is —OH, —$SO_3H$, or —$SO_2Cl$; and $R_3$ is H.

Representative more preferred fluorophenyl resin compounds include, but are not limited to 4-hydroxy-2,3,5,6-tetrafluorobenzamidomethyl-polystyrene resin, 2,3,5,6-tetrafluorobenzamidomethyl-4-sulfonic acid-polystyrene resin, 2,3,5,6-tetrafluorobenzamidomethyl-4-sulfonyl chloride-polystyrene resin, 4-hydroxy-2,3,5,6-tetrafluorobenzoyl-polystyrene resin, 2,3,5,6-tetrafluorobenzoyl-4-sulfonic acid-polystyrene resin, 2,3,5,6-tetrafluorobenzoyl-4-sulfonyl chloride-polystyrene resin, 4-hydroxy-2,3,5,6-tetrafluorophenylsulfonamidomethyl-polystyrene resin, 4-(tripyrolidinium-O-phosphonium)-2,3,5,6-tetrafluorobenzamidomethyl-copoly(styrene-1%-divinylbenzene)-resin, 4-(N,N'-diisopropyl-isourea)-2,3,5,6-tetrafluorobenzamidomethyl-copoly(styrene-1%-divinylbenzene)-resin 2,3,5,6-tetrafluorophenylsulfonamidomethyl-4-sulfonic acid-polystyrene resin and 2,3,5,6-tetrafluorophenylsulfonamidomethyl-4-sulfonyl chloride-polystyrene resin.

The preparation of fluorophenyl activated ester resin compounds using the fluorophenyl resin compounds of this invention is shown in Scheme 7. In Scheme 7, $R_a$ represents any aliphatic or aromatic group amenable to coupling of the carboxylic acid compound 27 with the fluorophenyl resin compound IA using the reaction conditions described herein. The group $R_a$ may be further substituted and may contain functional groups suitable for further chemical transformations while attached to the resin. It is understood that these functional groups may be suitably protected to prevent interference with the coupling reaction and subsequent cleavage reaction described below. For a comprehensive treatise on the protection and deprotection of common functional groups see T. H. Greene and P. G. M. Wuts, Protective Groups in Organic Synthesis, 2nd edition, John Wiley & Sons, New York (1991), incorporated herein by reference.

Scheme 7

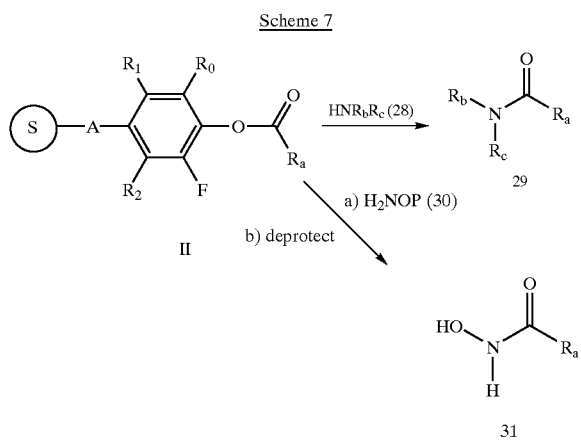

As shown in Scheme 8, the fluorophenyl activated ester resin compound II is cleaved by reaction with an amine of formula $HNR_bR_c$ in an organic solvent such as dichloromethane, dichloroethane, dioxane, THF or DMF at from about 20° C. to about 60° C. to prepare the amide 29. The reaction temperature and amount of time required for the cleavage reaction depends on the nature of the substituents $R_b$ and $R_c$. Cleavage is generally accomplished at about ambient temperature over about 2 to about 48 hours. A catalyst such as 4-dimethylaminopyridine is optionally added to accelerate the cleavage reaction.

In a similar manner, the fluorophenyl activated ester resin compound II is cleaved by reaction with a hydroxylamine of formula $H_2NOP$ wherein P is a hydroxy protecting group, preferably tetrahydropyranyl (THP). Removal of the hydroxy protecting group, for example using trifluoroacetic acid/dichloromethane when P is THP, provides the hydroxamic acid 31.

The reactivity of the fluorophenyl activated ester resin compound II toward cleavage by amines is comparable to the reactivity of the corresponding unsupported acylating reagent. Many amines possessing varying reactivities, including deactivated anilines such as 4-nitroaniline, react with the fluorophenyl activated ester resin compound II to give amide products. Typically less than one equivalent of the nucleophile is required to afford quantitative acylation of the nucleophile.

Polyfluorophenyl activated ester resin compounds possess further advantages over unsupported activated esters (i.e. pentafluorophenol, 4-nitrophenol) as well as acylating agents such as acid chlorides or acid anhydrides, including product isolation comprising simple filtration and solvent evaporation. There is no salt by-product or phenol by-product. The proton generated during the cleavage reaction is scavenged by the resin-bound fluorophenolate anion, therefore, in general, no excess base is required.

The fluorophenyl resin compounds of this invention are also useful for the preparation of peptides. In general, this method involves coupling the carboxyl group of a suitably N-protected first amino acid to the resin to form the resin-bound N-protected fluorophenyl activated ester resin compound, followed by cleavage of the fluorophenyl activated ester resin compound with a carboxy protected second amino acid to form a dipeptide which is protected at the carboxy and N termini.

If desired, a third amino acid is added by removing the N-protection from the dipeptide prepared as described above to form the carboxy protected dipeptide and cleaving the fluorophenyl activated ester resin compound of the third amino acid (suitably N-protected) to form the tripeptide which is protected at the carboxy and N termini. This process is then repeated until the desired amino acid residues have been incorporated in the peptide.

Alternatively, peptides comprising multiple amino acids are prepared by coupling a suitably N-protected peptide subunit comprising two or more amino acids to the fluorophenyl resin compound to form the fluorophenyl activated ester resin compound, and cleaving the fluorophenyl activated ester resin compound with a carboxy protected amino acid or second peptide subunit. Thus, in addition to the sequential addition of amino acids described above, a polypeptide may be prepared using the fluorophenyl resin compounds of this invention by coupling a N-protected peptide to the resin and cleaving the N-protected peptide fluorophenyl activated ester resin compound with a carboxy protected amino acid or peptide, or by coupling a N-protected amino acid to the resin and cleaving the N-protected amino acid fluorophenyl activated ester resin compound with a carboxy protected peptide.

N-protecting groups suitable for use in peptide synthesis using the fluorophenyl resin compounds of this invention should have the properties of being stable to the conditions of coupling to the amino acid or peptide to the fluorophenyl resin compound and cleavage of the fluorophenyl activated ester resin compound, while being readily removable without destruction of the growing peptide chain or racemization of any of the chiral centers contained therein. Suitable protecting groups include 9-fluorenylmethyloxycarbonyl (Fmoc), t-butyloxycarbonyl (Boc), benzyloxycarbonyl (Cbz), biphenylisopropyloxycarbonyl, t-amyloxycarbonyl, isobomyloxycarbonyl, (α,α)dimethyl-3,5-dimethoxybenzyloxycarbonyl, o-nitrophenylsulfenyl, 2-cyano-t-butyloxycarbonyl, and the like.

Carboxy protecting groups suitable for use in peptide synthesis using the fluorophenyl resin compounds of this invention should have the properties of being stable to cleavage of the resin-bound fluorophenyl activated ester, while being readily removable without destruction of the growing peptide chain or racemization of any of the chiral centers contained therein. Examples of carboxy protecting groups include esters such as methoxymethyl, methylthiomethyl, tetrahydropyranyl, benzyloxymethyl, substituted and unsubstituted phenacyl, 2,2,2-trichloroethyl, tert-butyl, cinnamyl, substituted and unsubstituted benzyl, trimethylsilyl, allyl, and the like, and amides and hydrazides including N,N-dimethyl, 7-nitroindolyl, hydrazide, N-phenylhydrazide, and the like. Especially preferred carboxylic acid protecting groups are tert-butyl and benzyl.

The fluorophenyl resin compounds of this invention are also useful for the preparation of amines as outlined in Schemes 9a and 9b. In scheme 9a, A, $R_0$, $R_1$, $R_2$, $R_a$, $R_b$ and $R_c$ are as defined herein.

Scheme 9a

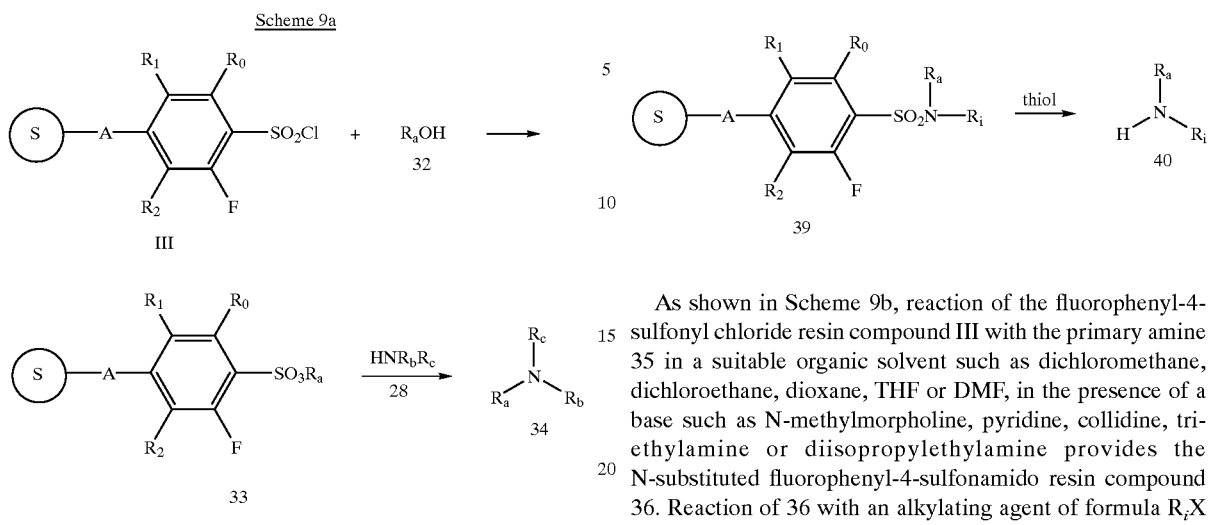

As shown in Scheme 9a, the 4-(oxysulfonyl)fluorophenyl resin compound 33 is prepared by reacting the fluorophenyl-4-sulfonyl chloride resin compound III with the hydroxy compound $R_aOH$ 32. The reaction is preferably carried out at ambient temperature in a suitable organic solvent such as dichloromethane, dichloroethane, dioxane, THF or DMF, in the presence of a base such as N-methylmorpholine, pyridine, collidine, triethylamine or diisopropylethylamine. Reaction of the 4-(oxysulfonyl)fluorophenyl resin compound 33 with the amine 28 provides the amine 34.

An alternative preparation of amines using the fluorophenyl resin compound of this invention is shown in Scheme 9b. In Scheme 9b, A, $R_0$, $R_1$, $R_2$, and $R_a$ is as defined herein and $R_i$ represents a group of formula —$CH_2R_f$ wherein $R_f$ is an aliphatic or aromatic group amenable to reaction with the N-substituted fluorophenyl-4-sulfonamido resin compound 36 to form the N,N-disubstituted fluorophenyl-4-sulfonamido resin compound 39, and reaction of 39 with a thiol, using the reaction conditions described below.

Scheme 9b

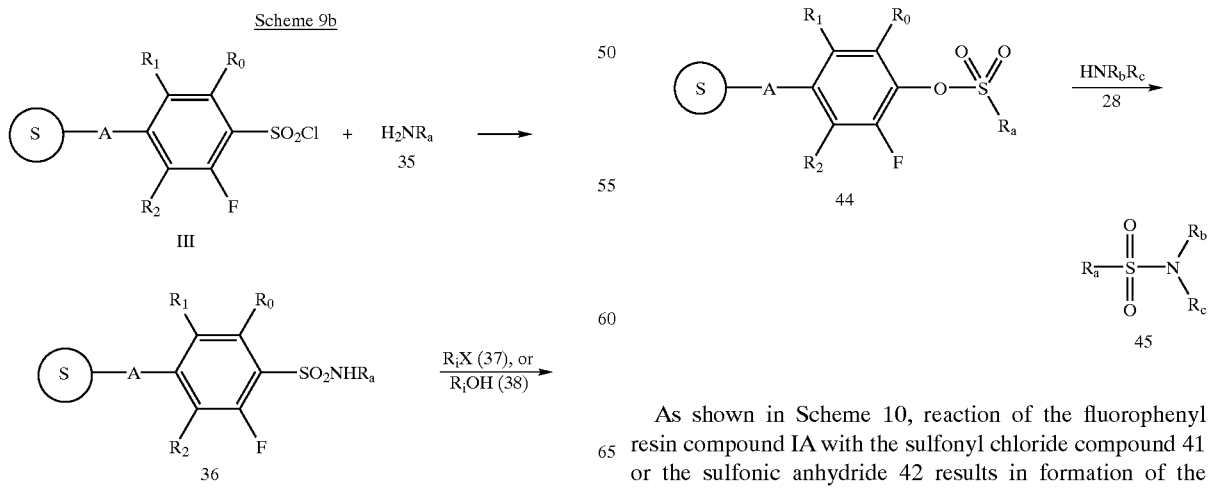

As shown in Scheme 9b, reaction of the fluorophenyl-4-sulfonyl chloride resin compound III with the primary amine 35 in a suitable organic solvent such as dichloromethane, dichloroethane, dioxane, THF or DMF, in the presence of a base such as N-methylmorpholine, pyridine, collidine, triethylamine or diisopropylethylamine provides the N-substituted fluorophenyl-4-sulfonamido resin compound 36. Reaction of 36 with an alkylating agent of formula $R_iX$ wherein X is Br or Cl, in a suitable organic solvent such as THF or DMF, in the presence of a base such as triethylamine or cesium carbonate; or with an alcohol of formula $R_iOH$ using Mitsunobu conditions (diethylazodicarboxylate or diisopropylazodicarboxylate and triphenylphosphine or tributylphosphine) provides the N,N-disubstituted fluorophenyl-4-sulfonamido resin compound 39. The secondary amine 40 is then displaced by treatment of the N,N-disubstituted fluorophenyl-4-sulfonamido resin compound 39 with a thiol compound such as thiophenol or ethanethiol.

The fluorophenyl resin compounds of this invention are also useful for the preparation of sulfonamides wherein $R_a$, $R_b$ and $R_c$ are as defined herein is outlined in Scheme 10.

Scheme 10

As shown in Scheme 10, reaction of the fluorophenyl resin compound IA with the sulfonyl chloride compound 41 or the sulfonic anhydride 42 results in formation of the 4-(sulfonyloxy)fluorophenyl resin compound 44. The reaction is preferably conducted at about ambient temperature in a suitable organic solvent such as dichloromethane, dichloroethane, dioxane, THF or DMF in the presence of a base such as N-methylmorpholine, pyridine, collidine, triethylamine or diisopropylethylamine. The 4-(sulfonyloxy) fluorophenyl resin compound 44 is also prepared by coupling of IA with the sulfonic acid compound 43, using analogous reagents and reaction conditions as described in Scheme 7, above. A preferred activating agent is diisopropylcarbodiimide.(DIC). Reaction of the 4-(sulfonyloxy)fluorophenyl resin compound 44 with the amine 28 in a suitable organic solvent as described above, preferably a polar aprotic solvent such as DMF, results in formation of the sulfonamide 45.

The preparation of carbamates 47 and urethanes 48 using the fluorophenyl resin compound of this invention is outlined in Scheme 11. In Scheme 11, $R_a$, $R_b$ and $R_c$ are defined herein and $R_d$ and $R_e$ represent independently H, an aliphatic group or an aromatic group amenable, or $R_d$ and $R_e$, together with the N-atom to which they are attached form an optionally substituted azacycloalkyl ring or azacycloalkenyl ring, wherein $R_d$ and $R_e$ are amenable to the reaction conditions described herein for cleavage of the 4-(aminocarbonyloxy) fluorophenyl resin compound 46.

diisopropylethylamine results in formation of the carbamate 47.

Likewise, reaction of 46 with an amine of formula $HNR_dR_e$ in a suitable organic solvent such as dichloromethane, dichloroethane, dioxane, THF or DMF, in the presence of a base such as N-methylmorpholine, pyridine, collidine, triethylamine or diisopropylethylamine results in formation of the urethane 48.

The 4-(aminocarbonyloxy)fluorophenyl resin compound 46 is prepared by reaction of the fluorophenyl resin compound IA with phosgene or 1,1'-carbonyldiimidazole in a suitable organic solvent such as dichloromethane, dichloroethane, dioxane, THF or DMF, optionally in the presence of a base such as N-methylmorpholine, pyridine, collidine, triethylamine or diisopropylethylamine, results in formation of the (4-carbonyloxy)fluorophenyl resin compound 49. Reaction of 49 with the amine of formula $HNR_bR_c$ in a suitable organic solvent and base as described above gives the 4-(aminocarbonyloxy)fluorophenyl resin compound 46.

The 4-(aminocarbonyloxy)fluorophenyl resin compound 46 may also be prepared in a single step by reaction of the fluorophenyl resin compound IA with a carbamoyl chloride

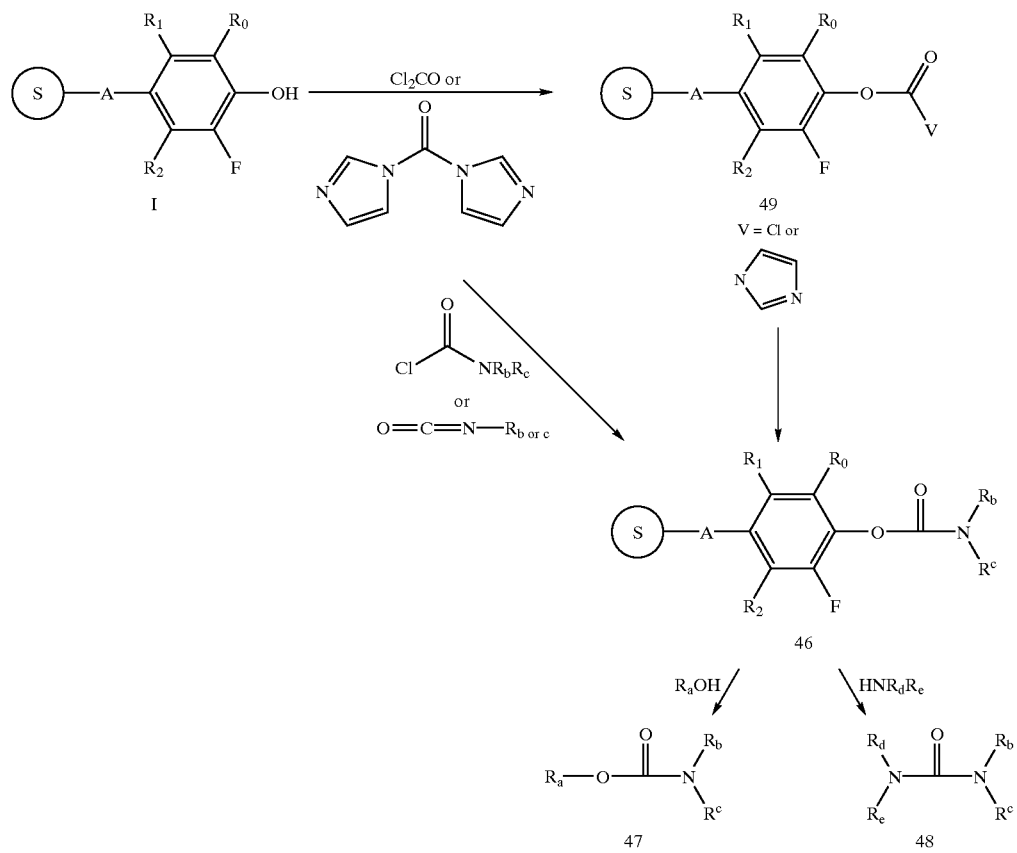

Scheme 11

As shown in Scheme 11, reaction of the 4-(aminocarbonyloxy)fluorophenyl resin compound 46 with the hydroxy compound $R_aOH$ in a suitable organic solvent such as dichloromethane, dichloroethane, dioxane, THF or DMF, in the presence of a base such as N-methylmorpholine, pyridine, collidine, triethylamine or of formula $ClC(O)NR_bR_c$. The reaction is performed in a suitable organic solvent such as dichloromethane, dichloroethane, dioxane, THF or DMF, in the presence of a base such as N-methylmorpholine, pyridine, collidine, triethylamine or diisopropylethylamine. In cases in which one of $R_b$ and $R_c$ is H and the other is aliphatic or aromatic, the 4-(aminocarbonyloxy)fluorophenyl resin compound 46 may be prepared by reaction of I with the isocyanate of formula O═C═N—R$_b$ or O═C═N—R$_c$ in a suitable organic solvent optionally in the presence of a base as described above The use of the fluorophenyl resin compound of this invention for the preparation of carbonates and in an alternative route to carbamates is shown in Scheme 12. In Scheme 12, R$_a$, R$_b$, R$_c$ and R$_f$ are as defined herein.

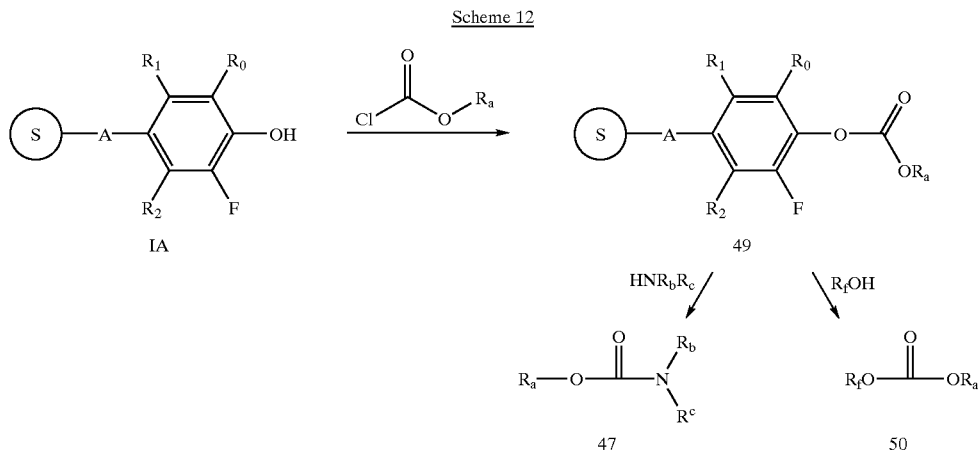

As shown in Scheme 12, reaction of the fluorophenyl resin compound IA with a chloroformate of formula ClC(Q)OR$_a$ in a suitable organic solvent such as dichloromethane, dichloroethane, dioxane, THF or DMF, optionally in the presence of a base such as N-methylmorpholine, pyridine, collidine, triethylamine or diisopropylethylamine provides the 4-(oxycarbonyloxy) fluorophenyl resin compound 49. Reaction of 49 with the amine HNR$_b$R$_c$ as described in Scheme 11 results in formation of the carbamate 47.

Likewise, reaction of 49 with an alcohol of formula R$_f$OH in a suitable organic solvent such as dichloromethane, dichloroethane, dioxane, THF or DMF, optionally in the presence of a base such as N-methylmorpholine, pyridine, collidine, triethylamine or diisopropylethylamine provides the carbonate 50.

Additionally, the fluorophenyl resin compounds of this invention are useful for constructing arrays of amide, peptide, hydroxamic acid, amine or sulfonamide combinatorial libraries or arrays of amides, peptides, hydroxamic acids, amines or sulfonamides as reagents in combinatorial library synthesis, for example reagents for the Ugi 4-component condensation (Ivar Ugi, in Isonitrile Chemistry, 1971, p. 145, Academic Press). The fluorophenyl resin compounds of this invention may be used for single functional group transformations and multiple step solid phase synthesis to generate combinatorial libraries.

The cleavage of the fluorophenyl activated ester resin compound II with carbon nucleophiles is shown in Scheme 13. In Scheme 13, R$_a$ is as defined herein and the groups R$_g$ and R$_h$ are independently H or any aliphatic or aromatic group which alone or in combination with the other of R$_g$ and R$_h$ renders the α-hydrogen sufficiently acidic to permit preparation of the carbon nucleophile —CHR$_g$R$_h$ under the basic reaction conditions described herein. R$_g$ and R$_h$ may contain additional functional groups. It is understood that these functional groups may be suitably protected to prevent interference with the deprotonation and cleavage reactions described below. For a comprehensive treatise on the protection and deprotection of common functional groups see T. H. Greene and P. G. M. Wuts, Protective Groups in Organic Synthesis, 2nd edition, John Wiley & Sons, New York (1991), incorporated herein by reference.

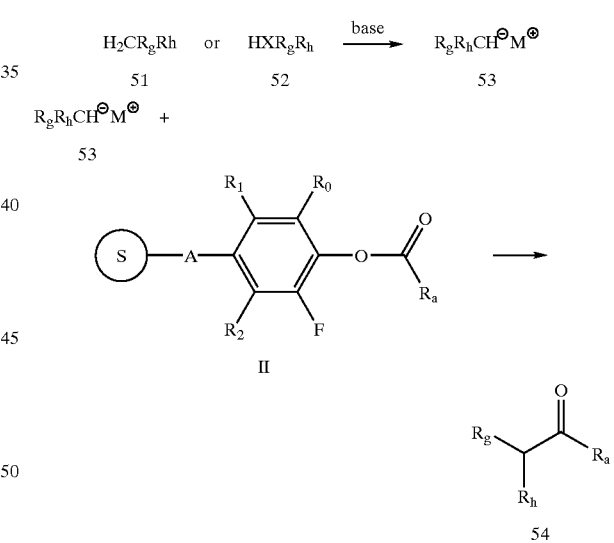

As shown in Scheme 13 above, treatment of the α-acidic carbon compound H$_2$CR$_g$R$_h$ 51 or halocarbon HXR$_g$R$_h$ (52, X=halogen) with base such as triethylamine, diisopropylethylamine, K$_2$CO$_3$, NaH, LiH, KH, lithium diisopropylamide, lithium hexamethyidisilazide, and the like, results in formation of the carbon nucleophile R$_g$R$_h$CH$^\ominus$M$^\oplus$ 53, wherein M$^\oplus$ represents a metal cation such as K$^+$, Na$^+$ or Li$^+$ or a quaternary nitrogen species resulting from extraction of a proton with an amine base such as triethylamine or diisopropylethylamine. The carbon nucleophile 53 may also be prepared by metal-halogen exchange, for example using magnesium metal to form the Grignard reagent, in which case M$^\oplus$ is MgBr. The reaction is carried out in an inert organic solvent such as tetrahydrofuran, diethyl ether, dioxane or dimethoxyethane at a temperature of from about −78 C to about ambient temperature. Reaction of 53 with the fluorophenyl activated ester resin compound II results in formation of the α-substituted carbonyl compound 54.

Alternatively, the carbon nucleophile 53 may be generated using a polymeric base such as the polymeric trityllithium reagent described by Cohen et al., *J. Amer. Chem. Soc.*, 1977, 99, 4165.

Preferred α-acidic carbon compounds suitable for use as carbon nucleophiles include Meldrum's acid, benzyl cyanide, acetophenone, ethyl phenylacetate, ethyl acetoacetate, triethyl phosphonoacetate and (carbethoxymethylene)triphenylphosphorane, Most preferred carbon nucleophile is a lithium enolate of a ketone, e.g. a lithium enolate of acetophenone, as exemplified in example 7.

The use of the fluorophenyl resin compounds of this invention for the parallel synthesis of a multiplicity of different amide, peptide, hydroxamid acid, amine, carbamate, urethane or sulfonamide end products is illustrated by the preparation of a multiplicity of amides shown in Schemes 14a and 14b below. In Schemes 14a and 14b, $R_a$ $R_b$ and $R_c$ are as defined herein and n is an integer which represents the total number of different amide products being prepared.

Scheme 14b

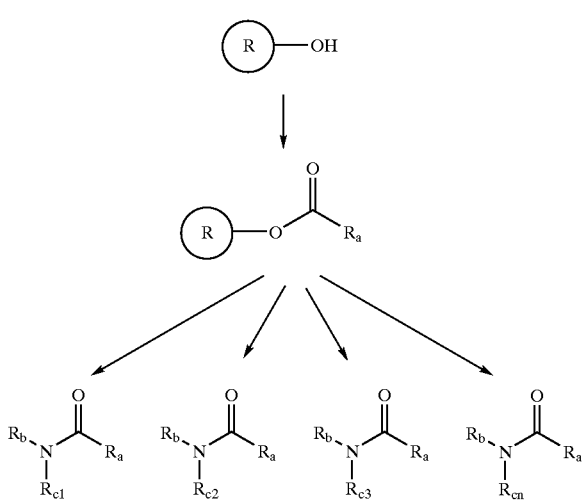

The parallel synthesis of n amides having variable N-substituents $R_{c1}$ to $R_{cn}$ is outlined in Scheme 14b above. According to Scheme 14b, the fluorophenyl resin compound of this invention is coupled with a carboxylic acid of formula Scheme 14a

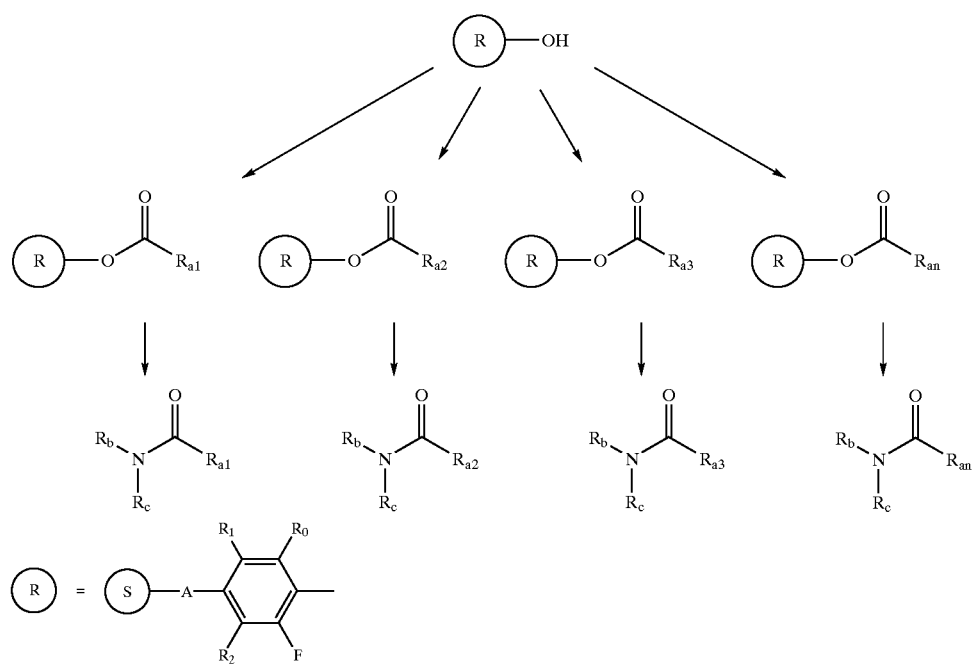

The parallel synthesis of a multiplicity of amides using a multiplicity of carboxylic acid compounds $R_{a1}CO_2H$ to $R_{an}CO_2H$ and a single amine $HNR_bR_c$ is shown in Scheme 14a. According to Scheme 14a, the fluorophenyl resin of this invention is divided into n portions. Each portion of resin is then coupled with a different carboxylic acid compound to give n portions of fluorophenyl activated ester resin compound. Each portion of fluorophenyl activated ester resin compound is then cleaved with an amine of formula $HNR_bR_c$ to give n portions of amide derived from a single amine but having different carbonyl group substituents.

$R_aCO_2H$. The resulting fluorophenyl activated ester resin compound is then divided into n portions, and each portion of fluorophenyl activated ester resin compound is cleaved with a different amine $HNR_bR_{c1}$ to $1NR_bR_{cn}$ to give the n different amide compounds derived from a single carboxylic acid.

The fluorophenyl resin compounds of this invention are also useful for constructing a combinatorial library of amide, peptide, hydroxamic acid, amine or sulfonamide end products as illustrated for the simple amide library prepared from 4 carboxylic acids and 4 amines outlined in Scheme 15.

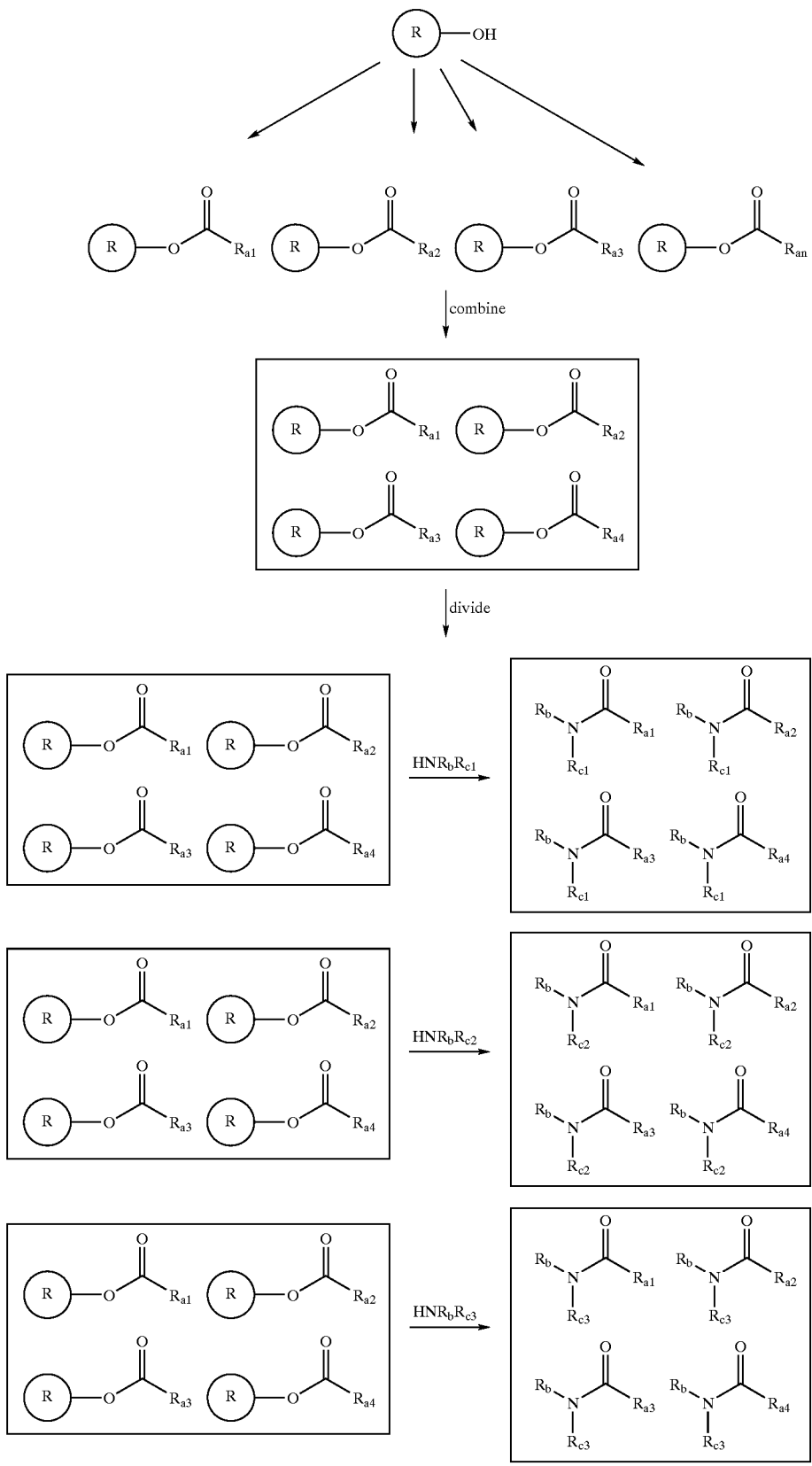
Scheme 15

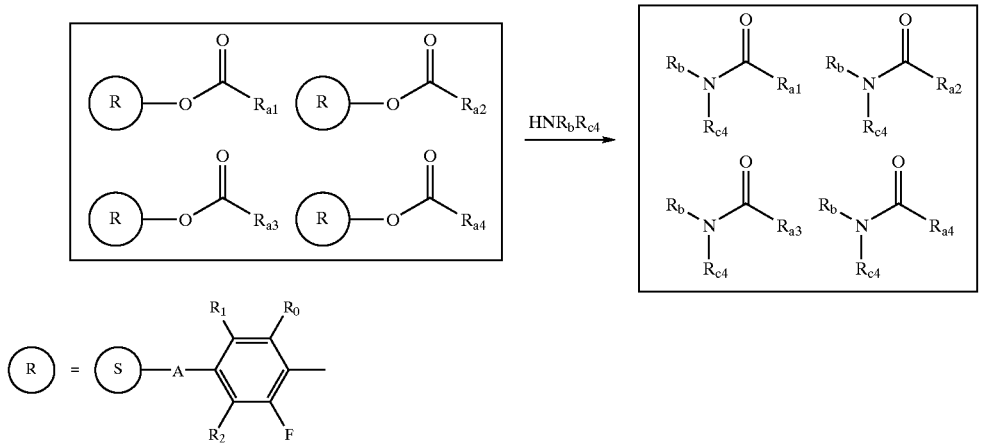

As shown in the foregoing Scheme 15, the fluorophenyl resin compound is divided in 4 portions, and each portion is coupled with a different carboxylic acid compound to prepare 4 different fluorophenyl activated ester resin compounds. The fluorophenyl activated ester resin compounds are then mixed together to form a single portion which is divided into 4 portions of fluorophenyl activated ester resin compound, in which each portion contains approximately equal amounts of each individual fluorophenyl activated ester resin compound. Each of the 4 portions of fluorophenyl activated ester resin compound is then cleaved with a different amine to give 4 portions of amide, each of which contains 4 compounds representing the products of cleavage of the 4 different fluorophenyl activated ester resin compound with a single amine. In this manner a combinatorial library containing a multiplicity of amides may be quickly constructed. In a similar manner, a combinatorial library of peptides may be assembled by repeating the dividing-recombining sequence for each amino acid or peptide building block.

The methodology described above for solid phase synthesis on resins is readily extended to synthesis on pins wherein the pins comprise a detachable polyethylene- or polypropylene-base head and an inert stem. The heads are grafted with a functionalized methacrylate copolymer on which the synthesis takes place. Synthesis on pins offers several advantages over resin-based solid phase synthesis techniques because it readily lends itself to automation and reduces the handling difficulties associated with conventional resin-based solid phase synthesis. Synthesis on pins is especially useful for the rapid construction of combinatorial libraries of amides or peptides. Solid phase synthesis pins is described in Technical Manual, Multipin™ SPOC, Chiron Technologies (1995) and references therein.

The preparation of amides on amino-functionalized pins is outlined in Scheme 16. In Scheme 16,

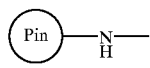

represents the polyethylene or polypropylene head described above on which is grafted a methacrylic acid-dimethylacrylamide copolymer substituted with a plurality of amino groups. The Fmoc-protected functionalized pin 55 is available from Chiron Mimotopes, San Diego, Calif. It is understood that while the preparation of amides is exemplified below, the methodology described in Schemes 1–14 above for the resin compounds of this invention is equally applicable to pins.

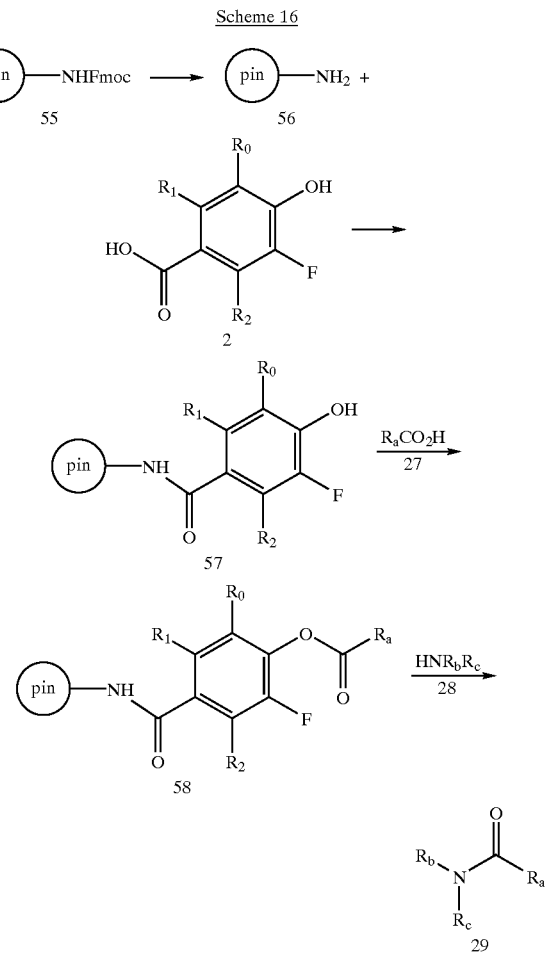

According to the foregoing Scheme 16, the Fmoc protected amino polymer 55 is deprotected by treatment with a basic amine, preferably 20% piperidine/DMF or 2% DBU/DMF. The free amino polymer 56 is functionalized by coupling with the 4-hydroxyfluorocarboxylic acid compound 2, for example using 1-hydroxybenzotriazole (HOBT) in the presence of N-methylmorpholine (NMM), diisopropylcarbodiimide (DIC) in the presence of HOBT or dicyclohexylcarbodiimide (DCC) in the presence of HOBT in a suitable solvent such as dichloromethane, N,N-dimethylformamide (DMF), N-methylpyrrolidone (NMP), or dichloromethane/DMF mixtures, to prepare the functionalized pins 57. Coupling of 57 with the carboxylic acid compound 27 to form the polymer bound fluorophenyl activated ester 58, followed by cleavage of 58 with the amine 28 provides the amide 29 under reaction conditions analogous to those described in Schemes 7 and 8 above.

It is to be understood that this invention covers all appropriate combinations of the particular and preferred groupings referred to herein.

The foregoing may be better understood by reference to the following examples, which are presented for illustration and are not intended to limit the scope of this invention.

$^{19}$F NMR $^{19}$F NMR spectra were obtained on a Varian unityplus spectrometer operating at a $^1$H frequency of 500 MHz. The $^1$H nanoprobe was tuned to $^{19}$F frequency. Typically, spectra were acquired with a (delay-pulse-acquire) sequence repeated for a number of transients (nt). Typical spectral width was 100,000 Hz and the chemical shifts were referenced relative to CFCl$_3$ using the transmitter frequency. The spectra were acquired using a nanoprobe in which the sample was oriented at a gmagic angle (54.7 degrees) relative to the magnetic field and the sample was spun at a rate of 1000–1500 Hz. The samples were prepared by swelling 1–2 mgs of resin with about 40 ul of deuterated dimethylformamide (DMF).

EXAMPLE 1

Preparation of 4-Hydroxy-2,3,5,6-tetrafluorobenzamidomethyl-copoly(styrene-1%-divinylbenzene)-resin

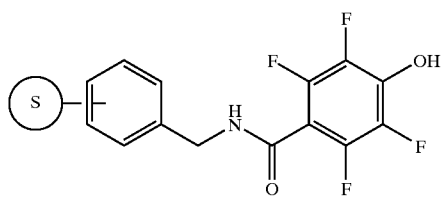

Aminomethyl polystyrene (0.39 mmol/gm); 2.0 gm; 0.78 mmol) is swelled in DMF (15 mL) for five minutes in a polypropylene syringe cartridge fitted with a bottom and top enclosure. To the resin suspension is added diisopropylcarbodiimde (492 mg; 3.9 mmol), 2,3,5,6,-tetrafluoro-4-hydroxybenzoic acid (819.35 mg; 3.9 mmol) and 4-dimethylaminopyridine (50 mg). The resulting mixture is shaken gently at room temperature overnight. Then the reaction mixture is filtered and thoroughly washed with DMF (3×20 mL), THF (3×20 mL), and CH$_2$Cl$_2$ (3×20 mL). The resin is dried in vacuo overnight at 40° C. IR 1764, 1691, 1653 cm$^{-1}$. Elemental analysis: calcd: N, 0.46; F, 2.51. Found: N, 0.57, 0.56; F, 3.65 3.68.

The resin is then placed in a polypropylene cartridge and treated with a 10% piperidine solution in DMF (3 mL) and shaken gently overnight. Then the reaction mixture is filtered and thoroughly washed with DMF (3×20 mL), THF (3×20 mL), and CH$_2$Cl$_2$ (3×20 mL). The resin is dried in vacuo overnight at 40° C. The IR spectrum of the resin showed the loss of the carbonyl signal at 1764 cm$^{-1}$, which is due to the formation of phenolic ester. This results in the formation of the resin as the piperidine salt.

EXAMPLE 2

Preparation of 4-Hydroxy-2,3,5,6-tetrafluorobenzamidomethyl-copoly(styrene-1%-divinylbenzene)-resin

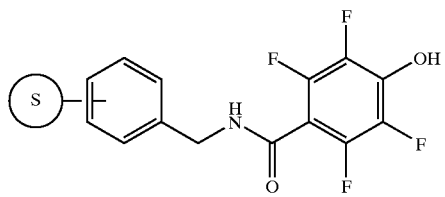

To a stirred slurry of aminomethyl polystyrene (0.82 mmol/g, 800 g, 656 mmol) in DMF (8 L) is added a solution of 2,3,5,6-tetrafluoro-4-hydroxybenzoic acid (234 g, 984 mmol) in DMF (1 L), a solution of 1-hydroxybenzotriazole (133 g, 984 mmol) in DMF (250 mL) and diisopropylcarbodiimide (124 g, 984 mmol) and the mixture is stirred overnight at ambient temperature. The reaction mixture is then filtered and the resin washed with DMF (1×1 L; 5×2 L), THF (3×2 L; 2×3 L) and CH$_2$Cl$_2$ (3×3 L). The resin is then air-dried in trays for 2 days.

The resin (995 g) is then added to a mixture of piperidine (125 mL) and DMF (6 L). DMF (2 L) is added to facilitate stirring and the mixture is stirred for 1 hour. The mixture is then filtered and the resin is washed with DMF (10×500 ml) and dried in vacuo.

The resin is then suspended in DMF (4 L) and a solution of 2M HCl (750 mL) in DMF (2 L) is added and the mixture is stirred for 0.5 hours. The resin is then filtered, washed with DMF (10 L) and THF (10 L) and dried overnight in vacuo at ambient temperature.

EXAMPLE 3

Preparation of 4-(Tripyrrolidinium-O-phosphonium)-2,3,5,6-tetrafluorobenzamidomethyl-copoly(styrene 1%-divinylbenzene)-resin

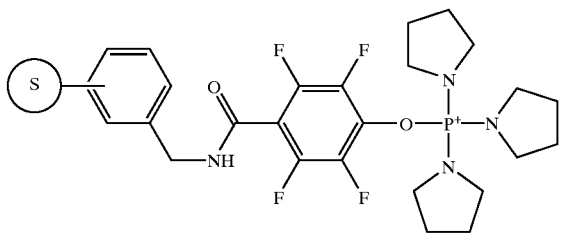

4-Hydroxy-2,3,5,6-tetrafluorobenzamidomethyl-copoly (styrene-1%-divinylbenzene)-resin (1.0 g, 0.97 mmol), prepared as in Example 1, was swelled with CH$_2$Cl$_2$ (40 mL)

for five minutes. Then bromotripyrrolidinophosphonium hexafluorophosphate (PyBrop™) (0.904 g, 1.94 mmol) and TEA (0.272 mL, 1.94 mmol) was added and the mixture was stirred for 15 h at room temperature and filtered. The resin was washed with CH$_2$Cl$_2$ (10×10 mL) and dried in vacuo at 20° C. to give 4-(tripyrrolidinium-O-phosphonium)-2,3,5,6-tetrafluorobenzamidomethyl-copoly(styrehe-1%-divinylbenzene)-resin. $^1$HNMR δ: 2.00 (s, CH2, 12H); 3.30 (s, NCH2, 12H); 4.50 (NCH2Ar). IR 3082, 2977, 1651, 1452, 1317, 1220, 1108, 991, 847, 758.

19F NMR d: −75 (3F); −78 (3F); −141 (2F); −156 (2F).

EXAMPLE 4

Loading of a carboxylic acid to resin using 4-(tripyrrolidinium-O-phosphonium)-2,3,5,6-tetrafluorotetrafluorobenzamidomethyl-copoly(styrene-1%-divinylbenzene)-resin.

Preparation of 4-(benzoyl)oxy-2,3,5,6-tetrafluorobenzamidomethyl-copoly(styrene-1%-divinylbenzene)-resin

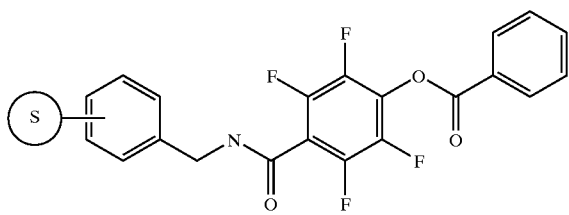

To a mixture of 4-(tripyrolidinium-O-phosphonium)-2,3,5,6-tetrafluorobenzamidomethyl-copoly(styrene-1%-divinylbenzene)-resin (71.5 mg, 50 μmol) in 1 mL of DMF were added benzoic acid (6.1 mg, 50 μmol) and diisopropylethylamine (DIEA) (43.5 μL, 250 μmol). The mixture was stirred for 15 h at 20° C. and filtered. The resin was washed with DMF (5×1 mL) and with CH$_2$Cl$_2$ (5×1 mL) and dried in vacuo at 20° C. to give the above product 4-(benzoyl)oxy (52 mg, 90%). $^1$HNMR δ: 4.50 (NCH2Ar), 7.50 (ArH, 2H), 7.60 (ArH, 1H), 8.20 (ArH, 2H). IR 3318, 1944, 1874, 1764, 1601, 1584, 1420, 1348, 1320, 1180, 1108, 993, 889, 795, 615.

EXAMPLE 5

Preparation of 4-(3-Methoxy-benzoyl)oxy-2,3,5,6-tetrafluorobenzamidomethyl-copoly(styrene-1%-divinylbenzene)-resin

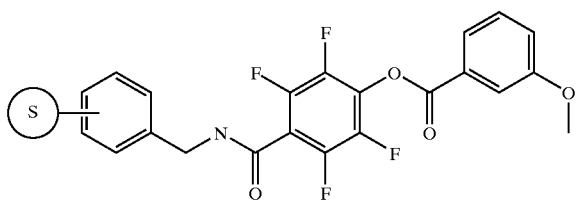

4-Hydroxy-2,3,5,6-tetrafluorobenzamidomethyl-copoly(styrene-1%-divinylbenzene)-resin (740 mg; 0.28 mmol), prepared as in Example 1, is swelled in DMF for five minutes. Diisopropylcarbodiimide (181 mg; 1.4 mmol), 3-methoxy-benzoic acid (109 mg; 1.4 mmol) and DMAP (50 mg) are added to the resin slurry and shaken in a polypropylene tube for 8 h at ambient temperature. The resin is then filtered and washed thoroughly with DMF (3×20 mL), THF (3×20 mL), and CH$_2$Cl$_2$ (3×20 mL). The resin is dried in vacuo overnight at 40° C. IR: 1766, 1682 cm$^{-1}$.

EXAMPLE 6

Cleavage of 4-(Benzoyl)oxy-2,3,5,6-tetrafluorobenzamidomethyl-copoly(styrene-1%-divinylbenzene)-resin With Aniline

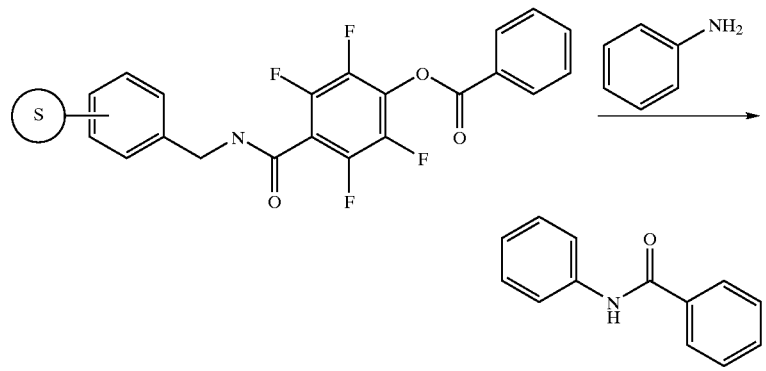

To the mixture of 4-(tripyrolidinium-O-phosphonium)-2,3,5,6-tetrafluorobenzamidomethyl-copoly(styrene-1%-divinylbenzene)-resin (71.5 mg, 50 µmol) in 1 mL of DMF were added benzoic acid (6.1 mg, 50 µmol) and DIEA (43.5 µL, 250 µmol). The mixture was stirred for 15 h at 20° C. and filtered. The resin was washed with DMF (5×1 mL). A solution of aniline in 1 mL of DMF and TEA (21 µL, 150 µmol) was added to the resin, and the resulting mixture was stirred for 15 h overnight at room temperature. After filtration, the amide was characterized by LCMS retention time 4.25 min [M+H]$^+$=198 purity >80%.

EXAMPLE 7

Cleavage of 4-(3-Methoxy-benzoyl)oxy-2,3,5,6-tetrafluorobenzamidomethyl-copoly(styrene-1%-divinylbenzene)-resin With the Lithium Enolate of Acetophenone

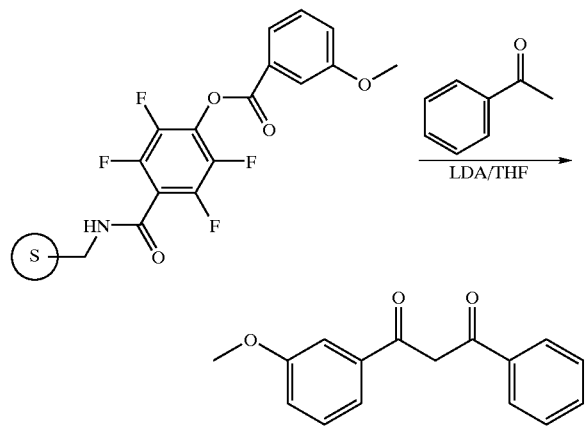

Preparation of 1-(3-Methoxyphenyl)-3-phenyl-1,3-dione

To a suspension of the resin (2 mg; 0.50 mmol) in dry THF (0.75 ml) was added the solution of acetophenone enolate (see below for preparation) in THF (0.45 mmol). The resin was shaken for 1 hour at room temperature. The solution was filtered into a tared vial and the solvent removed on a turbovap, residual solvent was removed in vacuo. MS m/z=255[M]$^+$. The resin was then washed with THF (×3), THF:H$_2$O (3:1, ×3), THF (×3) and DCM (×3) and dried in vacuo at 40° C. overnight. IR showed the lost the carbonyl stretch at 1766 cm$^{-1}$.

Preparation of enolate solution. To a solution of the acetophenone (60 mg; 2 mmol) in dry THF (2 ml) at 0° C. was added LDA dropwise (1 mL of a 2.0M solution in heptane/tetrahydrofuran/ethylbenzene). The solution was stirred at 0° C. for 30 minutes. The solution was used directly as a 0.67M solution without characterization.

Loading of the acyl group is typically accomplished using the diisopropyl activated ester, followed by incubation with the 4-hydroxy-2,3,5,6-tetrafluorobenzamidomethyl-copoly (styrene-1%-divinylbenzene)-resin. Alternative activation of resin via a pyrrolidine phosphonium salt intermediate is also possible and sometimes advantageous.

EXAMPLE 8

Preparation of 4-(3-Bromobenzoyl)oxy-2,3,5,6-tetrafluorobenzamidomethyl-copoly(styrene-1%-divinylbenzene)-resin

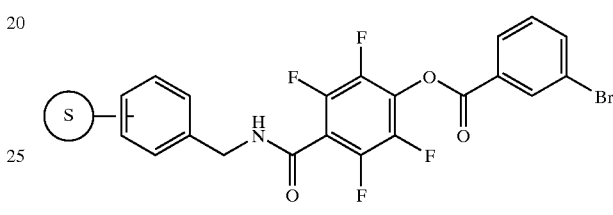

4-Hydroxy-2,3,5,6-tetrafluorobenzamidomethyl-copoly (styrene-1%-divinylbenzene)-resin (740 mg; 0.28 mmol), prepared as in Example 1, is swelled in DMF for five minutes. Diisopropylcarbodiimide (181 mg; 1.4 mmol), 3-bromobenzoic acid (290 mg; 1.4 mmol) and DMAP (50 mg) are added to the resin slurry and shaken in a polypropylene cartridge for 18 hours at ambient temperature. The resin is then filtered and washed thoroughly with DMF (3×20 mL), THF (3×20 mL), and CH$_2$Cl$_2$ (3×20 mL). The resin is vacuo overnight at 40° C. IR: 1765, 1692, 1649 cm$^{-1}$.

EXAMPLE 9

Cleavage of 4-(3-Bromobenzoyl)oxy-2,3,5,6-tetrafluorobenzamidomethyl-copoly(styrene-1%-divinylbenzene)-resin With Anilines

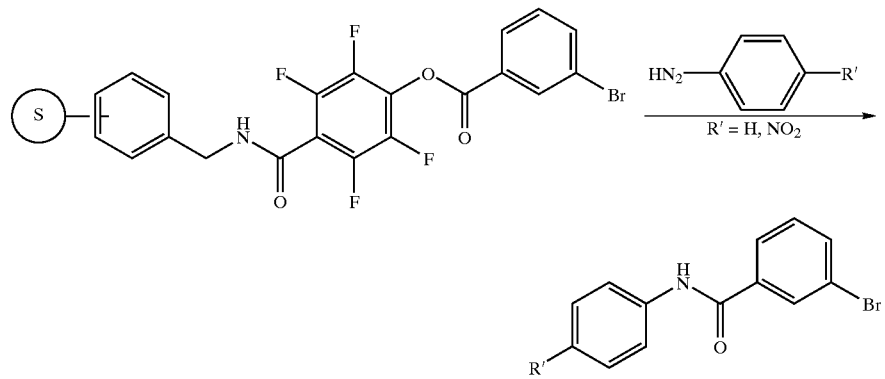

4-(3-bromobenzoyl)oxy-2,3,5,6-tetrafluoro-benzamidomethyl-copoly(styrene-1%-divinylbenzene)-resin (50 mg; 0.015 mmol), prepared as in Example 8, is swelled in dichloroethane for five minutes followed by addition of aniline (1 equiv.; 1.4 mg; 0.015 mmol) or 4-nitroaniline (1 equiv.; 2.07 mg; 0.015 mmol). The reaction mixture is stirred for 2 days at ambient temperature. The reaction mixture is then filtered and the filtrate is concentrated in vacuo to give N-phenyl-3-bromobenzamide or N-(4-nitrophenyl)-3-bromobenzamide.

EXAMPLE 10

Preparation of an Array of 4-Carboxy-2,3,5,6-tetrafluorobenzamidomethyl-copoly(styrene-1%-divinylbenzene)derivatives

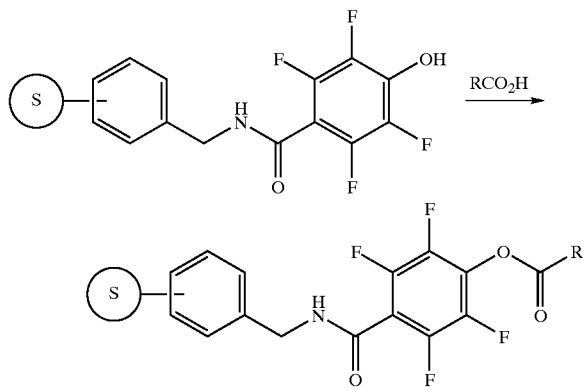

Forty 20 mL polypropylene cartridges are placed in a rack, and 4-hydroxy-2,3,5,6-tetrafluorobenzamidomethyl-copoly(styrene-1%-divinylbenzene)-resin (0.47 mmol/g, 0.5 g) and DMF (4 mL) are added to each tube. Diisopropyl-carbodiimide (0.186 mL) is then added to each tube using an Eppendorf pipette, followed by 1.0 mL of a stock solution prepared by dissolving dimethylaminopyridine (1.72 g) in DMF (40 mL). Five equivalents of carboxylic acid (0.24 mmol) is then placed in each tube and the rack of tubes is shaken overnight at ambient temperature. The resin in each tube is then filtered, washed with DMF (5×5 mL), THF (5×5 mL) and CH$_2$Cl$_2$ (5×5mL) and dried overnight at 35° C. in a vacuum oven.

EXAMPLE 11

Preparation of 2,3,4,5,6-Pentafluorobenzoyl-copoly(styrene-1%-divinylbenzene)-resin

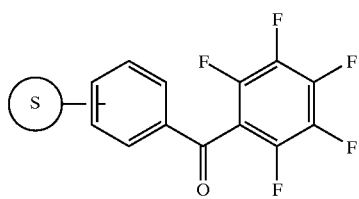

To a mixture of copoly(styrene-1%-divinylbenzene) resin (100–200 mesh, 10 g) and pentafluorobenzoyl chloride (25 g) in nitrobenzene (250 mL) is added AlCl$_3$ (1.0 M in nitrobenzene, 38 mL) and the reaction mixture is stirred at 60° C. for 18 hours. The reaction mixture is then poured into a mixture of DMF (30 mL), concentrated HCl (20 mL) and ice (80 g). The mixture is stirred for 30 minutes, filtered, and the resin is washed with 3:1 DMF-H$_2$O until the washings are colorless. The resin is then washed with warm DMF and 2:1 dichloromethane-methanol (6×) and dried in vacuo. $^{19}$F NMR δ −146.5 (2F), −157 (1F), −165.5 (2F).

EXAMPLE 12

Preparation of 4-Hydroxy-2,3,5,6-tetrafluorobenzoyl-copoly(styrene-1%-divinylbenzene)-resin

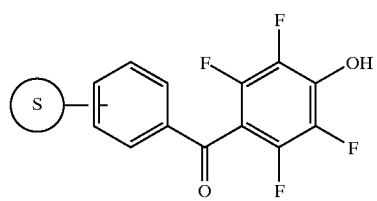

The title resin is prepared by treating a mixture of 2,3,4,5,6-pentafluorobenzoyl-copoly(styrene-1%-divinylbenzene)-resin in water/cyclohexane with sodium hydroxide and tetrabutylammonium hydrogen sulfate as described by Feldman et al., *J. Org. Chem.*, 1991, 56 (26), 7350–7354.

EXAMPLE 13

Preparation of 2,3,5,6-Tetrafluorobenzoyl-4-sulfonic Acid-copoly(styrene-1%-divinylbenzene)-resin

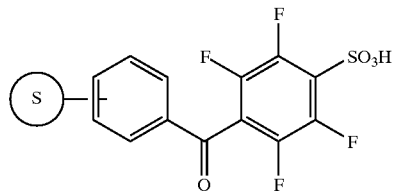

A mixture of 2,3,4,5,6-pentafluorobenzoyl-copoly(styrene-1%-divinylbenzene)-resin (325 mg), prepared as in Example 11, dichloromethane (3 mL), H$_2$O (1 mL), triethylamine (1.2 mL) and potassium metabisulfite (560 mg) is stirred for 3 days. The resin is then washed with dichloromethane (6×) and dried in vacuo at 40° C. $^{19}$F NMR δ −142 (2F), −147 (2F).

EXAMPLE 14

Preparation of 2,3,5,6-Tetrafluorobenzoyl-4-sulfonyl Chloride-copoly(styrene-1%-divinylbenzene)-resin

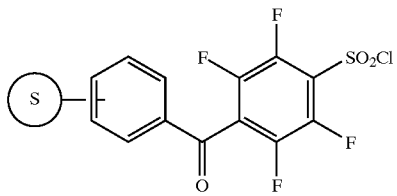

The 2,3,5,6-tetrafluorobenzene-4-sulfonic acid-copoly(styrene-1%-divinylbenzene)-resin (300 mg), prepared in Example 13, is swelled in carbon tetrachloride (3 mL) and chlorosulfonic acid (1 mL) is added. The reaction mixture is stirred for 24 hours and then is quenched with acetic acid. The resin is filtered, washed with dichloromethane (6×) and ether (4×) and dried in vacuo at 40° C. $^{19}$F NMR δ −142 (2F), −146.5 (2F).

EXAMPLE 15

Preparation of 2,3,5,6-Tetrafluorobenzoyl-4-(4-fluorobenzyloxy)sulfonyl-copoly(styrene-1%-divinylbenzene)-resin

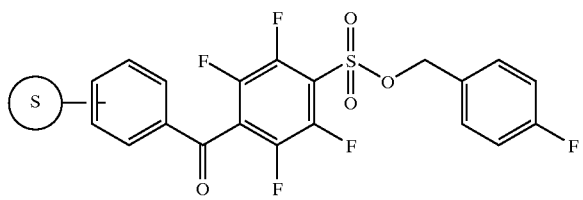

2,3,5,6-Tetrafluorobenzoyl-4-sulfonyl chloride-copoly(styrene-1%-divinylbenzene)-resin (100 mg), prepared as in Example 14, is swelled in dichloromethane, and triethylamine (0.1 mL) and 4-fluorobenzyl alcohol (0.087 mL) are added, then the reaction mixture is stirred for 18 hours. The resin is then filtered, washed with dichloromethane (6×) and dried in vacuo. $^{19}$F NMR δ −115 (1F), −142.5 (2F), −146 (2F).

EXAMPLE 16

Cleavage of 2,3,5,6-Tetrafluorobenzoyl-4-(4-fluorobenzyloxy)sulfonyl-copoly(styrene-1%-divinylbenzene)-resin With Anilines

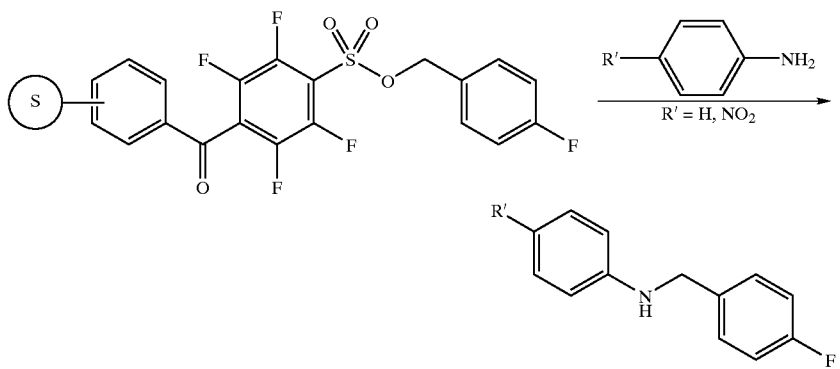

2,3,5,6-tetrafluorobenzoyl-4-(4-fluorobenzyloxy)sulfonyl-copoly(styrene-1%-divinylbenzene)-resin, prepared as in Example 15, is swelled in dichloroethane, and aniline (1 equiv) or 4-nitroaniline (1 equiv.) is added. The reaction mixture is stirred for 2 days at ambient temperature. The reaction mixture is then filtered and the filtrate is concentrated in vacuo to give N-(4-fluorobenzyl)-N-phenylamine or N-(4-fluorobenzyl-N-(4-nitrophenyl)amine.

EXAMPLE 17

Preparation of 4-(Naphth-1-ylsulfonyl)oxy-2,3,5,6-tetrafluorobenzamidomethyl-copoly(styrene-1%-divinylbenzene)-resin

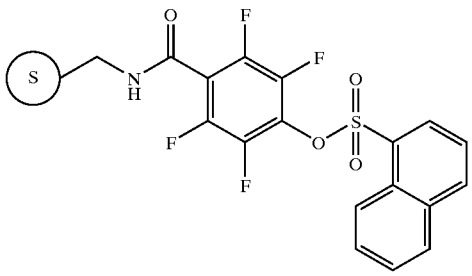

Method A:

1-Naphthyl sulfonic acid (500 mg; 2.4 mmol) is dissolved in 3 mL of dichloromethane. Diisopropyl carbodiimide (151.2 mg; 1.2 mmol) is added to the reaction vessel and the mixture is stirred for 1 hour at ambient temperature. 4-Hydroxy-2,3,5,6-tetrafluorobenzamidomethyl-copoly(styrene-1%-divinylbenzene)-resin is added (500 mg; 0.47 mmol/g; 0.24 mmol) to the reaction vessel and the reaction mixture is shaken overnight at ambient temperature. The reaction mixture is filtered and the resin is washed with 20% aqueous DMF (5×2 mL), DMF (5×2 mL), THF (5×2 mL) and dichloromethane (5×2 mL), then dried in vacuo at ambient temperature overnight.

Method B:

4-Hydroxy-2,3,5,6-tetrafluorobenzamidomethyl-copoly(styrene-1%-divinylbenzene)-resin (1 g; 0.76 mmol/g; 0.76 mmol) is swelled in 10 mL of dichloromethane. Diisopropylethylamine (0.523 mL; 3.04 mmol) is added to the reaction vessel followed by 1-naphthalene sulfonyl chloride (0.510 g; 2.28 mmol). The reaction mixture is shaken at ambient temperature for 2 hours and then is filtered and the resin is washed with 20% aqueous DMF (5×2 mL), DMF (5×2 mL), THF (5×2 mL), and dichloromethane (5×2 mL), then dried in vacuo at ambient temperature overnight. IR (cm$^{-1}$): 1675 (amide carbonyl stretch), 1389, 1185 (SO$_2$ stretch). $^{19}$F NMR δ −155.2; −145.5. TFP Resin unsubstituted $^{19}$F NMR δ −164.5; −146.5

EXAMPLE 18

Preparation of 1-(Piperidinylsulfonyl)naphthalene

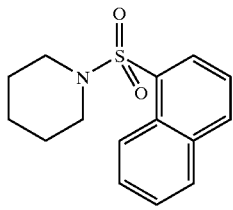

4-(Naphth-1-ylsulfonyl)oxy-2,3,5,6-tetrafluoro-benzamidomethyl-copoly(styrene-1%-divinylbenzene)-resin, prepared as in Example 17, (100 mg; ca. 0.047 mmol) is swelled in DMF for 5 minutes. Piperdine (3.1 mg; 0.037 mmol) is added to the reaction vessel and the reaction mixture is shaken for 12 hours at ambient temperature. The reaction mixture is then filtered and the filtrate is collected and concentrated to yield 1-(piperidinylsulfonyl) naphthalene. MS m/z 276 [M+H]$^+$.

EXAMPLE 19

Preparation of 4-(Toluene-4-ylsulfonyl)oxy-2,3,5,6-tetrafluorobenzamidomethyl-copoly(styrene-1%-divinylbenzene)-resin

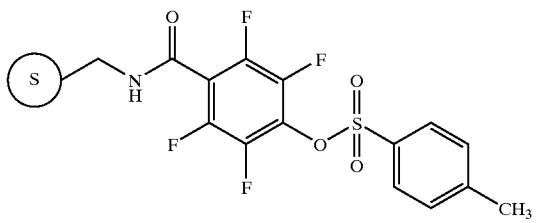

4-Hydroxy-2,3,5,6-tetrafluorobenzamidomethyl-copoly (styrene-1%-divinylbenzene)-resin (200 mg; 0.47 mmol/g; 0.094 mmol) is swelled in 3 mL of dichloromethane. Diisopropylethylamine (0.122 mL; 0.705 mmol) is added to the reaction vessel followed by tosyl chloride (89 mg; 0.47 mmol). The reaction mixture is shaken at ambient temperature for 2 hours. The reaction mixture is then filtered and the resin is washed with 20% aqueous DMF (5×2 mL), DMF (5×2 mL), THF (5×2 mL), and dichloromethane (5×2 mL), then dried in vacuo at ambient temperature overnight. IR (cm$^{-1}$): 1693 (amide carbonyl stretch), 1397, 1195 (SO$_2$ stretch).

EXAMPLE 20

Preparation of 4-(Piperidinylsulfonyl)toluene

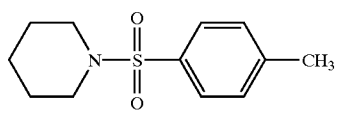

The 4-(toluene-4-ylsulfonyl)oxy-2,3,5,6-tetrafluorobenzamidomethyl-copoly(styrene-1%-divinylbenzene)-resin prepared in Example 19 (100 mg; ca. 0.047 mmol) is swelled in DMF for 5 minutes. Piperidine (3.1 mg; 0.037 mmol) is added to the reaction vessel and the reaction mixture is shaken for 12 hours at ambient temperature. The reaction mixture is then filtered and the filtrate is collected and concentrated to yield 4-(piperidinylsulfonyl) toluene. MS m/z 240 [M+H]$^+$.

EXAMPLE 21

Preparation of 4-(4-Fluorophenylsulfonyl)oxy-2,3,5,6-tetrafluorobenzamidomnethyl-copoly(styrene-1%-divinylbenzene)-resin

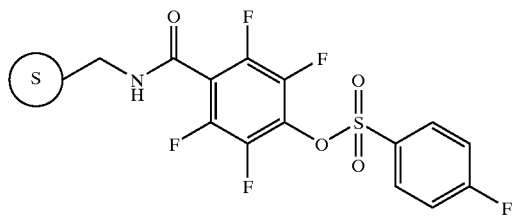

The title resin is prepared according to the method of Example 17, Method B, except substituting 4-fluorobenzenesulfonyl chloride for 1-naphthylenesulfonyl chloride. IR (cm$^-$): 1675 (amide carbonyl stretch), 1394, 1194 (SO$_2$ stretch). $^{19}$F NMR δ −155 (2 F); −145.5 (2 F); −104.5 (1 F). TFP Resin unsubstituted $^{19}$F NMR δ −164.5; −146.5.

EXAMPLE 22

Preparation of 2,3,4,5,6-Pentafluorophenylsulfonamidomethyl-copoly(styrene-1%-divinylbenzene)-resin

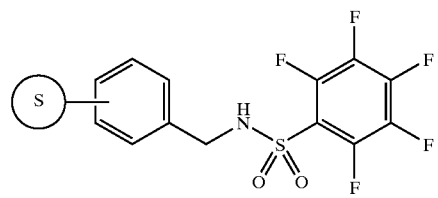

Aminomethyl polystyrene (1 g, 1.2 mmol) is swelled with dichloromethane and 2,4,6-collidine (0.475 mL, 3.6 mmol) and 2,3,4,5,6-pentafluorophenylsulfonyl chloride (1.44 mmol) are added. The reaction mixture is stirred for 5 hours and the resin is filtered, washed with dichloromethane (6×) and dried in vacuo at 40° C.

EXAMPLE 23

Preparation of 4-Hydroxy-2,3,5,6-tetrafluorophenylsulfonamidomethyl-copoly(styrene-1%-divinylbenzene)-resin

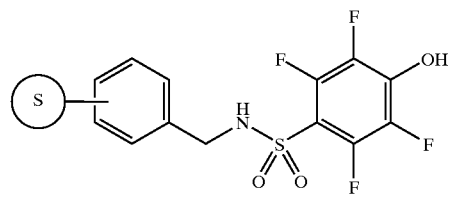

The title resin is prepared according to the method of Example 12, except substituting 2,3,4,5,6-pentafluorophenylsulfonamidomethyl-copoly(styrene-1%-divinylbenzene)-resin, prepared as in Example 22, for 2,3,4,5,6-pentafluorobenzoyl-copoly(styrene-1%-divinylbenzene)-resin.

(styrene-1%-divinylbenzene)-resin showed: $^{19}$F-NMR δ −144.572, −145.608; IR (cm−1) 1684 (C=O stretch), 1391, (asymmetric $SO_2$ stretch) 1195, 1177 (symmetric $SO_2$ stretch).

EXAMPLE 24

Parallel Synthesis of an Array of (Aryl or Heteroaryl)-sulfonic Acid [2-oxo-1-(1H-Pyrrolo[3,2-b]pyridin-2-ylmethyl)-pyrrolidin-3-(S)-yl]-amide Trifluoroacetates

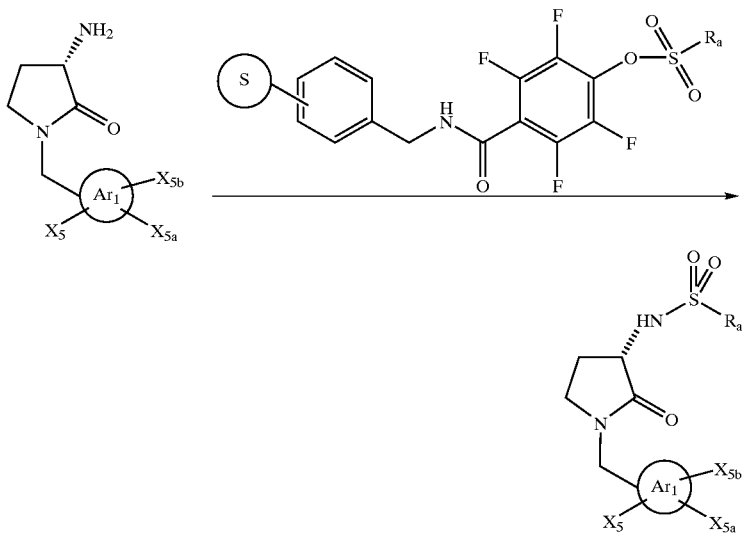

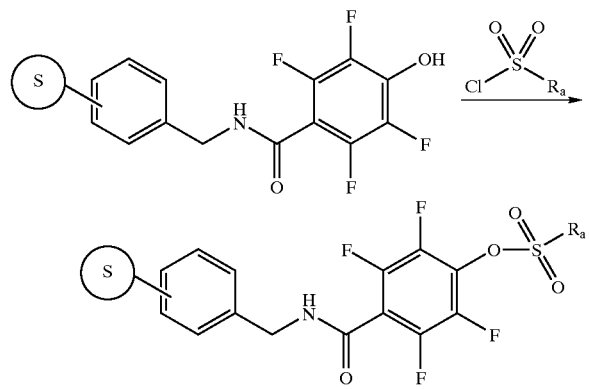

Reaction vessels are charged with 4-hydroxy-2,3,5,6-tetrafluorobenzamidomethyl-copoly-(styrene-1%-divinylbenzene)-resin (0.20 g, 0.15 mmol). Each container is treated with methylene chloride (2 mL) for 10 minutes followed by an aromatic sulfonyl chloride (0.45 mmol) and diisopropylethyl amine (0.104 ml, 0.60 mmol). The containers are sealed and agitated for about 16 h. The reaction mixtures are individually filtered and sequentially washed with 20% aqueous DMF (10×), THF (5×) and dichloromethane (5×), then dried in vacuo at ambient temperature overnight. By way of example 6-chlorobenzothiophene-2-sulfonyl)oxy-2,3,5,6-tetrafluoro-benzamidomethyl-copoly- Reaction vessels are charged with arylsulfonyloxy-2,3,5,6-tetrafluoro-benzamidomethyl-copoly-(styrene-1%-divinylbenzene)-resins (0.024 g, 0.012 mmol), prepared as described above. The resins are swelled with DMF, then treated with a 0.01 M solution of an amine (1 ml, 0.01 mmol) in DMF. The containers are covered with aluminum foil and agitated for 72 h. The progress of the reaction is monitored by TLC; for sluggish reactions 1,5,7-triazabicyclo[4.4.0]dec-5-ene resin is added. The reaction mixtures are individually filtered and the resins washed with methanol. The filtrates are concentrated with a stream of nitrogen. The residues are redissolved in methanol and reconcentrated twice more. The resulting residues are treated with 20% trifluoroacetic acid in methylene chloride (1 ml) and agitated overnight. The reaction mixture is concentrated by a stream of nitrogen. Methylene chloride (1 ml) is added and concentrated with a stream of nitrogen. Methanol (1 ml) is added; concentrate with a stream of nitrogen. The final residues are analyzed by LC/mass spec; evidence of desired product was obtained in each case. By way of example, the product from the reaction of 6-chlorobenzothiophene-2-sulfonyl)oxy-2,3,5,6-tetrafluoro-benzamidomethyl-copoly-(styrene-1%-divinylbenzene)-resin with 2-(3-(S)-amino-2-oxopyrrolidin-1-ylmethyl)-pyrrolo[3,2-b]pyridine-1-carboxylic acid tert-butyl ester and subsequent deprotection with 20% TFA in methylene chloride showed: M+H=461. This material had an $IC_{50}$, against Factor Xa of less than 500 nM.

By the methods described in this preparation, 2-(3-(S)-amino-2-oxopyrrolidin-1-ylmethyl)-pyrrolo[3,2-b]pyridine-1-carboxylic acid tert-butyl ester, 2-(3-(S)-amino-2-oxopyrrolidin-1-ylmethyl)-pyrrolo[3,2-c]pyridine-1-carboxylic acid tert-butyl ester and 2-(3-(S)-amino-2-oxopyrrolidin-1-ylmethyl)-pyrrolo[2,3-c]pyridine-1-carboxylic acid tert-butyl ester are reacted with fourteen arylsulfonyloxy-2,3,5,6-tetrafluoro-benzamidomethyl-copoly-(styrene-1%-divinylbenzene)-resins to obtain, after deprotection, compounds encompassed by the following formula:

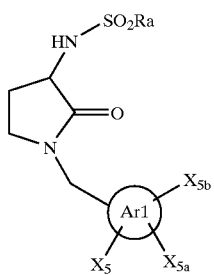

wherein

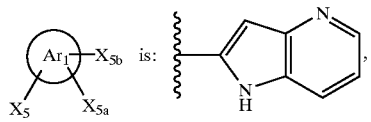

and Ra is:

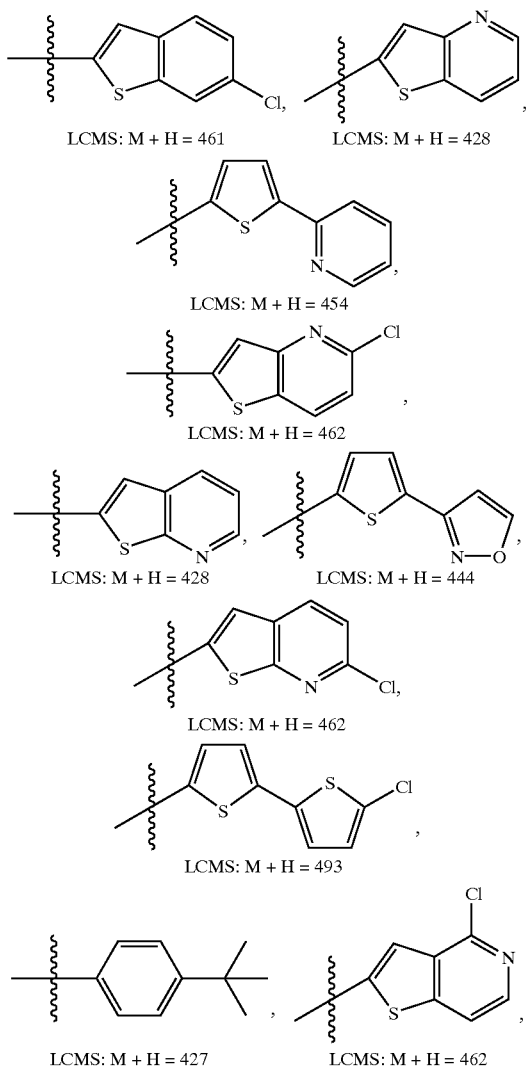

-continued

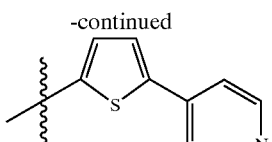

LCMS: M + H = 454

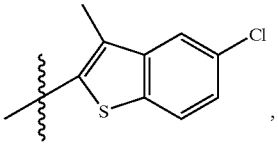

LCMS: M + H = 475

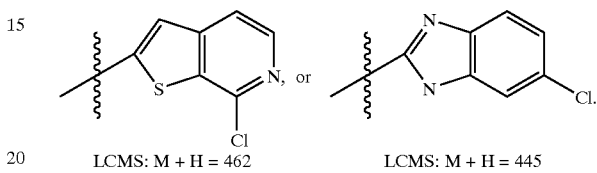

LCMS: M + H = 462    LCMS: M + H = 445

EXAMPLE 25

Parallel Synthesis of an Array of (Aryl or Heteroaryl)-sulfonic Acid [2-oxo-1-(1H-Pyrrolo[3,2-c]pyridin-2-ylmethyl)-pyrrolidin-3-(S)-yl]-amide Trifluoroacetates The title array of compounds is prepared from 2-(3-(S)-amino-2-oxopyrrolidin-1-ylmethyl)-pyrrolo[3,2-c]pyridine-1-carboxylic acid tert-butyl ester as described from Example 24.

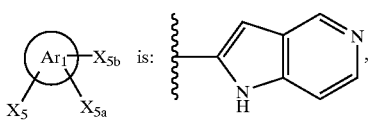

and $R_a$ is:

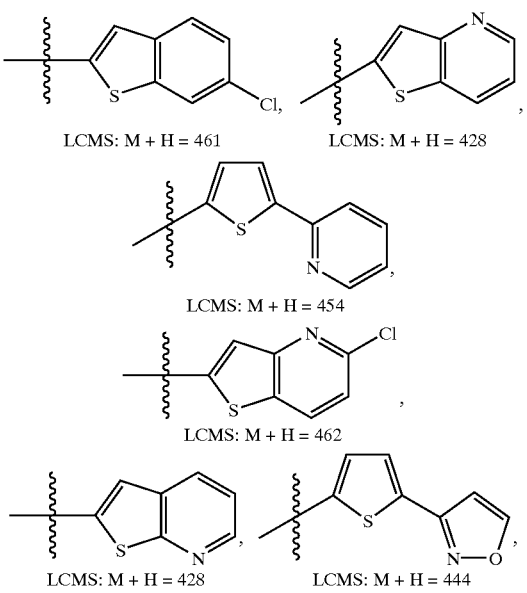

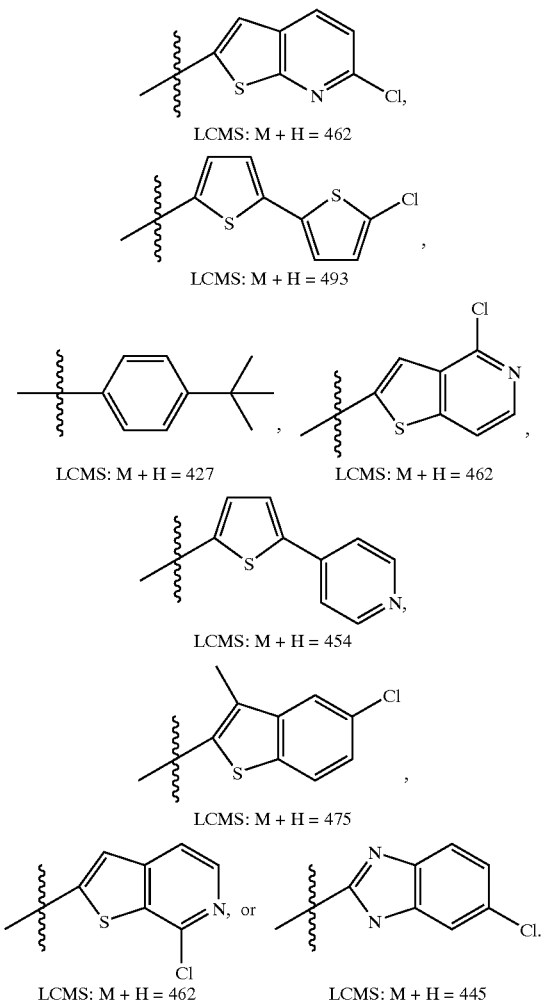
EXAMPLE 26
Parallel Synthesis of an Array of (Aryl or Heteroaryl)-sulfonic Acid [2-oxo-1-(1H-Pyrrolo[2,3-c]pyridin-2-ylmethyl)-pyrrolidin-3-(S)-yl]-amide Trifluoroacetates
The title array of compounds is prepared from 2-(3-(S)-amino-2-oxopyrrolidin-1-ylmethyl)-pyrrolo[2,3-c]pyridine-1-carboxylic acid tert-butyl ester as described from Example 24.
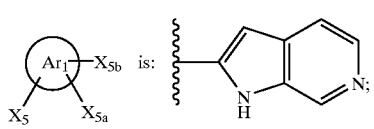
and
$R_a$ is:
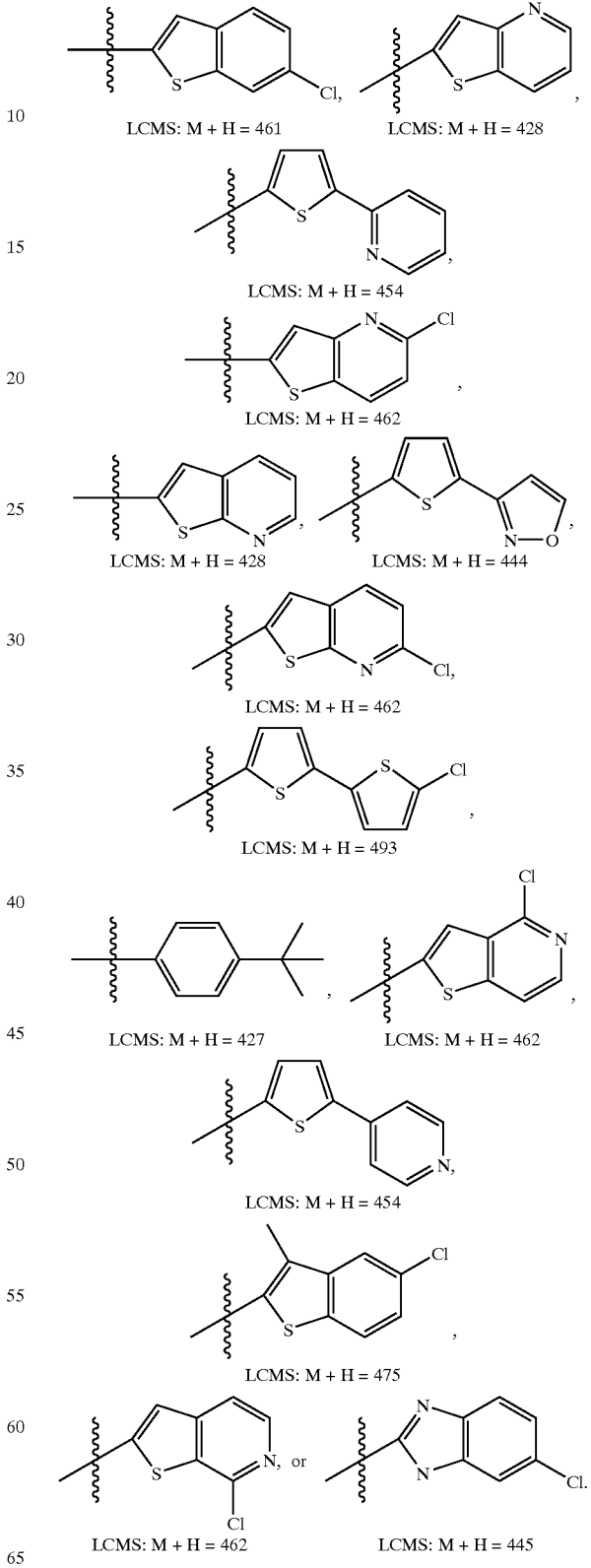

EXAMPLE 27

Preparation of Triple Lysine-loaded 4-Hydroxy-2,3,5,6-tetrafluorobenzoyl-functionalized Pins Step 1: Piperidine Cleavage:

To a 20% piperidine/DMF (w/w) solution (360 g) are added 689 non-functionalized methacrylic acid/dimethylacrylamide Multipin™ crowns from Chiron Technologies with an estimated loading of 6.0 mmol/crown. The mixture is gently mixed with orbital shaking for 75 minutes and filtered. The crowns are soaked in DMF (350 mL) for 30 minutes, then filtered. After repeating the DMF wash (350 mL, 30 min) the crowns are washed with methanol (2×350 mL, 30 min each). The crowns are dried under vacuum for 2 hours.

Step 2: FMOC-Lys-(FMOC) Loading:

A mixture of FMOC-Lys-(FMOC) (11.8 g, 20 mmol) and 1-hydroxybenzotriazole (HOBT) (4.0 g, 30 mmol) is dissolved in a mixture of DMF/dichloroethane (1:3, v/v) (450 mL). 1,3-Diisopropylcarbodiimide (DIC) (2.45 g, 19.5 mmol) is added over 20 seconds with mixing. After mixing 10 minutes the crowns from step 1 are added in portions over 1 minute. After gentle orbital mixing for 14 hours, the crowns are filtered, washed with DMF (350 mL, 30 min, 2×) and methanol (350 mL, 30 min, 2×) and dried under vacuum for 2 hours.

Step 3: Piperidine Cleavage:

To a 20% piperidine/DMF (w/w) solution (360 g) are added the crowns from step 2. After gentle orbital mixing for 1 hour the crowns are filtered, washed with DMF (350 mL, 30 min, 2×) and methanol (350 mL, 20 min, 2×) and dried under vacuum for 2 hours.

Step 4: FMOC-Lys-(FMOC) Loading:

A mixture of FMOC-Lys-(FMOC) (8.16 g, 13.8 mmol) and 1-hydroxybenzotriazole (HOBT) (2.8 g, 21 mmol) is dissolved in a mixture of DMF/dichloroethane (1:2, v/v) (400 mL). 1,3-Diisopropylcarbodiimide (DIC) (1.70 g, 13.5 mmol) is added and after mixing for 10 minutes the crowns from step 3 are added in portions over 2 minutes. After gentle orbital mixing for 14 hours, the crowns are filtered, washed with DMF (350 mL, 30 min, 2×) and methanol (350 mL, 30 min, 2×) and dried under vacuum for 2 hours.

Step 5: Piperidine Cleavage:

To a 20% piperidine/DMF (w/w) solution (360 g) are added the crowns from step 4. After gentle orbital mixing for 1 hour, the crowns are filtered, washed with DMF (350 mL, 30 min, 2×) and methanol (350 mL, 20 min, 2×) and dried under vacuum for 2 hours.

Step 6: FMOC-Lys-(FMOC) Loading:

A mixture of FMOC-Lys-(FMOC) (13.0 g, 22 mmol) and 1-hydroxybenzotriazole (HOBT) (4.4 g, 33 mmol) is dissolved in a mixture of DMF/dichloroethane (1:2, v/v) (400 mL). 1,3-Diisopropylcarbodiimide (DIC) (2.77 g, 22 mmol) is added and after mixing for 12 minutes, the crowns from step 5 are added in portions over 1 minute. After gentle orbital mixing for 14 hours, the crowns are filtered, washed with DMF (350 mL, 30 min, 2×) and methanol (350 mL, 30 min, 2×) and dried under vacuum for 2 hours.

Step 7: Piperidine Cleavage:

To a 20% piperidine/DMF (w/w) solution (360 g) are added the crowns from step 6. After gentle orbital mixing for 1.5 hours, the crowns are filtered, washed with DMF (350 mL, 30 min, 2×) and methanol (350 mL, 20 min, 2×) and dried under vacuum for 2 hours.

Step 8: Functionalization of the Triple Lysine Loaded Crowns.

To a solution of 4-hydroxytetrafluorobenzoic acid (10.0 g, 47.6 mmol) in DMF/dichloroethane (1:2, v/v) (400 mL) is added 2-(1H-benzotriazol-1-ly)-1,1,3,3,-tetramethyluronium tetrafluoroborate (TBTU) (15.2 g, 47.6 mmol) with mixing. After 2 minutes, N-methyl morpholine (7.2 g, 71 mmol) is added and after mixing for 1 minute, the triple lysine loaded crowns (step 7 above) are added over 1 minute. After gentle orbital mixing for 14 hours, the crowns are filtered and washed with DMF (350 mL, 10 min). The crowns are soaked with 10% piperidine/DMF (400 mL, 1 h) and then washed with DMF (350 mL, 20 min), 20% 2N HCl/DMF (400 mL, 20 min), DMF (350 mL, 30 min, 2×) and methanol (350 mL, 30 min, 2×) and dried under vacuum for 2 hours.

EXAMPLE 28

Carboxylic Acid Loading to Form Triple Lysine-loaded 4-Hydroxy-2,3,5,6-tetrafluorobenzoyl-fluorophenyl Activated Esters To a mixture of carboxylic acid ($RCO_2H$; 0.040 mmol) and DMF (0.35 mL) is added a solution of DIC (0.04 mmol) and 4-dimethylaminopyridine (DMAP) (0.004 mmol) in DMF (0.05 mL) followed by a triple lysine loaded crown prepared as in Example 24. After 5 hours, the crown is washed with DMF (10 mL, 2 min, 3×) and THF (10 mL, 2 min) and air-dried.

EXAMPLE 29

Cleavage of Triple Lysine-loaded 4-Hydroxy-2,3,5,6-tetrafluorobenzoyl-polyfluorophenyl Activated Esters With Amines A triple lysine-loaded 4-hydroxy-2,3,5,6-tetrafluorobenzoyl-polyfluorophenyl activated ester crown, prepared as in Example 28, is soaked in a 0.01 M DMF solution of amine (0.5 mL) for 12 hours. The crown is removed and the solution concentrated to yield the amide product.

EXAMPLE 30

Quantification of TFP-fluorophenyl Activated Ester Loading

A 0.05 M DMF solution of N-(2,4-dinitrophenyl) ethylenediamine ($DNP-NH_2$) is accurately measured (1.5–2.5 mL) and a TFP-fluorophenyl activated ester crown is added and allowed to react for 2 hours. The sample is examined by reverse phase-high pressure liquid chromatography (RP-HPLC) to measure the area under the curve (AUC) for the product amide at 350 nm. Comparison to a standard curve generated from the 0.05M stock solution of $DNP-NH_2$ allows for an accurate measurement of the quantity of amide.

What is claimed is:

1. A fluorophenyl resin compound of formula

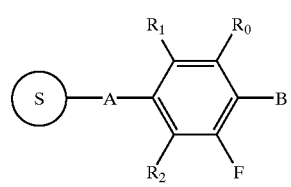

I wherein

is a solid support;
A is selected from

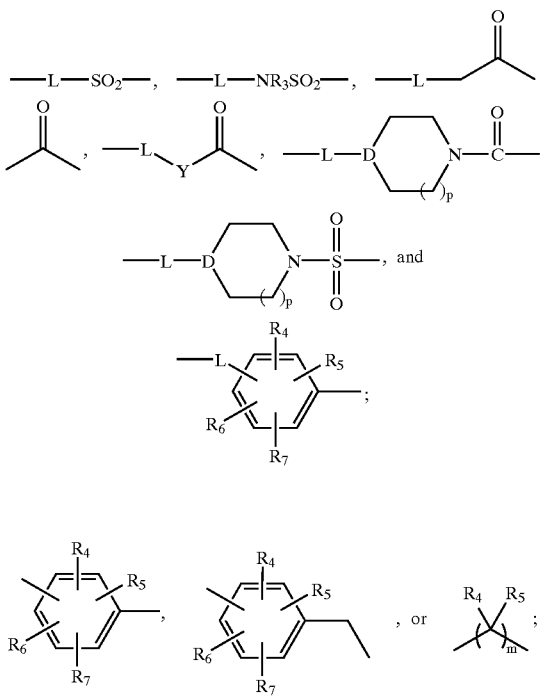

L is a chemical bond,
m is 1 to 5;
p is 0, 1 or 2;
B is F, OW or SO$_2$Z;
D is CH or N;
W is hydrogen, tripyrrolidinophosphonium, C(O)V, C(O)R$_a$, C(O)NR$_b$R$_c$, C(O)Or$_a$, SO$_2$R$_a$ or

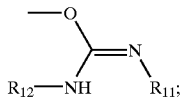

V is Cl or imidazol-1-yl;
Y is O or NR$_3$;
Z is Cl, —OH, OR$_a$ or NR$_a$R$_i$;
R$_a$ and R$_f$ are independently aliphatic or aromatic;
R$_b$ and R$_c$ are independently H, aliphatic or aromatic, or R$_b$ and R$_c$, taken together with the N atom through which they are attached, form an azaheterocyclyl or azaheterocyclenyl;
R$_i$ is CH$_2$R$_f$;
R$_0$, R$_1$ and R$_2$ are a ring system substituent, or R$_0$ and R$_1$ taken together with the adjacent carbon atoms through which they are linked form a 6 membered aryl or 5 to 6 membered heteroaryl;
R$_3$ is H or lower alkyl;
R$_4$, R$_5$, R$_6$ and R$_7$ are independently ring system substituents, or R4 and R5 taken together with the carbon atoms through which they are linked form a 6 membered aryl or 5 to 6 membered heteroaryl; and
R$_{11}$ and R$_{12}$ are independently alkyl, heteroaryl, or aryl.

2. The fluorophenyl resin compound of claim 1 wherein R$_0$, R$_1$ and R$_2$ are F and R$_3$, R$_4$, R$_5$, R$_6$ and R$_7$ are H.

3. The fluorophenyl resin compound of claim 2 wherein A is selected from

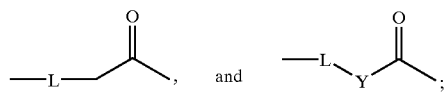

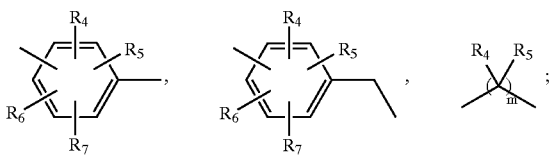

L is a chemical bond,
m is 1; or NR$_3$SO$_2$, wherein Y is O or NR$_3$.

4. The fluorophenyl resin compound of claim 3 wherein Y is NR$_3$ and R$_3$ is H.

5. The fluorophenyl resin compound of claim 4 wherein B is —OH.

6. The fluorophenyl resin compound of claim 4 wherein B is —SO$_3$H or —SO$_2$Cl.

7. A fluorophenyl resin compound according to claim 1 selected from
4-hydroxy-2,3,5,6-tetrafluorobenzamidomethyl-polystyrene resin,
2,3,5,6-tetrafluorobenzamidomethyl-4-sulfonic acid-polystyrene resin,
2,3,5,6-tetrafluorobenzamidomethyl-4-sulfonyl chloride-polystyrene resin,
4-hydroxy-2,3,5,6-tetrafluorobenzoyloxymethyl-polystyrene resin,
2,3,5,6-tetrafluorobenzoyloxymethyl-4-sulfonic acid-polystyrene resin,
2,3,5,6-tetrafluorobenzoyloxymethyl-4-sulfonyl chloride-polystyrene resin,
4-hydroxy-2,3,5,6-tetrafluorobenzoyl-polystyrene resin,
2,3,5,6-tetrafluorobenzoyl-4-sulfonic acid-polystyrene resin,
2,3,5,6-tetrafluorobenzoyl-4-sulfonyl chloride-polystyrene resin,
4-hydroxy-2,3,5,6-tetrafluorophenylsulfonamidomethyl-polystyrene resin,
2,3,5,6-tetrafluorophenylsulfonamidomethyl-4-sulfonic acid-polystyrene resin,
2,3,5,6-tetrafluorophenylsulfonamidomethyl-4-sulfonyl chloride-polystyrene resin,
N-(4-hydroxy-2,3,5,6-tetrafluorobenzoyl)-piperidinomethyl-polystyrene resin,
N-(2,3,5,6-tetrafluorobenzoyl-4-sulfonic acid)-piperidinomethyl-polystyrene resin,
N-(2,3,5,6-tetrafluorobenzoyl-4-sulfonyl chloride)-piperidinomethyl-polystyrene resin,
N-(4-hydroxy-2,3,5,6-tetrafluorophenylsulfonyl)-piperidinomethyl-polystyrene resin,
N-((2,3,5,6-tetrafluorophenyl-4-sulfonic acid)sulfonyl)-piperidinomethyl-polystyrene resin, N-((2,3,5,6-tetrafluorophenyl-4-sulfonyl chloride) sulfonyl)-piperidinomethyl-polystyrene resin, 4-hydroxy-2,3,5,6-tetrafluorophenyl-polystyrene resin, 2,3,5,6-tetrafluorophenyl-4-sulfonic acid-polystyrene resin, 2,3,5,6-tetrafluorophenyl-4-sulfonyl chloride polystyrene resin, 4-hydroxy-2,3,5,6-tetrafluorophenylsulfonyl-polystyrene resin, 4-(tripyrrolidinium-O-phosphonium)-2,3,5,6-tetrafluorobenzamidomethyl-copoly(styrene-1%-divinylbenzene)-resin, 4-(N,N'-diisopropyl-isourea)-2,3,5,6-tetrafluorobenzamidomethyl-copoly(styrene-1%-divinylbenzene)-resin, 2,3,5,6-tetrafluorophenylsulfonyl-4-sulfonic acid-polystyrene resin, and 2,3,5,6-tetrafluorophenylsulfonyl-4-sulfonyl chloride-polystyrene resin.

8. A fluorophenyl resin compound according to claim 1 selected from 4-hydroxy-2,3,5,6-tetrafluorobenzam idomethyl-polystyrene resin, 2,3,5,6-tetrafluorobenzamidomethyl-4-sulfonic acid-polystyrene resin, 2,3,5,6-tetrafluorobenzam idomethyl-4-sulfonyl chloride-polystyrene resin, 4-hydroxy-2,3,5,6-tetrafluorobenzoyl-polystyrene resin, 2,3,5,6-tetrafluorobenzoyl-4-sulfonic acid-polystyrene resin, 2,3,5,6-tetrafluorobenzoyl-4-sulfonyl chloride-polystyrene resin, 4-hydroxy-2,3,5,6-tetrafluorophenylsulfonamidomethyl-polystyrene resin, 4-(tripyrrolidinium-O-phosphonium)-2,3,5,6-tetrafluorobenzamidomethyl-copoly(styrene-1%-divinylbenzene)-resin, 4-(N,N'-diisopropyl-isourea)-2,3,5,6-tetrafluorobenzamidomethyl-copoly(styrene-1%-divinylbenzene)-resin, 2,3,5,6-tetrafluorophenylsulfonamidomethyl-4-sulfonic acid-polystyrene resin and 2,3,5,6-tetrafluorophenylsulfonamidomethyl-4-sulfonyl chloride-polystyrene resin.

9. The fluorophenyl resin compound of claim 4 wherein B is $OC(O)R_a$.

10. A process for preparing an amide of formula

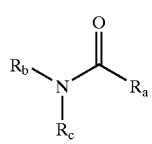

wherein $R_a$ is aliphatic or aromatic; and $R_b$ and $R_c$ are independently H, aliphatic or aromatic, or $R_b$ and $R_c$, taken together with the N atom through which they are attached, form an azaheterocyclyl or azaheterocyclenyl, comprising reacting the fluorophenyl resin compound of claim 9 with a compound of formula $HNR_bR_c$ wherein $R_b$ and $R_c$ are defined above.

11. A process for preparing a fluorophenyl resin compound comprising coupling the fluorophenyl resin compound of claim 5 with a carboxylic acid compound of formula $R_aCO_2H$ wherein $R_a$ is aliphatic or aromatic, optionally in the presence of an activating agent.

12. The fluorophenyl resin compound of claim 4 wherein B is $SO_3R_a$.

13. A process for preparing an amine compound of formula

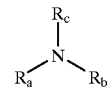

wherein $R_a$ is aliphatic or aromatic; and $R_b$ and $R_c$ are independently H, aliphatic or aromatic, or $R_b$ and $R_c$, taken together with the N atom through which they are attached, form an azaheterocyclyl or azaheterocyclenyl, comprising reacting the fluorophenyl resin compound of claim 12 with a compound of formula $HNR_bR_c$ wherein $R_b$ and $R_c$ are defined above.

14. A process for preparing a fluorophenyl resin compound comprising reacting the fluorophenyl resin compound of claim 6 wherein B is $SO_2Cl$ with a hydroxy compound of formula $R_aOH$ wherein $R_a$ is aliphatic or aromatic.

15. The fluorophenyl resin compound of claim 4 wherein B is $OSO_2R_a$.

16. A process for preparing a sulfonamide compound of formula

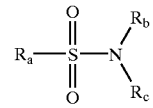

wherein $R_a$ is aliphatic or aromatic; and $R_b$ and $R_c$ are independently H, aliphatic or aromatic, or $R_b$ and $R_c$, taken together with the N atom through which they are attached, form an azaheterocyclyl or azaheterocyclenyl, comprising reacting the fluorophenyl resin compound of claim 15 with a compound of formula $HNR_bR_c$ wherein $R_b$ and $R_c$ are defined above.

17. A process for preparing a fluorophenyl resin compound comprising reacting the fluorophenyl resin compound of claim 5 with a sulfonic anhydride compound of formula $(R_aSO_2)_2O$ or with a sulfonyl chloride compound of formula $R_aSO_2Cl$, wherein $R_a$ is aliphatic or aromatic, in the presence of base.

18. A process for preparing a fluorophenyl resin compound comprising coupling the fluorophenyl resin compound of claim 5 with a sulfonic acid compound of formula $R_aSO_3H$ wherein $R_a$ is aliphatic or aromatic.

19. The process of claim 18 wherein the coupling is carried out in the presence of an activating agent.

20. The process of claim 19 wherein the activating agent is diisopropylcarbodiimide optionally in the presence of 4-dimethylaminopyridine, or bromotripyrrolidinophosphonium hexafluorophosphate (PyBroP™) in the presence of triethylamine (TEA).

21. The fluorophenyl resin compound of claim 4 wherein B is $OC(O)NR_bR_c$.

22. A process for preparing a compound of formula

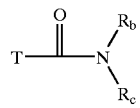

wherein
T is $R_aO$— or $R_dR_eN$—
$R_a$ is aliphatic or aromatic; and
$R_b$, $R_c$, $R_d$ and $R_e$ are independently H, aliphatic or aromatic, or $R_b$ and $R_c$, taken together with the N atom through which they are attached, form an azaheterocyclyl or azaheterocyclenyl, comprising
reacting the fluorophenyl resin compound of claim 21 with an alcohol of formula $R_aOH$, wherein $R_a$ is defined above, in the presence of base or reacting the fluorophenyl resin compound of claim 21 with an amine of formula $R_dR_eNH$, wherein $R_d$ and $R_e$ are defined above, optionally in the presence of base.

23. The fluorophenyl resin compound of claim 4 wherein B is $OC(O)OR_a$.

24. A process for preparing a compound of formula

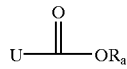

wherein
U is $R_fO$— or $R_bR_cN$—
$R_f$ is aliphatic or aromatic; and
$R_b$ and $R_c$ are independently H, aliphatic or aromatic, or $R_b$ and $R_c$, taken together with the N atom through which they are attached, form an azaheterocyclyl or azaheterocyclenyl, comprising
reacting the fluorophenyl resin compound of claim 23 with an alcohol of formula $R_fOH$, wherein $R_f$ is defined above, or reacting the fluorophenyl resin compound of claim 23 with a compound of formula $R_bR_cNH$, wherein $R_b$ and $R_c$ are defined above, in the presence of base.

25. A process for preparing a fluorophenyl resin compound comprising acylating the fluorophenyl resin compound of claim 5 with an acylating agent of formula $C(O)V_2$ wherein V is Cl or imidazol-1-yl, to yield the acylated fluorophenyl resin compound wherein B is $OC(O)V$; and reacting the acylated fluorophenyl resin with a compound of formula $R_bR_cNH$, wherein $R_b$ and $R_c$ are defined above, optionally in the presence of base.

26. The process of claim 25 wherein the acylating is optionally carried out in the presence of base.

27. A process for preparing a fluorophenyl resin compound comprising reacting the fluorophenyl resin compound of claim 5 with a carbamoyl chloride compound of formula

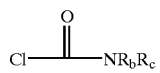

wherein $R_b$ and $R_c$ are independently H, aliphatic or aromatic, or $R_b$ and $R_c$, taken together with the N atom through which they are attached, form an azaheterocyclyl or azaheterocyclenyl, optionally in the presence of base.

28. The fluorophenyl resin compound of claim 4 wherein B is $OC(O)NHR_a$.

29. A process for preparing a fluorophenyl resin compound comprising reacting the fluorophenyl resin compound of claim 5 with an isocyanate compound of formula $O=C=N-R_a$, optionally in the presence of base.

30. The fluorophenyl resin compound of claim 4 wherein B is $SO_2NR_aR_i$.

31. The fluorophenyl resin compound of claim 4 wherein B is $SO_2NHR_a$.

32. A process for preparing a disubstituted amine compound of formula

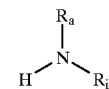

wherein
$R_a$ is aliphatic or aromatic; $R_i$ is $CH_2R_f$; and $R_f$ is aliphatic or aromatic, comprising
reacting the fluorophenyl resin compound of claim 30 with a thiol.

33. The process of claim 32 wherein the thiol is thiophenol or ethanethiol.

34. A process for preparing a fluorophenyl resin compound comprising reacting the fluorophenyl resin compound of claim 6 wherein B is $SO_2Cl$ with a compound of formula $H_2NR_a$ wherein Ra is aliphatic or aromatic.

35. A process for preparing a fluorophenyl resin compound comprising reacting the fluorophenyl resin compound of claim 31 with an alkylating agent of formula $R_iX$ wherein X is Br, Cl or I, in the presence of base.

36. A process for preparing a fluorophenyl resin compound comprising reacting the fluorophenyl resin compound of claim 31 with an alcohol of formula $R_iOH$ in the presence of triphenylphosphine or tributylphosphine and diethylazodicarboxylate or diisopropylazodicarboxylate.

37. The fluorophenyl resin compound of claim 4 wherein B is F.

38. A process for preparing a fluorophenyl resin compound comprising reacting the fluorophenyl resin compound of claim 37 with hydroxide.

39. The process of claim 38 wherein the reacting is under phase-transfer conditions in the presence of a phase transfer catalyst.

40. The process of claim 39 wherein the phase transfer catalyst is tetrabutylammonium hydrogen sulfate.

41. A process for preparing the fluorophenyl resin compound of claim 2 wherein B is F and
A is

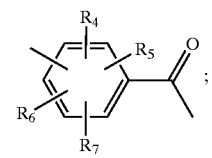

and
$R_4$, $R_5$, $R_6$ and $R_7$ are hydrogen, comprising
acylating a resin compound of formula

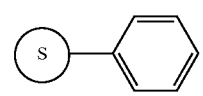

with a 4-fluorofluorobenzoyl chloride compound of formula

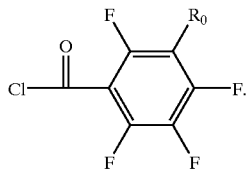

42. The process of claim 41 wherein

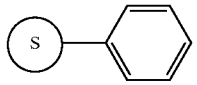

is polystyrene.

43. The process of claim 42 wherein the acylating is in the presence of a Lewis acid.

44. The process of claim 43 wherein the Lewis acid is AlCl$_3$.

45. The fluorophenyl resin compound of claim 37 wherein A is —NR3SO$_2$— wherein R$_3$ is H.

46. A process for preparing the fluorophenyl resin compound of claim 45 comprising reacting an amino resin of formula

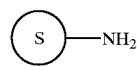

with a tetrafluorophenylsulfonyl chloride compound of formula

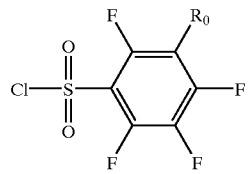

in the presence of base.

47. The process of claim 46 wherein the amino resin is aminomethyl polystyrene.

48. The fluorophenyl resin compound of claim 5 wherein A is —NR$_3$C(O)— wherein R$_3$ is H.

49. A process for preparing the fluorophenyl resin compound of claim 48 comprising coupling an amino resin of formula

with a 4-hydroxyfluorophenyl carboxylic acid compound of formula

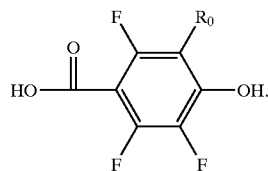

50. The process of claim 49 wherein the coupling is in the presence of an activating agent.

51. The process of claim 50 wherein the activating agent is diisopropylcarbodiimide optionally in the presence of 4-dimethylaminopyridine, or bromotripyrrolidinophosphonium hexafluorophosphate (PyBrop™) in the presence of triethylamine (TEA).

52. The process of claim 51 wherein the amino resin is aminomethyl polystyrene.

53. The fluorophenyl resin compound of claim 6 wherein B is SO$_3$H.

54. A process for preparing a fluorophenyl resin compound comprising reacting the fluorophenyl resin compound of claim 37 with an SO$_3^-$ equivalent.

55. The process of claim 54 wherein the SO$_3^-$ equivalent is potassium metabisulfite.

56. The fluorophenyl resin compound of claim 6 wherein B is SO$_2$Cl.

57. A process for preparing a fluorophenyl resin compound comprising reacting the fluorophenyl resin compound of claim 54 with an inorganic acid chloride.

58. The process of claim 57 wherein the inorganic acid chloride is chlorosulfonic acid.

59. A process for preparing an a-substituted carbonyl compound of formula

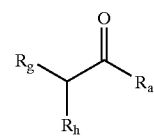

wherein

R$_a$ is aliphatic or aromatic;

R$_g$ is H, aliphatic or aromatic; and

R$_h$ is aliphatic or aromatic, comprising
reacting the fluorophenyl resin compound of claim 9 with a carbon nucleophile of formula

60. The fluorophenyl resin compound of claim 1 wherein B is OH, SO$_3$H or SO$_2$Cl.

61. The fluorophenyl resin compound of claim 1 wherein B is —OC(O)-aryl.

62. The fluorophenyl resin compound of claim 1 wherein B is —S(O)$_2$O-aralkenyl.

63. The fluorophenyl resin compound of claim 1 wherein B is —OS(O)$_2$-aryl or —OS(O)$_2$-heteroaryl.

64. The fluorophenyl resin compound of claim 1 wherein B is —OS(O)$_2$-(phenyl substituted heteroaryl), —OS(O)$_2$-(phenyl substituted phenyl), —OS(O)$_2$-(heteroaryl substituted heteroaryl) or —OS(O)$_2$— (heteroaryl substituted phenyl).

65. The fluorophenyl resin compound of claim 1 wherein R$_4$, R$_5$, R$_6$ and R$_7$ are independently H, alkyl, alkoxy, halogen, CN or NO$_2$.

66. The process of claim 11 wherein the activating agent is diisopropylcarbodiimide optionally in the presence of 4-dimethylaminopyridine, or bromotripyrrolidinophosphonium hexafluorophosphate (PyBroP™) in the presence of triethylamine (TEA).

67. A process for preparing a compound of formula
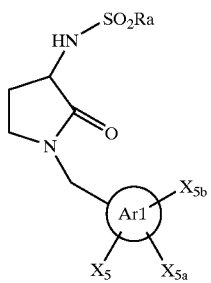
wherein $R_a$ is aliphatic or aromatic; and
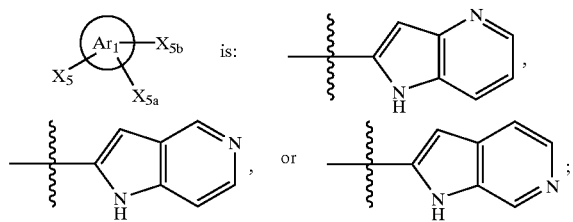
comprising reacting the fluorophenyl resin compound of claim 15 with a compound of formula
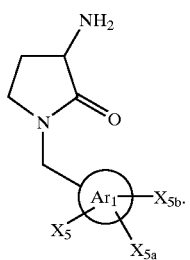
68. A process according to claim 66, wherein $R_a$ is:
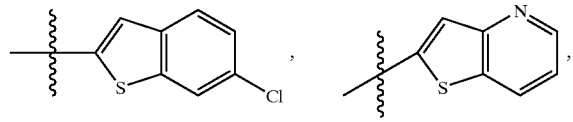
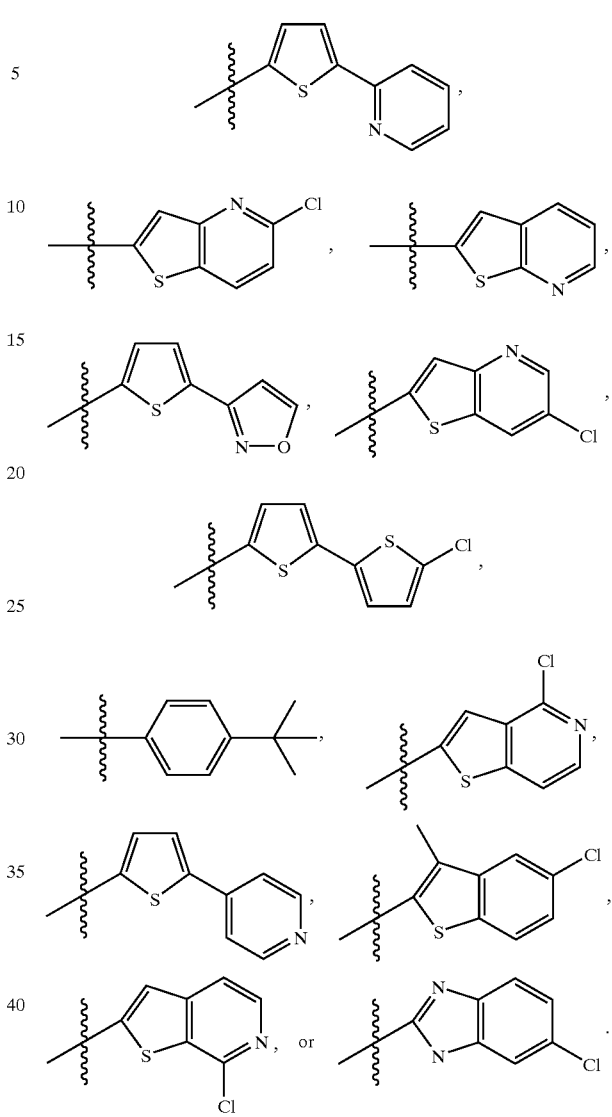
* * * * *